US009610324B2

(12) United States Patent
Pinkosky et al.

(10) Patent No.: US 9,610,324 B2
(45) Date of Patent: Apr. 4, 2017

(54) APOLIPOPROTEIN MIXTURES

(71) Applicant: ESPERION THERAPEUTICS, INC., Plymouth, MI (US)

(72) Inventors: Stephen L. Pinkosky, Plymouth, MI (US); Sergey V. Filippov, Canterbury, CT (US); Timothy R. Hurley, Ann Arbor, MI (US); Rai Ajit K. Srivastava, Churchville, PA (US); Roger S. Newton, Ann Arbor, MI (US)

(73) Assignee: Esperion Therapeutics, Inc., Ann Arbor, MI (US)

( * ) Notice: Subject to any disclaimer, the term of this patent is extended or adjusted under 35 U.S.C. 154(b) by 0 days.

(21) Appl. No.: 14/413,918

(22) PCT Filed: Jul. 11, 2013

(86) PCT No.: PCT/US2013/050116
§ 371 (c)(1),
(2) Date: Jan. 9, 2015

(87) PCT Pub. No.: WO2014/011908
PCT Pub. Date: Jan. 16, 2014

(65) Prior Publication Data
US 2015/0150939 A1 Jun. 4, 2015

Related U.S. Application Data

(60) Provisional application No. 61/670,283, filed on Jul. 11, 2012.

(51) Int. Cl.
*A61K 38/17* (2006.01)
*A61K 9/00* (2006.01)
*C07K 14/775* (2006.01)

(52) U.S. Cl.
CPC ........ *A61K 38/1709* (2013.01); *A61K 9/0019* (2013.01); *C07K 14/775* (2013.01)

(58) Field of Classification Search
CPC .................................................. A61K 38/1709
See application file for complete search history.

(56) References Cited

U.S. PATENT DOCUMENTS

| | | | |
|---|---|---|---|
| 4,376,110 A | 3/1983 | David et al. | |
| 4,816,397 A | 3/1989 | Boss et al. | |
| 4,816,567 A | 3/1989 | Cabilly et al. | |
| 4,946,778 A | 8/1990 | Ladner et al. | |
| 5,059,528 A * | 10/1991 | Bollen | C07K 14/775 435/252.3 |
| 5,585,089 A | 12/1996 | Queen et al. | |
| 5,721,114 A | 2/1998 | Abrahamsen et al. | |
| 7,144,862 B2 | 12/2006 | Fogelman et al. | |
| 7,435,717 B2 | 10/2008 | Bisgaier | |
| 8,143,224 B2 | 3/2012 | Smith et al. | |
| 8,536,117 B2 | 9/2013 | Smith et al. | |
| 8,551,950 B2 | 10/2013 | Smith et al. | |
| 9,051,393 B2 | 6/2015 | Smith et al. | |
| 2002/0064820 A1 | 5/2002 | Dayer et al. | |
| 2003/0109442 A1 | 6/2003 | Bisgaier et al. | |
| 2003/0171277 A1 | 9/2003 | Fogelman et al. | |
| 2004/0067873 A1 | 4/2004 | Dasseux | |
| 2005/0287636 A1 | 12/2005 | Cho | |
| 2006/0030525 A1 | 2/2006 | Marshall et al. | |
| 2009/0149390 A1 | 6/2009 | Smith et al. | |
| 2016/0024182 A1 | 1/2016 | Smith et al. | |

FOREIGN PATENT DOCUMENTS

| | | | |
|---|---|---|---|
| EP | 2573113 | 10/2008 | |
| EP | 2520587 | 11/2012 | |
| WO | WO 8304053 | 11/1983 | |
| WO | WO 9312143 | 6/1993 | |
| WO | WO 2009055538 | 4/2009 | |
| WO | WO 2011/143362 | * 11/2011 | ............. A61K 38/17 |
| WO | WO 2011143362 | 11/2011 | |

OTHER PUBLICATIONS

Ghiselli, G., et al. "Identification of Proapoa-I in Rat Lymph and Plasma: Metabolic Conversion to 'Mature' APOA-I" Biochemical and Biophysical Research Communications, Academic Press, Inc., vol. 116, No. 2 (1983), pp. 704-711.

Ghiselli, G., et al. "Proapolipoprotein A-I conversion kinetics in vivo in human and in rat" Proceedings of the National Academy of Sciences of the United States of America, vol. 82, No. 3 (1985) pp. 874-878.

Westman, J., et al. "In vitro reverse cholesterol transport from THP-1-derived macrophage-like cells with synthetic HDL particles consisting of proapolipoprotein A1 or apolipoprotein A1 and phosphatidylcholine" Scandinavian Journal of Clinical and Laboratory Investigation, vol. 55, No. 1 (1995), pp. 23-33.

PCT/US2013/050116—International Search Report, dated Dec. 18, 2013.

Mendez, Arnando J., et al., "Synthetic Amphipathic Alical Peptides That Mimic Apolipoprotein A-I in Clearing Cellular Cholesterol" The Journal of Clinical Investigation (1994), vol. 94, pp. 1698-1705, downloaded on Nov. 21, 2013.

Ansell, et al., "Inflammatory/Anti-inflammatory Properties of High-Density Lipoprotein Distinguish Patients From Control Subjects Better Than High-Density Lipoprotein Cholesterol Levels and Are Favorably Affected by Simvastatin Treatment", Circulation, 2003, pp. 2751-2756, vol. 108.

Bergt, et al., "Lysine Residues Direct the Chlorination of Tyrosines in YXXK Motifs of Apolipoprotein A-1 When Hypochlorous Acid Oxidizes High Density Lipoprotein", The Journal of Biological Chemistry, 2004, pp. 7856-7866, vol. 279, No. 9.

Bergt, et al., The Myeloperoxidase Product Hypochlorous Acid Oxidizes HDL in the Human Artery Wall and Impairs ABCA1-dependent Cholesterol Transport, PNAS, 2004, pp. 13032-13037, vol. 101, No. 35.

(Continued)

*Primary Examiner* — Amber D Steele
(74) *Attorney, Agent, or Firm* — Honigman Miller Schwartz and Cohn LLP; Fernando Alberdi; Jonathan P. O'Brien

(57) ABSTRACT

The present invention provides a pharmaceutical composition comprising a mixture of apolipoproteins. Methods for elevating HDL levels are also provided as are methods for the treatment and prevention of cardiovascular diseases and disorders, inflammation and metabolic diseases.

60 Claims, 7 Drawing Sheets

(56) References Cited

OTHER PUBLICATIONS

Boullier, et al., "Interplay of Oxygen, Vitamin E., and Carotenoids in Radical Reactions Following Oxidation of Trp and Tyr Residues in Native HDL3 Apolipoproteins. Comparison with LDL. A Time-Resolved Spectroscopic Analysis", Biochemistry, 2007, pp. 5226-5237, vol. 46.

Brouilette, et al., "Structural Models of Human Apolipoprotein A-1: a Critical Analysis and Review", Biochimica et Biophysica Acta, 2001, pp. 4-46, vol. 1531.

Brouilette, et al., Forster Resonance Energy Transfer Measurements Are Consistent with a Helical Bundle Model for Lipid-Free Apolipoprotein A-I +, Biochemistru, 2005, vol. 44, No. 50, pp. 16413-16425.

Brubaker, et al., "Apolipoprotein A-I Lysine Modification: Effects on Helical Content, Lipid Binding and Cholesterol Acceptor Activity", Biochimic et Biophysica Acta, 2006, pp. 64-72, vol. 1761.

Castelli, et al., "Incidence of Coronary Heart Disease and Lipoprotein Cholesterol Levels", JAMA, 1986, pp. 2835-, vol. 256, No. 20.

Datta, et al., "Aromatic Residue Position on the Nonpolar Face of Class A Amphipathic Helical Peptides Determines Biological Activity", The Journal of Biological Chemistry, 2004, pp. 26509-26517, vol. 279, No. 25.

Davidson, et al., "Structural Organization of the N-Terminal Domain of Apolipoprotein A-I: Studies of Tryptophan Mutants", Biochemistry, 1999, pp. 14387-14395, vol. 38.

Denis, et al., "Molecular and Cellular Physiology of Apolipoprotein A-I Lipidation by the ATP-binding Cassette Transporter AI (ABCA1)", The Journal of Biological Chemistry, 2004, pp. 7384-7394, vol. 279, No. 9.

Garner, et al., Oxidation of High Density Lipoproteins, The Journal of Biological Chemistry, 1998, pp. 6088-6095, vol. 273, No. 11.

Gordon, et al., "High-Density Lipoprotein Cholesterol and Cardiovascular Disease. Four prospective American studies", Circulation, 1989, pp. 8-15, vol. 79.

Gross, et al', "A Novel Folding Intermediate State for Apolipoprotein A-I: Role of the Amino and Carboxy Termini", Biophysical Journal, 2006, pp. 1362-1370, vol. 90.

Harrison, et al., "Studies on the Chlorinating Activity of Myeloperoxidase", The Journal of Biological Chemistry, 1976, pp. 1371-1374, vol. 251, No. 5.

Hazen, et al., "3-Chlorotyrosine, a Specific Marker of Myeloperoxidase-catalyzed Oxidation, is Markedly Elevated in Low Density Lipoprotein Isolated from Human Atherosclerotic Intima", The Journal of Clinical Investigation, 1997, pp. 2075-2081, vol. 99, No. 9.

Jerlich, et al., "Kinetics of tryptophan oxidation in plasma lipoproteins by myeloperoxidase-generated HOCl", European Journal of Biochemistry, 2000, pp. 4137-4143, vol. 267.

Kennedy, et al., "ABCG1 Has a Critical Role in Mediating Cholesterol Efflux to HDL and Preventing Cellular Lipid Accumulation", Cell Metabolism, 2005, pp. 121-131, vol. 1.

Maiorano, et al., "Identification and Structural Ramifications of a Hinge Domain in Apolipoprotein A-I Discoidal High-density Lipoproteins of Different Size +", Biochemistry, 2004, vol. 43, No. 37, pp. 11717-11726.

Mulya, et al., "Minimal Lipidation of Pre-I3 HDL by ABCA1 Results in Reduced Ability to Interact with ABCA1", Arteriosclerosis Thrombosis, and Vascular Biology, 2007, pp. 1828-1836, vol. 27.

Nightingale, et al., "Relative Reactivity of Lysine and Other Peptide-Bound Amino Acids to Oxidation by Hypochlorite", Free Radical Biology & Medicine, 2000, pp. 425-433, vol. 29, No. 5.

Nissen, et al., "Effect of Recombinant ApoA-1 Milano Coronary Atherosclerosis in Patients with Acute Coronary Syndromes: A Randomized Controlled Trial", JAMA. 2003, pp. 2292-2300, vol. 290, No. 17.

Oram, et al., "ABCA1 is the cAMP-inducible Apolipoprotein Receptor That Mediates Cholesterol Secretion from Macrophages", The Journal of Biological Chemistry, 2000, pp. 34508-34511, vol. 275, No. 44.

Peng, et al., "Apolipoprotein A-I Tryptophan Substitution Leads to Resistance to Myeloperoxidase-Mediated Loss of Function", Arteriosclerosis, Thrombosis, and Vascular Biology, 2008, pp. 2063-2070, vol. 28, No. 11.

Peng, et al., "Tyrosine Modification is Not required for Myeloperoxidase-induced Loss of Apolipoprotein A-1 Functional Activities", The Journal of Biological Chemistry, 2005, pp. 33775-33784, vol. 280, No. 40.

Pennathur, et al,, "Human Atherosclerotic Intima and Blood of Patients with Established Coronary Artery Disease Contain High Density Lipoprotein Damaged by Reactive Nitrogen Species", The Journal of Biological Chemistry, 2004, pp. 42977-42983, vol. 279, No. 41.

Ryan, et al., "Optimized Bacterial Expression of Human Apolipoprotein A-I" Protein Expression & Purification, 2003, pp. 98-103, vol. 27.

Segrest, et al., "A Detailed Molecular Belt Model for Apolipoprotein A-I in Discoidal High Density Lipoprotein", The Journal of Biological Chemistry, 1999, pp. 31755-31758, vol. 274, No. 45.

Shao, et al., "Tyrosine 192 in Apolipoprotein A-I is the Major Site of Nitration*and Chlorination by Myeloperoxidase, but Only Chlorination Markedly Impairs ABSA1-dependent Cholesterol Transport", The Journal of Biological Chemistry, 2005, pp. 5983-5993, vol. 280, No. 7.

Shao, et al., "Myeloperoxiclase Impairs ABCA1-dependent Cholesterol Efflux Through Methionine Oxidation and Site-specific Tyrosine Chlorination of Apolipoprotein A-I", The Journal of Biological Chemistry, 2006, pp. 9001-9004, vol. 281, No. 14.

Shao, et al., "Methionine oxidation impairs reverse cholesterol transport by apolipoprotein A-1", Proceedings of the National Academy of Sciences of the United States of America, vol. 105, No. 34, 2008, pp. 12224-12229.

Smith, et al., "Cyclic AMP Induces Apolipoprotein E Binding Activity and Promotes Cholesterol Efflux from a Macrophage Cell Line to Apolipoprotein Acceptors", Journal of Biological Chemistry, 1996, pp. 30647-30655, vol. 271, No. 48.

Smith, et al., "ABCA1 Mediates Concurrent Cholesterol and Phospholipid Efflux to Apolipoprotein A-I", Journal of Lipid Research, 2004, pp. 635-644, vol. 45.

Sparks, et al., "Effect of Cholesterol on the Charge and Structure of Apolipoprotein A-I in Recombinant High Density Lipoprotein Particles", The Journal of Biological Chemistry, 1993, pp. 23250-23257, vol. 268, No. 31.

Von Eckardestein, et al., "Structural Analysis of Human Apolipoprotein A-I Variants", The Journal of Biological Chemistry, 1990, pp. 8610-8617, vol. 265, No. 15.

Wang, et al., Macrophage ABCA1 and ABCG1, but not SR-BI, Promote Macrophage Reverse Cholesterol Transport in Vivo, The Journal of Clinical Investigation, 2007, pp. 2216-2224, vol. 117.

Wimley, et al., "Experimentally Determined Hydrophobicity Scale for Proteins at Membrane Interfaces", Nature Structural Biology, 1996, pp. 842-848, vol. 3, No. 10X.

Zheng, et al., "Apolipoprotein A-I is a Selective Target for Myeloperoxidase-catalyzed Oxidation and Functional Impairment in Subjects with Cardiovascular Disease", The Journal of Clinical Investigation, 2004, pp. 529-541, vol. 114.

Zheng, et al., "Localization of Nitration and Chlorination Sites on Apolipoprotein A-I Catalyzed by Myeloperoxidase in Human Atheroma and Associated Oxidative Impairment in ABCA1-Dependent Cholesterol Efflux from Macrophages", The Journal of Biological Chemistry, 2005, pp. 38-47, vol. 280, No. 1.

Davidson, W. Sean, et. al. "Structural Organization of the N-Terminal Domain of Apolipoprotein A-I: Studies of Tryptophan Mutants", Biochemistry 1999, 38, pp. 14387-14395.

Jerlich, Andreas, et al. "Kinetics of tryptophan oxidation in plasma lipoproteins by myeloperoxidase-generated HOCl", Eur. J. Biochem. 267, pp. 4137-4143 (2000).

Nissen, Steven E., et al. "Effect of Recombinant ApoA-I Milano on Coronary Atherosclerosis in Patients With Acute Coronary Syn-

(56) References Cited

OTHER PUBLICATIONS dromes: A Randomized Controlled Trial", JAMA 2003;290(17), pp. 2292-2300.

\* cited by examiner

Maximum Concentration Achieved

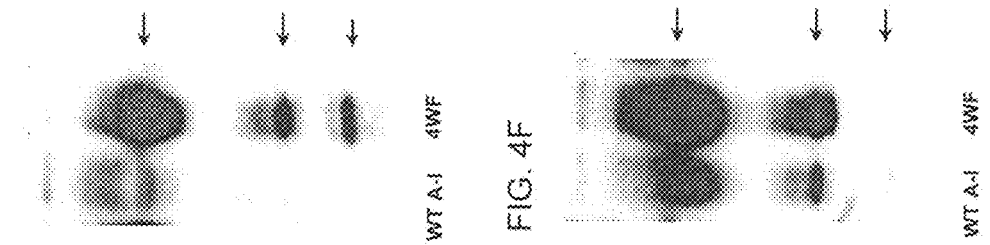
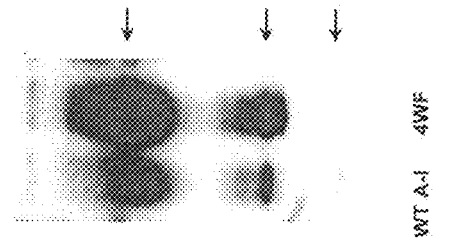
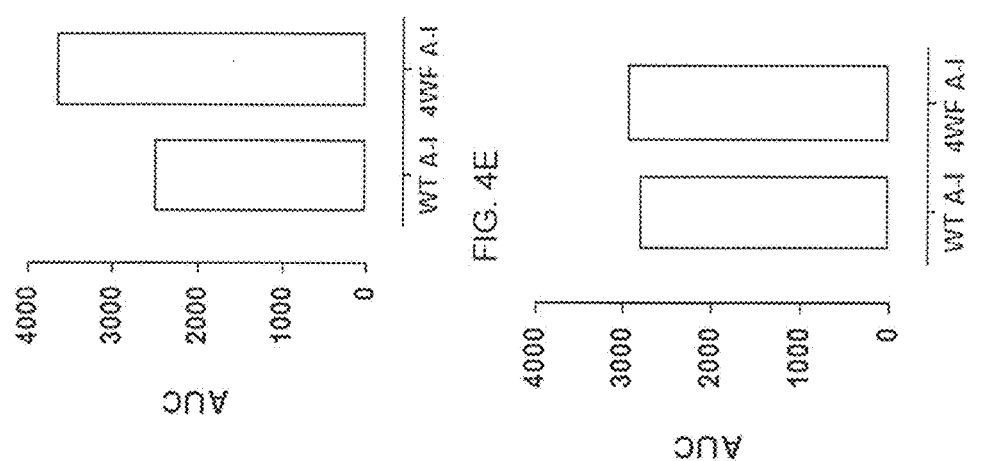
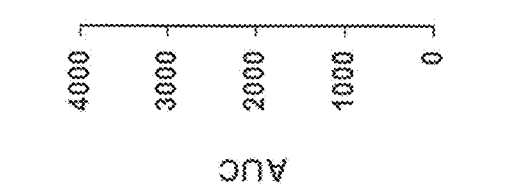
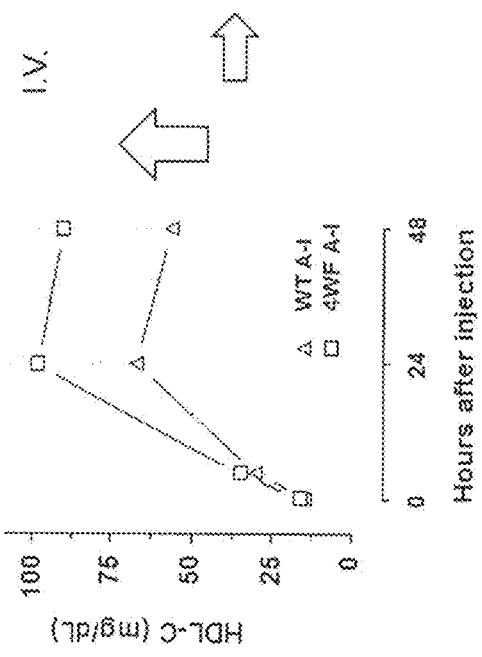
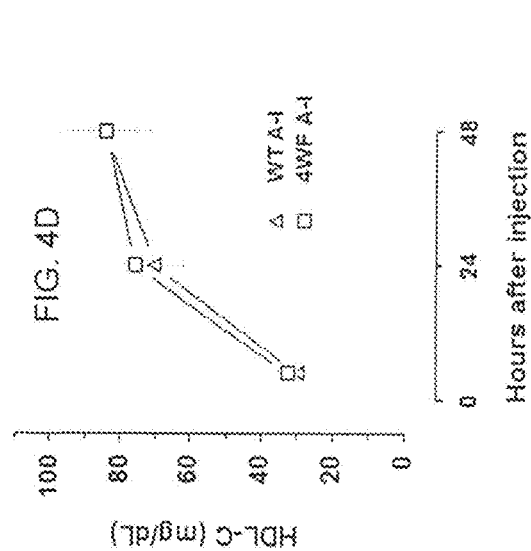

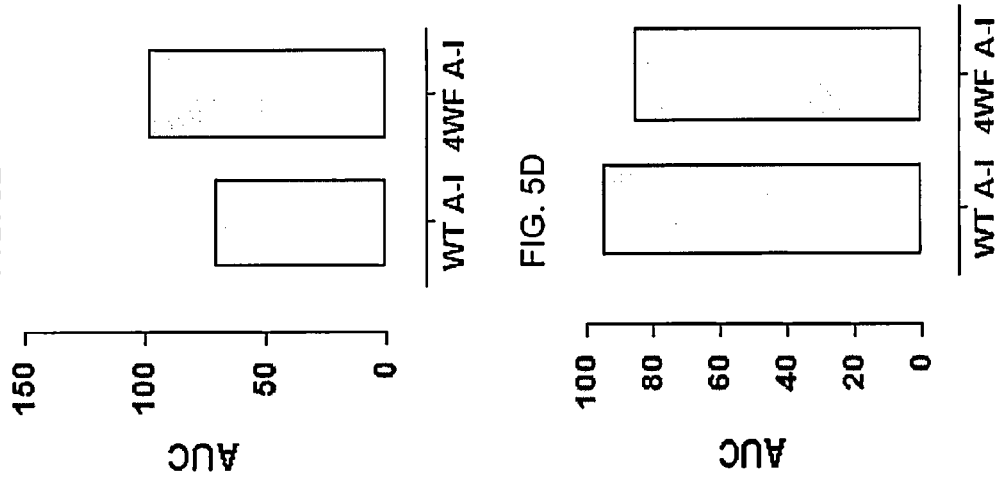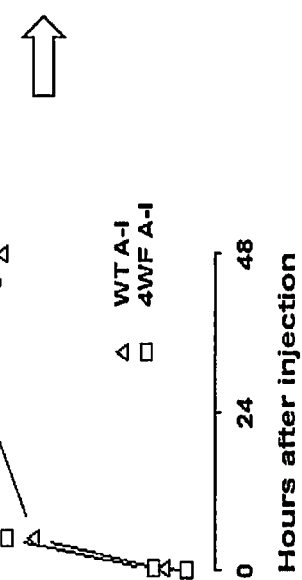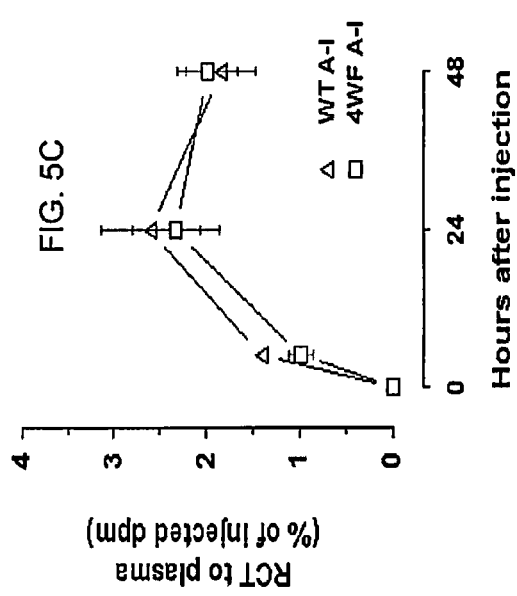

Control

Apo-4WF

WT-Apo-AI

Control

Apo-4WF

WT-Apo-AI

FIG. 7A

```
RHFWQQDEPP QSPWDRVKDL ATVYVDVLKD SGRDYVSQFE GSALGKQLNL KLLDNWDSVT    60
STFSKLREQL GPVTQEFWDN LEKETEGLRQ EMSKDLEEVK AKVQPYLDDF QKKWQEEMEL   120
YRQKVEPLRA ELQEGARQKL HELQEKLSPL GEEMRDRARA HVDALRTHLA PYSDELRQRL   180
AARLEALKEN GGARLAEYHA KATEHLSTLS EKAKPALEDL RQGLLPVLES FKVSFLSALE   240
EYTKKLNTQ - SEQ ID NO:1
```

FIG. 7B

```
DEPPQSPWDR VKDLATVYVD VLKDSGRDYV SQFEGSALGK QLNLKLLDNW DSVTSTFSKL    60
REQLGPVTQE FWDNLEKETE GLRQEMSKDL EEVKAKVQPY LDDFQKKWQE EMELYRQKVE   120
PLRAELQEGA RQKLHELQEK LSPLGEEMRD RARAHVDALR THLAPYSDEL RQRLAARLEA   180
LKENGGARLA EYHAKATEHL STLSEKAKPA LEDLRQGLLP VLESFKVSFL SALEEYTKKL   240
NTQ - SEQ ID NO:2
```

FIG. 8A

```
RHFWQQDEPP QSPFDRVKDL ATVYVDVLKD SGRDYVSQFE GSALGKQLNL KLLDNFDSVT    60
STFSKLREQL GPVTQEFFDN LEKETEGLRQ EMSKDLEEVK AKVQPYLDDF QKKFQEEMEL   120
YRQKVEPLRA ELQEGARQKL HELQEKLSPL GEEMRDRARA HVDALRTHLA PYSDELRQRL   180
AARLEALKEN GGARLAEYHA KATEHLSTLS EKAKPALEDL RQGLLPVLES FKVSFLSALE   240
EYTKKLNTQ - SEQ ID NO:3
```

FIG. 8B

```
DEPPQSPFDR VKDLATVYVD VLKDSGRDYV SQFEGSALGK QLNLKLLDNF DSVTSTFSKL    60
REQLGPVTQE FFDNLEKETE GLRQEMSKDL EEVKAKVQPY LDDFQKKFQE EMELYRQKVE   120
PLRAELQEGA RQKLHELQEK LSPLGEEMRD RARAHVDALR THLAPYSDEL RQRLAARLEA   180
LKENGGARLA EYHAKATEHL STLSEKAKPA LEDLRQGLLP VLESFKVSFL SALEEYTKKL   240
NTQ - SEQ ID NO:4
```

APOLIPOPROTEIN MIXTURES

CROSS REFERENCE TO RELATED APPLICATIONS

This application is a 35 U.S.C. §371(c) United States National Phase filing of International Application Serial No. PCT/US2013/050116, filed Jul. 11, 2013, which claims the benefit of U.S. Provisional Patent Application Ser. No. 61/670,283, filed Jul. 11, 2012, the disclosures of which are incorporated herein by reference in their entirety.

INCORPORATION BY REFERENCE OF MATERIAL SUBMITTED ELECTRONICALLY

Incorporated by reference in its entirety is a computer-readable sequence listing submitted concurrently herewith and identified as follows: One 8.68 KB ASCII (Text) file named "221877-342317_Seq_Listing_ST25.txt," created on Jul. 10, 2013, at 12:54 pm.

FIELD OF THE INVENTION

This invention relates to compositions of apolipoproteins, and methods of their manufacture and use for the prevention and treatment of disease.

BACKGROUND OF THE INVENTION

High Density Lipoproteins (HDL, i.e. "good cholesterol") are protein-heavy particles of lipid and protein which circulate in the blood and play a primary role in removing fatty deposits from arterial walls and returning them to the liver for elimination. As such, high blood concentrations of HDL are associated with reduced formation of arterial plaques, atherosclerosis, and incidence of myocardial infarctions.

Human apolipoprotein-AI ("human Apo-AI") is the primary protein constituent of HDL. For this reason, Apo-AI and its variants have received considerable interest as potential therapeutic agents for the treatment of atherosclerosis and a number of other acute or chronic disease conditions. Variants of human Apo-AI of potential therapeutic interest include naturally occurring isoforms (e.g. mature protein and pro-protein), naturally occurring point-substitution variants (e.g. Milano and Paris), created point-substitution variants, and peptide mimetics (e.g. fragments of Apo-AI comprising individual secondary structural motifs).

In animal cells, Apo-AI is initially expressed in the endoplasmic reticulum as a 267 amino acid preproprotein. Following cleavage of the 18 amino acid signal peptide and transport across the Golgi apparatus, the proprotein is secreted into the extracellular space. Subsequently, the 6-amino acid N-terminal pro-sequence is cleaved, leaving the 243 residue, mature protein (Proc. Nat. Acad. Sci. 80, 2574 (1983)).

Apo-AI can be purified from serum, but has also been expressed as a recombinant protein in multiple expression systems, including mammalian cell culture, insect cells, plant seed, and bacterial cells. Due to its amphipathic nature, solubility of the purified protein is fairly low: in the range of 1-5 mg/mL. In one example, commercially available human Apo-AI is sold as a solubilized protein solution of 1 mg/mL for delipidated, purified protein (See for example, Catalog No. CYT-037-APOAI1 mg/ml solution contains 10 mM Ammonium Bicarbonate at pH7.4, ProSpec-Tany Techno-Gene Ltd, East Brunswick, N.J., USA). Because of this poor solubility, and the need to achieve more concentrated formulations for therapeutic administration, purified Apo-AI has typically been solubilized at higher concentrations in conjunction with various lipid co-solutes. For example, recombinant pro-Apo-AI overexpressed in bacteria was solubilized by addition of dimyristoyl phosphatidylcholine (EP 0308336A2). Other applications have disclosed the use of sphingomyelin or 1-palmitoyl-2-oleoyl phosphatidylcholine to improve the protein's solubility (U.S. Pat. No. 7,435,717). However, these methods only demonstrate actual Apo-AI solubilities in the range of about 20 mg/mL or less.

Because of the relatively poor solubility of Apo-AI under all known conditions, approaches for therapeutic administration of the protein have called for infusion of a large volume of protein solution over a long period of time. For example, in U.S. Pat. No. 7,435,717, methods disclose administering approximately 50 mL solution containing 10 mg/mL Apo-AI, to a patient via infusion over a course of approximately 2 hours Administration of a single Apo-AI dose would be made considerably more convenient if it could be done via syringe, rather than through infusion of a relatively large volume of liquid for an extended time. This would enable, for example, a patient to self-inject at home in a matter of minutes, rather than having to go to a hospital for a multi-hour infusion. However, since syringe injection would typically be about 1-50, or 1-25 mL or less in volume, and suggested daily or weekly dosages of Apo-AI have typically been on the order of hundreds to thousands of milligrams, this would require a solution containing Apo-AI at a concentration far higher than is possible to attain by any known method to date. However, while there has been considerable effort by pharmaceutical companies to produce new compounds for treating deficiency of HDL diseases, such as, atherosclerosis, there are currently no drugs on the market that have the ability to promote the mobilization and efflux of stored cholesterol from macrophages located in atherosclerotic plaques. Methods for increasing the solubility of Apo-AI to form stable compositions comprising these higher concentrations of Apo-AI above what is presently available, would solve this problem.

SUMMARY

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

In some embodiments, the present invention provides compositions, pharmaceutical compositions, and formulations that comprise a mixture of a proapolipoprotein and its corresponding mature apolipoprotein. The mixture of proapolipoprotein and its corresponding mature apolipoprotein can include combinations of proapolipoproteins and corresponding mature apolipoproteins from Apo-AI, Apo-AII, Apo-AIV, Apo-AV, Apo-B, Apo-E and mimetics, analogs, orthologs, and natural and artificial mutation variants of these, including Apo-AI-4WF. In some embodiments, the mixture of proapolipoprotein and its corresponding mature apolipoprotein exists in a ratio of proapolipoppprotein to mature apolipoprotein ranging from 5:95 to about 95:5 (w/w %), and ratios therebetween. In various embodiments, the compositions, pharmaceutical compositions, injectable apolipoprotein compostions or formulations can contain a mixture with a ratio of proapolipoprotein and its corresponding mature apolipoprotein in the mixture ranging from 5:95 to about 95:5, 20:80 to about 80:20, 35:65 to about 65:35, 40:60 to about 60:40, 45:55 to about 55:45, or about 50:50 all expressed on a weight per weight percent basis (wt %).

In another aspect, the present invention provides injectable apolipoprotein compositions. In some embodiments, the injectable apolipoprotein composition can comprise: a) mixture of proapolipoprotein and a corresponding mature apolipoprotein, and b) at least one pharmaceutically acceptable excipient. In some embodiments, the amount of the combined proapolipoprotein to corresponding mature apolipoprotein in the mixture is about 25 mg to about 5,000 mg. In some embodiments, the mixture of proapolipoprotein and a corresponding mature apolipoprotein in the injectable apolipoprotein composition have been or are solubilized in a pharmaceutuically acceptable excipient.

In another aspect, the present invention provides a method for preparing a stable apolipoprotein injectable composition. The method steps can include: combining a) a mixture of proapolipoprotein and a corresponding mature apolipoprotein. The mixture can have a ratio of proapolipoprotein to its corresponding apolipoprotein ranging from about 5:95 to about 95:5 (wt %). The mixture of proapolipoprotein and a corresponding mature apolipoprotein can then be combined with b), at least one pharmaceutically acceptable excipient. In some embodiments, the pharmaceutically acceptable excipient can include a solubilizer, or a suspending agent, an isotonic agent, a buffering agent, a pH adjusting agent or combinations thereof.

In one aspect, the present invention provides a method for concentrating a mature apolipoprotein in solution, the method comprises the steps: (a) providing a first solution comprising a mixture of a proapolipoprotein and its corresponding mature apolipoprotein, (b) concentrating the first solution to a first concentrated volume; and (c) adding a second solution comprising the mature apolipoprotein to the first concentrated volume to form a second concentrated volume. In some embodiments, the method for concentrating a mature apolipoprotein in solution optionally includes repeating steps (b) and (c) until a desired concentration of the mature apolipoprotein is achieved in a final concentrated volume. In some embodiments, the desired concentration of the mixture can range from about 50 mg/mL to about 300, or 400 mg/mL. In some embodiments, the mixture of a proapolipoprotein and its corresponding mature apolipoprotein can include such mixtures of apolipoprotein-AI, apolipoprotein-AII, apolipoprotein AIV, apolipoprotein-AV, apolipoprotein B, apolipoprotein E, apolipoprotein AI-Milano, apolipoprotein AI-Paris, apolipoprotein AI-Marburg, apolipoprotein AI-4WF and apolipoproteins comprising natural and synthetic mutations thereof.

In some embodiments, the compositions, pharmaceutical compositions, injectable apolipoprotein compositions, and formulations described above and when used in the methods described herein are substantially free of one or more of phospholipids, lipids, trigycerides, glycerol, cholesterol, or liposomes.

The compositions, pharmaceutical compositions, injectable apolipoprotein compostions, or formulations of the present invention can be used to treat diseases associated with abnormal and or unregulated cellular activities associated with impaired HDL production, or low circulating levels of HDL or low levels of one or more apolipoproteins, for example, Apo-AI.

In another aspect, the present invention provides methods for increasing the plasma concentration of HDL in a subject, for example, a mammal, for example, a human. The subject may be in need of increasing their HDL levels, for example, if the human subject's HDL plasma level of less than 40 mg/dL, a low HDL/LDL ratio, or if the subject has high low density cholesterol, or very low density cholesterol, or has a total cholesterol higher than 200 mg/dL or the total cholesterol is higher than the recommended cholesterol levels as promulgated by state or national medical recommendations. In some embodiments, the method comprises administering a therapeutically effective amount of a pharmaceutical composition comprising a mixture of a proapolipoprotein and its corresponding mature apolipoprotein and a pharmaceutically acceptable excipient to the subject. In some embodiments, the pharmaceutical composition can include at least 25 mg of the mixture, or at least 100-400 mg, wherein the ratio of proapolipoprotein to corresponding apolipoprotein in the mixture ranges from about 5:95 to about 95:5 (wt %) and ratios therebetween. In some embodiments, the pharmaceutical composition can include at least 500 mg of a mixture of a proapolipoprotein and its corresponding mature apolipoprotein, or at least 1,000-5,000 mg of the mixture of a proapolipoprotein and its corresponding mature apolipoprotein. In some embodiments, the pharmaceutical composition comprises 25 mg to 5,000 mg, or 25 mg to 8,350 mg of a mixture of a proapolipoprotein and its corresponding mature apolipoprotein, and at least one pharmaceutically acceptable excipient. In some embodiments, the pharmaceutical composition comprises about 25 mg to about 5,000 mg of a mixture of a proapolipoprotein and its corresponding mature apolipoprotein, and at least one pharmaceutically acceptable excipient, wherein the pharmaceutical composition is substantially free of one or more of phospholipids, lipids, trigycerides, glycerol, cholesterol or liposomes. In one embodiment, the pharmaceutical composition comprises about 25 mg to about 5,000 mg of a mixture of a proapolipoprotein and its corresponding mature apolipoprotein suitably suspended in a volume ranging from 0.5-50 mL, optionally for parenteral administration (for example, intravenous, subcutaneous, intraperitoneal, or intramuscular administration) wherein the ratio of the proapolipoprotein to corresponding apolipoprotein in the mixture ranges from about 5:95 to about 95:5 (wt %) and ratios therebetween.

In some embodiments, individual doses of the composition, or pharmaceutical composition, can be administered in 30 mL or less, or 20 mL or less, or 15 mL or less, or 10 mL or less, or 5 mL or less, or 2.0 mL or less, or 1.5 mL or less, or 1.0 mL or less, in an injectable apolipoprotein composition.

In some embodiments, a method for treating a subject having a disease associated with abnormal and or unregulated cellular activities associated with impaired HDL production, or low circulating levels of HDL or low levels of one or more apolipoproteins includes administering the pharmaceutical composition at least once per day, or at least twice per day, or once per week, or at least twice per week, sufficient to achieve a total daily and/or weekly dose of 0.01 mg/kg/day to 100 mg/kg/day, or 0.01 mg/kg/week to 100 mg/kg/week.

In another aspect of the present invention, methods are provided for the prevention and/or treatment of a cardiovascular disease or disorder in a subject. In some embodiments, the method comprises administering to the subject a therapeutically effective amount of a pharmaceutical composition comprising a mixture of a proapolipoprotein and a corresponding mature apolipoprotein. In some embodiments, a cardiovascular disease or disorder can be congenital or associated with one or more risk factors of cardiovascular disease, for example, high levels of circulating plasma cholesterol, low HDL levels (below 40 mg/dL), a low HDULDL ratio, i.e. ≤0.75-1, vascular inflammation, high circulating levels of triglycerides, and lack of physical activity. As used herein, a cardiovascular disease can include a disease or disorder of the coronary, cerebral, and peripheral vasculature and diseases or disorders related thereto. In some embodiments, a cardiovascular disease can include, aneurysms, angina, arrhythmia, atherosclerosis, arteriosclerosis, cardiomyopathy, cerebrovascular disease, congenital heart disease, congestive heart failure, coronary artery disease, hyperlipidemia, hypercholesterolemia, myocarditis, valve disease, coronary artery disease, dilated cardiomyopathy, diastolic dysfunction, endocarditis, hypertension, hypertrophic cardiomyopathy, mitral valve prolapse, myocardial infarction, stroke, vascular stenosis or venous thromboembolism.

In another embodiment, the present invention provides methods for the treatment of a metabolic disease or disorder in a subject, for example metabolic syndrome or metabolic diseases having an inflammation component. In some embodiments, the method comprises administering to the subject, a therapeutically effective amount of a pharmaceutical composition comprising a mixture of a proapolipoprotein and a corresponding mature apolipoprotein.

In some embodiments of the above methods, the proapolipoprotein and corresponding mature apolipoprotein comprise apolipoprotein-AI, apolipoprotein-AII, apolipoprotein-AIV, apolipoprotein-AV, apolipoprotein B, apolipoprotein E, apolipoprotein-AI-Milano, apolipoprotein-AI-Paris, apolipoprotein-AI-Marburg, apolipoprotein-AI-4WF, and natural and synthetic mutants thereof.

In some embodiments, the ratio of proapolipoprotein to corresponding mature apolipoprotein in the mixture range from about 5:95 to about 95:5 (wt %), for example, from about 20:80 to about 80:20, or from about 35:65 to about 65:35, or from about 40:60 to about 60:40, or from about 45:55 to about 55:45 or about 50:50 (wt %).

In some embodiments of the methods useful in the treatment of a cardiovascular disease, or a metabolic disease, the therapeutically effective amount of mature apolipoprotein present in the pharmaceutical composition or administered in each dose or unit dose, can include from at least about 25 mg, or at least 50 mg, or at least 75 mg, or at least 100 mg, or at least 125 mg, or at least 150 mg, or at least 175 mg, or at least 200 mg, or at least 250 mg, or at least 300 mg, or at least 400 mg. In some embodiments, the therapeutically effective amount of a mixture of a proapolipoprotein and its corresponding mature apolipoprotein in a pharmaceutical composition is at least about 25, or at least about 100 mg, or at least about 125 mg, or at least about 150 mg, or at least about 175 mg, or at least about 200 mg, or at least about 225 mg, or at least about 250 mg, or at least about 300 mg, or at least about 400 mg, or at least about 500 mg, or at least about 750 mg, or at least about 1,000 mg, or at least about 1,250 mg, or at least about 1,500 mg, or at least about 1,750 mg, or at least about 2,000 mg, or at least about 2,250 mg, or at least about 2,500 mg, or at least about 2,740 mg, or at least about 3,000 mg, or at least about 3,250 mg, or at least about 5,000 mg. In some embodiments, the daily or weekly dose or unit dose comprising the pharmaceutical composition can be administered in one or more doses at least once per day, or one or more doses at least twice per day, or one or more doses administered every 4 hours, or every 8 hours, or every 12 hours, or every 24 hours, or every 36 hours, or every 48 hours, or once per week, or one or more times per week, or once per two weeks, one or more doses per day, two or more times per two weeks or once per month, or combinations thereof. In some embodiments, the one or more doses administered at least once per week can be divided throughout the day, or administered at the same time.

BRIEF DESCRIPTION OF THE DRAWINGS

The drawings described herein are for illustration purposes only and are not intended to limit the scope of the present disclosure in any way.

FIG. 4A illustrates a line chart indicating the relative HDL particle formation formed in vivo using mixtures of proapolipoprotein and its corresponding mature apolipoprotein when injected intravenously (I.V.) into ApoAI-/-mice.

FIG. 4B shows a bar chart representing the area under the curve (AUC) of the experimental results obtained in FIG. 4A.

FIG. 4C is a western blot electropherogram indicating the relative amount of apolipoprotein incorporated into particles when administered I.V. Arrows indicate relative size of the particles formed when injected intravenously (I.V.) into ApoAI -/- mice.

FIG. 4D illustrates a line chart indicating the relative HDL particle formation formed in vivo using mixtures of proapolipoprotein and its corresponding mature apolipoprotein when injected subcutaneously (S.C.) into ApoAI -/- mice.

FIG. 4E shows a bar chart representing the area under the curve (AUC) of the experimental results obtained in FIG. 4D.

FIG. 4F is a western blot electropherogram indicating the relative amount of apolipoprotein incorporated into particles when administered S.C. Arrows indicate relative size of the particles formed when injected subcutaneously (S.C.) into ApoAI -/- mice.

FIG. 5A illustrates a line chart indicating the relative reverse cholesterol transportation from macrophages to plasma in vivo using mixtures of proapolipoprotein and its corresponding mature apolipoprotein when injected intravenously (I.V.) into ApoAI −/− mice.

FIG. 5B shows a bar chart representing the area under the curve (AUC) of the experimental results obtained in FIG. 5A.

FIG. 5C illustrates a line chart indicating the relative reverse cholesterol transportation from macrophages to plasma in vivo using mixtures of proapolipoprotein and its corresponding mature apolipoprotein when injected subcutaneously (S.C.) into ApoAI −/− mice.

FIG. 5D shows a bar chart representing the area under the curve (AUC) of the experimental results obtained in FIG. 5C.

FIG. 7A is an amino acid sequence of human wild-type proapolipoprotein (SEQ ID NO:1).

FIG. 7B is an amino acid sequence of human wild-type mature apolipoprotein (SEQ ID NO:2).

FIG. 8A is an amino acid sequence of proapolipoprotein Apo-AI-4WF (SEQ ID NO:3).

FIG. 8B is an amino acid sequence of Apo-AI-4WF mature apolipoprotein (SEQ ID NO:4).

DETAILED DESCRIPTION OF THE INVENTION

A. Definitions

Figure 1:
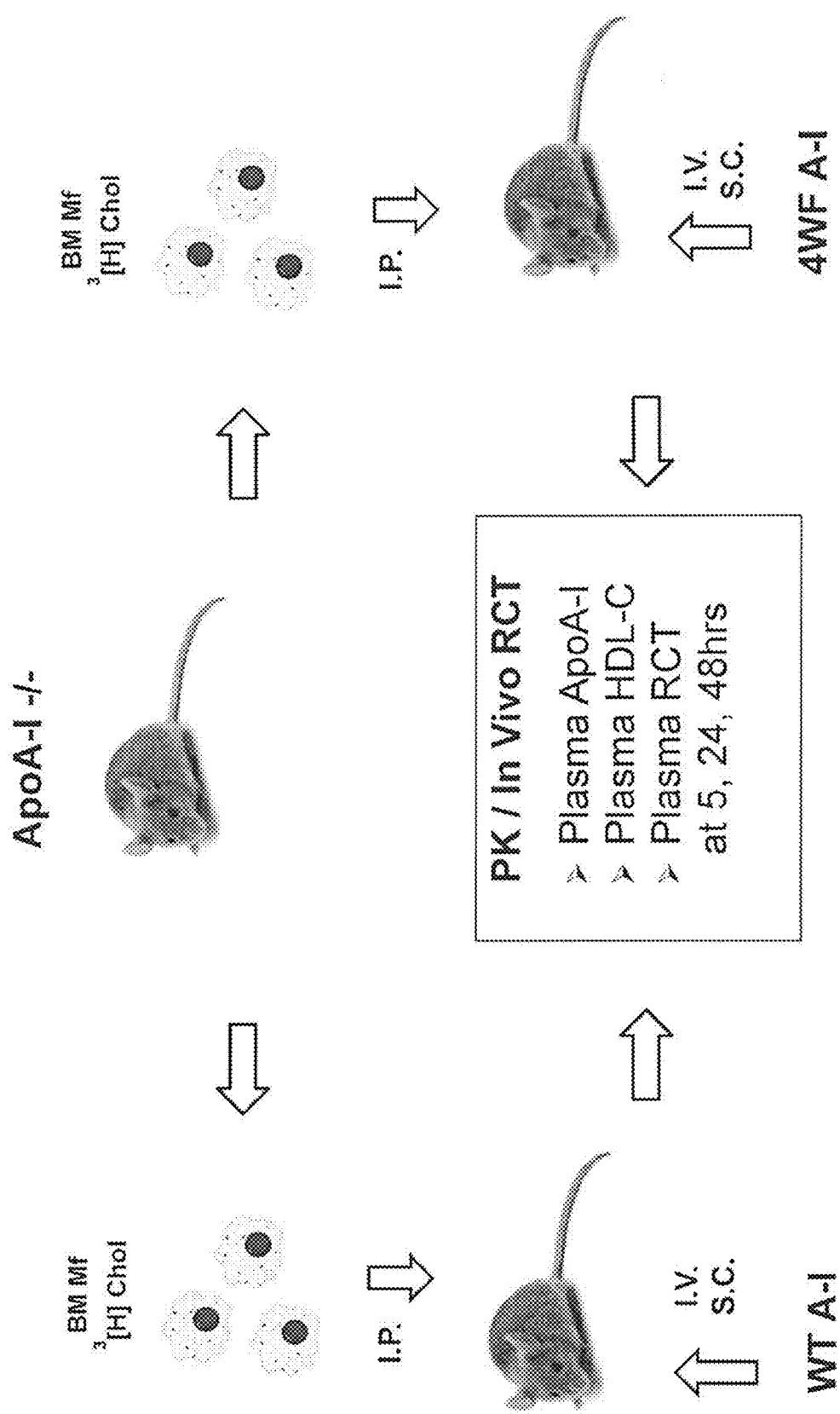
FIG. 1 represents a schematic illustration of the in vivo treatment protocol to measure the plasma residence time, HDL-particle formation and the activity of HDL particles in vivo in reverse transporting cholesterol from lipid loaded macrophages in vivo.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

Although the open-ended term "comprising," as a synonym of terms such as including, containing, or having, is use herein to describe and claim the present invention, the invention, or embodiments thereof, may alternatively be described using more limiting terms such as "consisting of" or "consisting essentially of" the recited ingredients.

As used herein, the term "apolipoprotein" refers to apolipoproteins known to those of skill in the art and variants and fragments thereof and to apolipoprotein agonists, analogs or fragments thereof described below. Suitable apolipoproteins include, but are not limited to, Apo-AI, Apo-AII, Apo-AIV, Apo-AV and Apo-E, and active polymorphic forms, isoforms, variants and mutants, for example, Apo-AI-4WF as well as fragments or truncated forms thereof. Exemplary apolipoprotein-AI proteins are provided in the NCBI databases under Accession No. P02647, version P02647.1: GI: 113992 ranging from amino acid sequence 19-267 (SEQ ID NO:1) and 25-267 (SEQ ID NO:2). Apolipoproteins-AI-4WF (SEQ ID NO: 3 & 4) have the same amino acid sequence of SEQ ID NO: 1 and 2 respectively, with the exception that tryptophan amino acids in the mature sequence of SEQ ID NO: 2 have been mutated with phenylalanine amino acids as described below.

In some embodiments, apolipoproteins of the present invention can also include apolipoproteins in which one or more oxidation labile amino acids, such as tryptophan or tyrosine are substituted with a more oxidant resistant amino acid, for example, phenylalanine or lysine. In some embodiments, apolipoproteins of the present invention include apolipoproteins and mimetics and mutants thereof as disclosed in U.S. Pat. No. 8,143,224, Ser. No. 12/256,822, filed on Oct. 23, 2008, the disclosure of which is incorporated herein by reference in its entirety. In one embodiment, the mixture of proapolipoprotein and corresponding mature apolipoprotein of the present invention have the amino acid sequences of SEQ ID NOs: 1&2 or 3&4. As used herein, apolipoprotein-AI-4WF is abbreviated as Apo-AI-4WF. Proapolipoprotein Apo-AI-4WF has an amino acid sequence of SEQ ID NO:3 and its corresponding mature apolipoprotein Apo-AI-4WF has an amino acid sequence of SEQ ID NO: 4.

In some embodiments, the apolipoprotein is a thiol containing apolipoprotein. "Thiol containing apolipoprotein" refers to an apolipoprotein, variant, fragment or isoform that contains at least one cysteine residue. The most common thiol containing apolipoproteins are Apo-AI Milano (Apo-AI$_M$), Apo-AI Paris (Apo-AI$_P$) and Apo-AI Marburg (Apo-AI$_{Mar}$) which contain one cysteine residue (Jia et al., 2002, Biochem. Biophys. Res. Comm. 297: 206-13; Bielicki and Oda, 2002, Biochemistry 41: 2089-96). Apo-AII, Apo E2 and Apo E3 are also thiol containing apolipoproteins. Isolated ApoE and/or active fragments and polypeptide analogs thereof, including recombinantly produced forms thereof, are described in U.S. Pat. Nos. 5,672,685; 5,525,472; 5,473,039; 5,182,364; 5,177,189; 5,168,045; 5,116,739; the disclosures of which are herein incorporated by reference in their entireties.

Apolipoproteins utilized in the invention also include recombinant, synthetic, semi-synthetic or purified apolipoproteins described above. Methods for obtaining apolipoproteins or functional equivalents thereof, utilized by the invention are well-known in the art. For example, apolipoproteins can be separated from plasma or natural products by, for example, density gradient centrifugation or immunoaffinity chromatography, or produced synthetically, semi-synthetically or using recombinant DNA techniques known to those of the art (see, e.g., Mulugeta et al., 1998, J. Chromatogr. 798(1-2): 83-90; Chung et al., 1980, J. Lipid Res. 21(3):284-91; Cheung et al., 1987, J. Lipid Res. 28(8): 913-29; Persson, et al., 1998, J. Chromatogr. 711:97-109; U.S. Pat. Nos. 5,059,528, 5,834,596, 5,876,968 and 5,721,114; and PCT Publications WO 86/04920 and WO 87/02062, the disclosures of all of the aforementioned referenced publications are incorporated herein by reference in their entireties).

As used herein, the phrase "a proapolipoprotein and a corresponding mature apolipoprotein" generally refers to a pair of apolipoproteins, the first being a proapolipoprotein, for example, human proapolipoprotein-AI (SEQ ID NO: 1) and its corresponding mature apolipoprotein, being the same human proapolipoprotein-AI (SEQ ID NO: 1) minus the 6 amino acid prosequence upstream from the N-terminus of the mature human apolipoprotein sequence, for example, human mature apolipoprotein-AI (Apo-AI) (SEQ ID NO:2) Another example of a proapolipoprotein and a corresponding mature apolipoprotein includes the proapolipoprotein Apo-AI-4WF comprising the amino acid sequence of SEQ ID NO: 3 and the corresponding mature Apo-AI-4WF comprising the amino acid sequence of SEQ ID NO: 4. For clarification purposes only, a "proapolipoprotein and a corresponding mature apolipoprotein" would not include human proapolipoprotein-AI and human mature apol ipoprotein-A2.

"Identity" or "similarity", as known in the art, refers to relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated by known methods such as those described in: Computational Molecular Biology, Lesk, A. M., ed., Oxford University Press, New York, (1988); Biocomputing: Informatics and Genome Projects, Smith, D. W., ed., Academic Press, New York, (1993); Sequence Analysis in Molecular Biology, von Heinje, G., Academic Press, (1987); Computer Analysis of Sequence Data, Part I, Griffin, A. M., and Griffin, H. G., eds., Humana Press, New Jersey, (1994); and Sequence Analysis Primer, Gribskov, M. and Devereux, J., eds., M Stockton Press, New York, (1991). Methods commonly employed to determine identity or similarity between sequences include, but are not limited to those disclosed in Carillo, H. and Lipman, D., SIAM J. Applied Math. 48:1073 (1988). Methods to determine identity and similarity are codified in publicly available computer programs. Computer program methods to determine identity and similarity between two or more sequences include, but are not limited to, GCG program package (Devereux, J., et al., Nucleic Acids Res. (1984) 12(1):387), BLASTP, BLASTN, and FASTA (Paschal, S. F. et al., J. Malec. Biol. (1990) 215: 403).

As used herein and unless otherwise specified, a composition, a pharmaceutical composition, an injectable apolipoprotein composition, a sample, or a formulation that is "substantially free" of one or more of phospholipids, lipids, triglycerides, glycerol, cholesterol or liposomes means that the a composition, a pharmaceutical composition, an injectable apolipoprotein composition, a sample, or a formulation contains, in particular embodiments, less than about 1%, 0.75%, 0.5%, 0.25%, 0.1% or 0.01% percent by weight of the composition or formulation of one or more of phospholipids, lipids, triglycerides, glycerol, cholesterol or liposomes. Preferably, "substantially free" of one or more of phospholipids, lipids, triglycerides, glycerol, cholesterol or liposomes means that the composition, pharmaceutical composition, sample, or formulation contains, in particular embodiments, less than about 0.1% percent by weight of one or more of phospholipids, lipids, triglycerides, glycerol, cholesterol or liposomes in admixture with the proapolipoprotein and/or corresponding mature apolipoprotein in the sample, formulation or composition. In some embodiments, a composition, pharmaceutical composition, sample, or formulation that is "substantially free" of one or more of phospholipids, lipids, trigycerides, glycerol, cholesterol or liposomes means that the composition, pharmaceutical composition, sample, or formulation contains 0% percent by weight one or more of phospholipids, lipids, trigycerides, glycerol, cholesterol or liposomes in admixture with the mature apolipoprotein in the composition, pharmaceutical composition, sample, or formulation.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder or reducing the adverse effects of another drug or medicament resulting from the administration of one or more prophylactic or therapeutic agents or compositions to a patient with such a disease or disorder. In some embodiments, the terms refer to the administration of an apolipoprotein mixture provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a mixture of apolipoproteins as provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment." The terms "prevent," "preventing" and "prevention" also encompass inhibition of a secondary disease that is clinically associated with a primary disease. For example, apolipoprotein mixture compositions of the present invention may be used to prevent the occurrence of a secondary disease, for example, atherosclerosis upon treatment of the patient for a primary indication of hypercholesteremia.

As used herein, and unless otherwise specified, the terms "manage," "managing" and "management" refer to preventing or slowing the progression, spread or worsening of a disease or disorder, or of one or more symptoms thereof, or one or more symptions associated with a secondary disease. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or to reduce the adverse effects of treatment of the disease or disorder with another active agent.

As used herein, and unless otherwise specified, a "therapeutically effective amount" of a mixture of a proapolipoprotein and its corresponding mature apolipoprotein is an amount of the mixture sufficient to provide a therapeutic benefit in the treatment or management of a disease or disorder, or to delay or minimize one or more symptoms associated with the disease or disorder. A therapeutically effective amount of a mixture of a proapolipoprotein and its corresponding mature apolipoprotein means an amount of therapeutic composition, alone or in combination with other therapies, which provides a therapeutic benefit in the treatment or management of the disease or disorder. The term "therapeutically effective amount" can encompass an amount that improves overall therapy, reduces, avoids or eliminates symptoms, reduces side-effects or causes of a disease or disorder, or enhances the therapeutic efficacy of another therapeutic agent.

As used herein, and unless otherwise specified, a "prophylactically effective amount" of a mixture of a proapolipoprotein and its corresponding mature apolipoprotein is an amount sufficient to prevent a disease or disorder, or prevent its recurrence. A prophylactically effective amount of a mixture of a proapolipoprotein and its corresponding mature apolipoprotein means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the diluent, excipient or carrier must be compatible with the other ingredients of the formulation and not deleterious to the recipient thereof.

The term "injectable apolipoprotein composition" as used herein is intended to encompass a composition, or pharmaceutical composition that includes a therapeutically effective amount of a mixture of a proapolipoprotein and its corresponding mature apolipoprotein, the mixture formulated in a volume that may be administered by an injectionable means, such as a syringe, jet injectors, pen injectors, piston syringes, needle free injectors, mechanically operated injectors, injectors with computerized or electronic elements and injectors approved for self administration settings. For example, these injectable apolipoprotein compositions and their associated injectors are designed to provide an accurate method of injecting a dose of a composition or pharmaceutical composition of the present invention contained in a cartridge, reservoir, or syringe through an automatically or manually inserted hypodermic needle(s) or through a high velocity jet. They are intended for use by a healthcare provider or for self-administration by a patient. Injectors used with an "injectable apolipoprotein composition" may be designed for single use or multiple uses, and may be disposable or reusable. For example, a single use injector may be used in acute intervention for treatment or prevention while a multi-dose injector may be used as part of a single patient long term treatment regimen. "Injectable apolipoprotein composition" of the present invention may be administered parenterally, for example, intravenously, intramuscularly, intradermally, intraperitoneally or subcutaneously at the doses described herein, at rates ranging from about 0.1 mL to about 100 mL or more per minute using any commonly known injection methods in the art. The volume of the "injectable apolipoprotein composition" may range from about 0.5 mL to about 30 mL. In various embodiments, the "injectable apolipoprotein composition" if in a liquid form, may be sterilized and substantially free of particulates upon visual inspection by a health care provider or patient prior to administration. "Injectable apolipoprotein composition" of the present invention, generally excludes apoliprotein formulations which are administered using a single dose infusion, which are typically used as part of an infusion therapy requiring greater than 30-500 mL of volume of a pharmaceutical composition in a single dose delivered intravenously using gravity or a pump. Typically, infusions involve continuous slow introduction of a drug or medicament intravenously for a defined period of time.

"Identity" or "similarity", as known in the art, refers to relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated by known methods such as those described in: Computational Molecular Biology, Lesk, A. M., ed., Oxford University Press, New York, (1988); Biocomputing: Informatics and Genome Projects, Smith, D. W., ed., Academic Press, New York, (1993); Sequence Analysis in Molecular Biology, von Heinje, G., Academic Press, (1987); Computer Analysis of Sequence Data, Part I, Griffin, A. M., and Griffin, H. G., eds., Humana Press, New Jersey, (1994); and Sequence Analysis Primer, Gribskov, M. and Devereux, J., eds., M Stockton Press, New York, (1991). Methods commonly employed to determine identity or similarity between sequences includes, but are not limited to those disclosed in Carillo, H. and Lipman, D., SIAM J. Applied Math. 48:1073 (1988). Methods to determine identity and similarity are codified in publicly available computer programs. Computer program methods to determine identity and similarity between two or more sequences include, but are not limited to, GCG program package (Devereux, J., et al., Nucleic Acids Res. (1984) 12(1):387), BLASTP, BLASTN, and FASTA (Paschal, S. F. et al., J. Molec. Biol. (1990) 215: 403).

The term "homologous" refers to the degree of sequence similarity between two polymers (i.e., polypeptide molecules or nucleic acid molecules). The homology percentage figures referred to herein reflect the maximal homology possible between the two polymers, i.e., the percent homology when the two polymers are so aligned as to have the greatest number of matched (homologous) positions.

The term "percent homology" refers to the extent of amino acid or nucleotide sequence identity between polypeptides and polynucleotides respectively. The homology between any two polypeptides or polynucleotides is a direct function of the total number of matching amino acids or nucleotides at a given position in either sequence, e.g., if half of the total number of amino acids or polynucleotides in either of the corresponding sequences is the same then the two sequences are said to exhibit 50% homology.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "ortholog" refers to genes or proteins that are homologs via speciation, e.g., closely related and assumed to have common descent based on structural and functional considerations. Orthologous proteins generally have the same function and the same activity in different species. The term "paralog" refers to genes or proteins that are homologs via gene duplication, e.g., duplicated variants of a gene within a genome. See also, Fritch, W M Syst. Zool. (1970) 19:99-113. The term "ortholog" may refer to a polypeptide from another species that corresponds to human ApoA I polypeptide amino acid sequence as set forth in SEQ ID NOs: 1-4. For example, mouse and human Apo-AI wild-type polypeptides are considered to be orthologs of each other.

The term "fragment", "analog", and "derivative" when referring to the polypeptide of the present invention (e.g., SEQ ID NOs:1-4), can refer to a polypeptide that retains essentially at least one biological function or activity as the reference polypeptide. Thus, an analog includes a precursor protein that can be activated by cleavage of the precursor protein portion to produce an active mature polypeptide. The fragment, analog, or derivative of the polypeptide described herein (e.g., SEQ ID NOs:1-4) may be one having conservative or non-conservative amino acid substitution. The substituted amino acid residues may or may not be encoded by the genetic code, or the substitution may be such that one or more of the substituted amino acid residues includes a substituent group, is one in which the polypeptide is fused with a compound such as polyethylene glycol to increase the half-life of the polypeptide, or one in which additional amino acids are fused to the polypeptide such as a signal peptide or a sequence such as polyhistidine tag which is employed for the purification of the polypeptide or the precursor protein. Such fragments, analogs, or derivatives are deemed to be within the scope of the present invention.

The present inventors have developed novel compositions comprising a mixture of a preapolipoprotein and its corresponding mature apolipoprotein. In other aspects, the inventors have developed pharmaceutical compositions, non-pharmaceutical compositions, and injectable formulations comprising a mixture of a preapolipoprotein and a corresponding mature apolipoprotein. In some aspects, methods for preparing stable injectable formulations, methods for concentrating mature apolipoproteins and methods for increasing the concentration of HDL in vivo are also provided. In some embodiments, the present invention also provides methods for treating or preventing an apolipoprotein deficiency mediated disease or disorder in a subject in need thereof, for example, cardiovascular diseases or disorders and metabolic diseases or disorders.

The inventors of the present invention have surprisingly and unexpectedly developed a method for increasing the solubility of a mature apolipoprotein protein, for example, human mature Apo-AI and oxidant resistant mature Apo-AI-4WF to levels above 50 mg/mL, or above 75 mg/mL, or above 100 mg/mL, or above 125 mg/mL, or above 150 mg/mL or above 200 mg/mL or above 250 mg/mL, without having the mature apolipoprotein denature, or otherwise fall out of solution.

B. Compositions

In some embodiments, a mixture of a proapolipoprotein and its corresponding mature apolipoprotein can be incorporated into a pharmaceutical composition suitable for administration in therapeutically effective amounts to a patient in need thereof to cure, treat or prevent any disease or disorder that would benefit from enhanced cholesterol efflux from lipid laden cells or reduce inflammatory activity. In some embodiments, the present invention provides compositions and pharmaceutical compositions that comprise a mixture of a proapolipoprotein and its corresponding mature apolipoprotein. In some embodiments, the mixture of apolipoproteins can include proapoliporotein-AI and its corresponding mature apolipoprotein-AI; proapoliporotein-AII and its corresponding mature apolipoprotein-AII; proapoliporotein-AIV and its corresponding mature apolipoprotein-AIV; proapoliporotein-AV and its corresponding mature apolipoprotein-AV; proapoliporotein-B and its corresponding mature apolipoprotein-B; proapoliporotein-E and its corresponding mature apolipoprotein-E; proapoliporotein-AI-Milano and its corresponding mature apolipoprotein-AI-Milano; proapoliporotein-AI-Paris and its corresponding mature apolipoprotein-Paris; or proapoliporotein-AI-4WF and its corresponding mature apolipoprotein-AI-4WF. In some embodiments, the mixture of proapolipoprotein and its corresponding mature apolipoprotein comprises a mixture of a human proapolipoprotein and its corresponding mature apolipoprotein. In one example of a mixture comprising a human proapolipoprotein and a corresponding mature apolipoprotein, the human proapolipoprotein is human proapolipoprotein-AI and its corresponding human mature apolipoprotein-AI. In another example of a mixture comprising a proapolipoprotein and a corresponding mature apolipoprotein, the proapolipoprotein is proapoliporotein-AI-4WF and its corresponding mature apolipoprotein-AI-4WF.

Figure 2A:
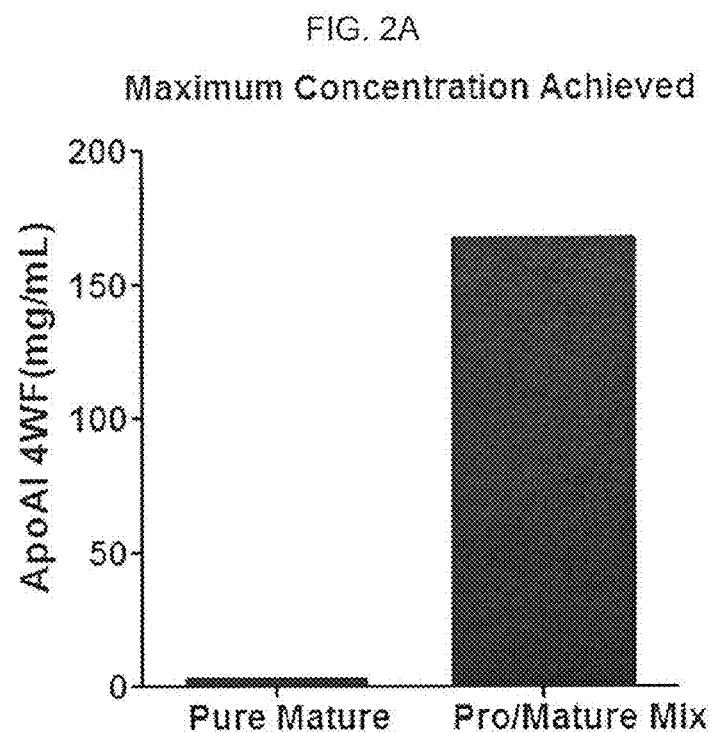
FIG. 2A provides a bar chart comparing the amount of pure mature apolipoprotein AI-4WF and the amount of the mixture of pro-apolipoprotein AI-4WF and mature apolipoprotein AI-4WF concentrated and obtained using the methods described herein.
Figure 2B:
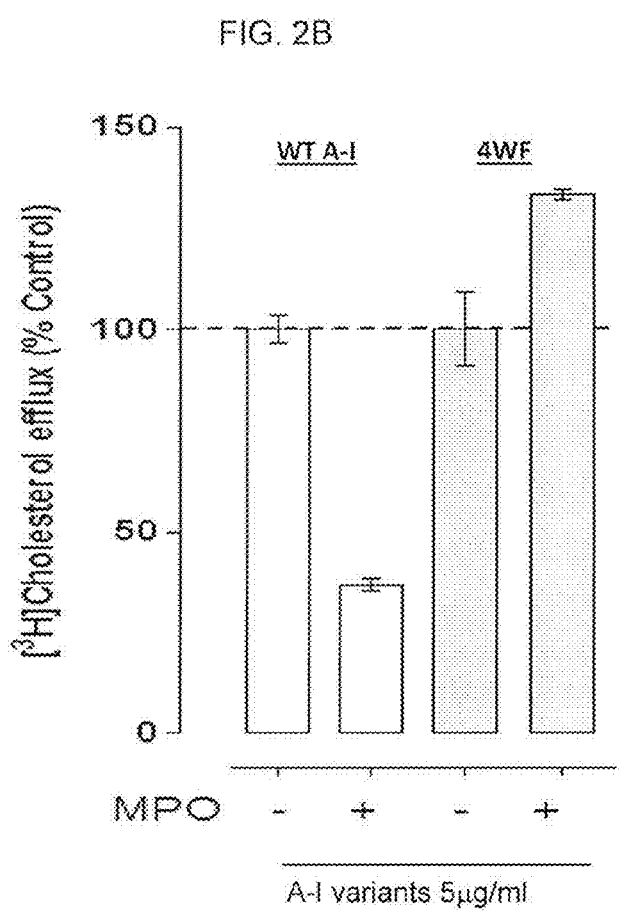
FIG. 2B provides a bar chart illustrating the relative resistance of mixtures of pro and mature apolipoproteins wild-type human Apo-AI and Apo-AI 4WF against myeloperoxidase inhibition of reverse cholesterol transport.

In some embodiments, the human proapolipoprotein-AI has an amino acid sequence of SEQ ID NO:1, and its corresponding mature apolipoprotein has an amino acid sequence of SEQ ID NO: 2. In one embodiment, the mixture comprises proapolipoprotein-4WF with an amino acid sequence of SEQ ID NO: 3 and its corresponding mature apolipoprotein-4WF has an amino acid sequence of SEQ ID NO: 4. The 4WF in the apolipoproteins proapoliporotein-AI-4WF and its corresponding mature apolipoprotein-AI-4WF, designates that the four tryptophan residues in the human mature apolipoprotein-AI amino acid sequence of SEQ ID NO: 1 & 2 are each replaced with a phenylalanine residue. Hence, proapolipoprotein-AI-4WF and its corresponding mature apolipoprotein-AI-4WF are amino acid substitution mutants of the human proapolipoprotein-AI with an amino acid sequence of SEQ ID NO:1, and its corresponding mature apolipoprotein with an amino acid sequence of SEQ ID NO: 2. As shown in FIG. 2, mixture of proapolipoprotein AI-4WF and its mature apolipoprotein AI-4WF in a ratio of 45:55 (wt %) at approximately 5 micrograms per mL was shown to be resistant to myeloperoxidase inactivation when screened for reverse cholesterol transport in vitro.

The compositions and pharmaceutical compositions of the present invention can comprise a combined amount of a human proapolipoprotein and its corresponding mature apolipoprotein ranging from about 25 mg to about 5,000 mg, or from 25 to 8,350 mg, or from about 100 to about 5,000, or from about 200 mg to about 5,000 mg, or from about 300 mg to about 5,000 mg, or from about 400 mg to about 5,000 mg, or from about 500 mg to about 5,000 mg, or from about 600 mg to about 5,000 mg, or from about 700 mg to about 5,000 mg, or from about 800 mg to about 5,000 mg, or from about 900 mg to about 5,000 mg, or from about 1,000 mg to about 5,000 mg, or from about 1,250 mg to about 5,000 mg, or from about 1,500 mg to about 5,000 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg. In some embodiments, the amount of the mixture of a preapolipoprotein and its corresponding apolipoprotein in the composition or pharmaceutical composition is at least 20 mg, or at least 30 mg, or at least 40 mg, or at least 50 mg, or at least 60 mg, or at least 70 mg, or at least 80 mg, or at least 90 mg, or at least 100 mg, or at least 110 mg, or at least 120 mg, or at least 130 mg, or at least 140 mg, or at least 150 mg, or at least 160 mg, or at least 170 mg, or at least 1900 mg, or at least 200 mg, or at least 225 mg, or at least 250 mg, or at least 275 mg, or at least 280 mg, or at least 300 mg, or at least 400 mg. In various embodiments, the aforementioned compositions or pharmaceutical compositions are substantially free of one or more of of phospholipids, lipids, trigycerides, glycerol, cholesterol or liposomes.

The compositions and pharmaceutical compositions of the present invention can comprise a combined amount of a human proapolipoprotein and its corresponding mature apolipoprotein sufficient to provide a dose of about 0.01 mg/kg, or about 0.1 mg/kg, or about 1 mg/kg, or about 2 mg/kg, or about 3 mg/kg, or about 4 mg/kg, or about 5 mg/kg, or about 6 mg/kg, or about 7 mg/kg, or about 8 mg/kg, or about 9 mg/kg, or about 10 mg/kg, or about 12 mg/kg, or about 14 mg/kg, or about 15 mg/kg, or about 16 mg/kg, or about 18 mg/kg, or about 20 mg/kg, or about 25 mg/kg, or about 30 mg/kg, or about 35 mg/kg, or about 40 mg/kg, or about 45 mg/kg, or about 50 mg/kg, or about 60 mg/kg, or about 70 mg/kg, or about 80 mg/kg, or about 90 mg/kg, or about 100 mg/kg, when the mixture of a human proapolipoprotein and its corresponding mature apolipoprotein and at least one pharmaceutically acceptable carrier is administered to a subject in need thereof, preferably via parenteral administration. In various embodiments, the aforementioned compositions or pharmaceutical compositions are substantially free of one or more of phospholipids, lipids, trigycerides, glycerol, cholesterol or liposomes.

In some embodiments, the compositions and pharmaceutical compositions of the present invention can comprise a mixture of a human proapolipoprotein and a corresponding mature apolipoprotein, wherein the amount of mature apolipoprotein in the mixture is at least 25 mg to about 3,750 mg, or at least 50 mg, or at least 75 mg, or at least 100 mg, or at least 125 mg, or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,740 mg, or at least 3,000 mg, or at least 3,250 mg, or at least 3,500 mg, or at least 3,750 mg. In some embodiments, the compositions and pharmaceutical compositions of the present invention can comprise a mixture of a human proapolipoprotein and a corresponding mature apolipoprotein, wherein the amount of mature apolipoprotein in the mixture ranges from 25 mg to about 3,750 mg, or from 25 mg to about 3,250, or from about 25 mg to about 2,740 mg, or from about 100 mg to about 1,000 mg, or from about 100 mg to about 1,250 mg, or from about 100 mg to about 1,500 mg, or from about 100 mg to about 1,750 mg, or from about 100 mg to about 2,000 mg, or from about 100 mg to about 2,500 mg, or from about 100 mg to about 3,000 mg, or from about 100 mg to about 3.500 mg. In various embodiments, the aforementioned compositions or pharmaceutical compositions are substantially free of one or more of phospholipids, lipids, trigycerides, glycerol, cholesterol or liposomes.

In various embodiments, the compositions and pharmaceutical compositions can include a mixture of a proapolipoprotein and its corresponding mature apolipoprotein. In some embodiments, amounts of the combined mixture and of the mature apolipoprotein are expressed above in terms of their therapeutically effective amount. For example, a therapeutically effective amount of a mixture comprising a proapolipoprotein and its corresponding mature apolipoprotein in a composition or pharmaceutical composition can range from about 25 mg to about 5,000 mg, 100 mg to about 5,000 mg, or from about 200 mg to about 5,000 mg, or from about 300 mg to about 5,000 mg, or from about 400 mg to about 5,000 mg, or from about 500 mg to about 5,000 mg, or from about 600 mg to about 5,000 mg, or from about 700 mg to about 5,000 mg, or from about 800 mg to about 5,000 mg, or from about 900 mg to about 5,000 mg, or from about 1,000 mg to about 5,000 mg, or from about 1,250 mg to about 5,000 mg, or from about 1,500 mg to about 5,000 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg, or from about 25 mg to 8,350 mg.

In other embodiments, the mixture can be present in the composition or pharmaceutical composition in a therapeutically effective amount of at least 25 mg, or at least 50 mg, or at least 75 mg, or at least 100 mg, or at least 125 mg, or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,740 mg, or at least 3,000 mg, or at least 3,250 mg, or at least 3,500 mg, or at least 3,750 mg.

In some embodiments, the above recited amounts of the mixture or the mature apolipoprotein in the mixture present in the composition or pharmaceutical composition can be expressed as a ratio of proapolipoprotein to mature apolipoprotein expressed as a weight per weight percent basis (wt %). In one embodiment, the ratio of proapolipoprotein to its corresponding mature apolipoprotein in the mixture can range from 5:95 to 95:5 (wt %). In one illustrative example, a ratio of 5:95 to 95:5 of proapolipoprotein to its corresponding mature apolipoprotein would mean that in a pharmaceutical composition having 150 mg of the mixture, the amount of proapolipoprotein in the mixture can range from 7.5 mg to 142.5 mg. Conversely, the amount of mature apolipoprotein in the mixture can range from 142.5 mg to 7.5 mg. In other embodiments, the ratio of proapolipoprotein to its corresponding mature apolipoprotein can include: 20:80 to 80:20 (wt %); or 35:65 to 65:35 (wt %); or 40:60 to 60:40 (wt %); or 45:55 to 55:45 (wt %). Alternatively, the mixture can comprise a 50:50 ratio of proapolipoprotein to its corresponding mature apolipoprotein. In some embodiments, the ratio of proapolipoprotein to its corresponding mature apolipoprotein is 45:55 to 55:45 (wt %) and the amount of mature apolipoprotein in the mixture ranges from about 60 mg to about 120 mg. In another example, the ratio of proapolipoprotein to its corresponding mature apolipoprotein is 35:65 to 65:35 (wt %) and the amount of mature apolipoprotein in the mixture ranges from about 60 mg to about 120 mg. In one embodiment, the composition, pharmaceutical composition, injectable apolipoprotein composition or formulation comprises a mixture of a proapolipoprotein and its corresponding mature apolipoprotein, wherein the mixture comprises a ratio of proapolipoprotein to corresponding mature apolipoprotein ranging from about 35:65 to about 65:35 (wt %), and the amount of mature apolipoprotein in the mixture ranges from about 25 mg to about 3,250 mg. In one embodiment, the composition, pharmaceutical composition, injectable apolipoprotein composition or formulation comprises a mixture of a proapolipoprotein and its corresponding mature apolipoprotein, wherein the mixture comprises a ratio of proapolipoprotein to corresponding mature apolipoprotein ranging from about 35:65 to about 65:35 (wt %), and the combined amount of the mixture in the composition, pharmaceutical composition, injectable apolipoprotein composition or formulation ranges from about 25 mg to about 8,350 mg. In another embodiment, the composition, pharmaceutical composition, injectable apolipoprotein composition or formulation comprises a mixture of a proapolipoprotein and its corresponding mature apolipoprotein, wherein the mixture comprises a ratio of proapolipoprotein to corresponding mature apolipoprotein ranging from about 45:55 to about 55:45 (wt %), and the amount of mature apolipoprotein in the mixture ranges from about 25 mg to about 2,740 mg.

In some embodiments, the mixture of proapolipoprotein and its corresponding mature apoliporotein is substantially free of phospholipids, lipids, trigycerides, glycerol, cholesterol or liposomes, or combinations thereof. As used herein, substantially free of phospholipids, lipids, trigycerides, glycerol, cholesterol or liposomes, or combinations thereof can refer to a mixture of a proapolipoprotein and its corresponding mature apoliporotein that is not solubilized in or in contact with any one of phospholipids, lipids, trigycerides, glycerol, cholesterol or liposomes or combinations thereof, and if there are any amounts of any one or more of a phospholipid, a lipid, a triglyceride, glycerol, cholesterol, or a liposome, the amount of each is less than 5%, or less than 4%, or less than 3%, or less than 2%, or less than 1%, or less than 0.5%, or less than 0.1%, or less than 0.05%, or less than 0.01%, or 0% by weight of the mixture of the proapolipoprotein and its corresponding mature apoliporotein. In some embodiments, the mixture of a proapolipoprotein and its corresponding mature apoliporotein in the composition, pharmaceutical composition or formulation, is free of, i.e. contains 0% (wt %) of any one or more of a phospholipid, a lipid, a triglyceride, glycerol, cholesterol, a liposome, or combinations thereof on a weight per weight basis (wt %). In some embodiments, the mature apolipoprotein during purification, concentration and formulation into a composition, pharmaceutical composition or formulation is substantially free from a phospholipid, a triglyceride, a lipid, glycerol, cholesterol, a liposome, or combinations thereof.

In some embodiments of the present invention, the mixture of a proapolipoprotein and its corresponding mature apoliporotein exists in the composition or pharmaceutical composition as naked protein, or protein in solid form having a moisture content of less than 10%, or less than 5%, or less than 2%, less than 1%, less than 0.1%, or less than 0.01%. In another aspect, the present invention further provides a composition comprising a therapeutically effective amount of a mixture of a proapolipoprotein and its corresponding mature apolipoprotein. The composition may further comprise a pharmaceutically acceptable carrier. In some embodiments, the pharmaceutically acceptable carrier or combination of pharmaceutically acceptable carriers are substantially free of any one of a phospholipid, a lipid, a triglyceride, glycerol, cholesterol, or a liposome.

In one embodiment, the present invention provides a composition or pharmaceutical composition comprising, from about 125 mg to about 300 mg of the mixture of proapolipoprotein and corresponding mature apoliporotein, from about 0.1 to about 9 mg of NaCl, and from about 1.5 to about 0.9 mL of a suspending agent, wherein the ratio of proapolipoprotein to corresponding mature apoliporotein in the composition ranges from about 30:70 to 70:30 (wt %). In some embodiments, the mixture comprises human wild-type proapolipoprotein AI (SEQ ID NO: 1), and human wild-type mature apolipoprotein AI (SEQ ID NO: 2). In some embodiments, the mixture comprises human proapolipoprotein-AI-4WF (SEQ ID NO: 3), and human mature apolipoprotein-AI-4WF (SEQ ID NO: 4).

In one embodiment, the present invention provides a composition or pharmaceutical composition comprising, from about 25 mg to about 5,000 mg of the mixture of proapolipoprotein and corresponding mature apoliporotein, and from about 0.5 mL to about 40 mL of a suspending agent, wherein the ratio of proapolipoprotein to corresponding mature apoliporotein in the composition ranges from about 30:70 to 70:30 (wt %). In one embodiment, the present invention provides a composition or pharmaceutical composition comprising, from about 100 mg to about 5,000 mg of the mixture of proapolipoprotein and corresponding mature apoliporotein, and from about 1 mL to about 30 mL of a suspending agent, wherein the ratio of proapolipoprotein to corresponding mature apoliporotein in the composition ranges from about 30:70 to 70:30 (wt %). In one embodiment, the present invention provides a composition or pharmaceutical composition comprising, from about 100 mg to about 5,000 mg of the mixture of proapolipoprotein and corresponding mature apoliporotein, and from about 2 mL to about 20 mL of a suspending agent, wherein the ratio of proapolipoprotein to corresponding mature apoliporotein in the composition ranges from about 30:70 to 70:30 (wt %). In some of the aforementioned compositions or pharmaceutical compositions, the composition or pharmaceutical composition may optionally include from about 0.1 mg to about 90 mg of NaCl.

In some embodiments, the mixture comprises human wild-type proapolipoprotein-AI (SEQ ID NO: 1), and human wild-type mature apolipoprotein-AI (SEQ ID NO: 2). In other embodiments, the mixture comprises human proapolipoprotein-AI-4WF (SEQ ID NO: 3), and human mature apolipoprotein-AI-4WF (SEQ ID NO: 4). In various examples of the above embodiments, the aforementioned compositions or pharmaceutical compositions are substantially free of any one of a phospholipid, a lipid, a triglyceride, glycerol, cholesterol, and a liposome.

C. Formulations

A "dose amount" or "dose" as used herein, is generally equal to the dosage of the active ingredient which may be administered once per day, or once per week, or may be administered several times a day (e.g. the unit dose is a fraction of the desired daily dose), or may be administered several times per week (as a fraction of the desired weekly dose). For example, a therapeutically effective dose amount of 1,000 mg/week of the mixture of proapolipoprotein and its corresponding mature apolipoprotein may be administered as 1 dose of 1,000 mg, 2 doses of 500 mg each or 4 doses of 250 mg each, or 5 doses of 200 mg each per week. The term "unit dose" as used herein may be taken to indicate a discrete amount of the therapeutic composition which comprises a predetermined amount of the active mixture. The amount of the active mixture is generally equal to the dosage of the active mixture which may be administered once per day, or may be administered several times a day (e.g. the unit dose is a fraction of the desired daily dose), or once per week, or administered several times per week. The unit dose may also be taken to indicate the total daily dose, which may be administered once per day or may be administered as a convenient fraction of such a dose (e.g. the unit dose is the total daily dose which may be given in fractional increments, such as, for example, one-half or one-third or one-quarter or one-fifth the dosage).

As used herein, the term "daily dose amount" refers to the amount of the mixture (of a proapolipoprotein and its corresponding apolipoprotein) per day that is administered or prescribed to a patient. This amount can be administered in multiple unit doses or in a single unit dose, in a single time during the day or at multiple times during the day. As used herein, the term "weekly dose amount" refers to the amount of the mixture (of a proapolipoprotein and its corresponding apolipoprotein) that is administered or prescribed to a patient per week. This amount can be administered in multiple unit doses or in a single unit dose, in a single time during the week or at multiple times during the week.

A pharmaceutical composition of the present invention can be formulated to be compatible with its intended route of administration, as determined by those of skill in the art, and optionally, formulated under FDA-approved methods. Exemplary routes of administration of the pharmaceutical compositions, compositions and formulations can include: parenteral, e.g., subcutaneous, transmucosal, transdermal, intravenous, intramuscular, and intraperitoneal administration. The parenteral preparation can be enclosed in ampoules, disposable syringes or multiple dose, unit dose, or multiple unit dose vials or containers made of glass or plastic.

In some embodiments, the amount of the mixture of a proapolipoprotein and its corresponding mature apolipoprotein present in the composition, pharmaceutical composition or injectable apolipoprotein composition may be from about 0.01 mg/kg to about 100 mg/kg, from about 0.05 mg/kg to about 100 mg/kg, from about 0.1 mg/kg to about 100 mg/kg, from about 0.5 mg/kg to about 100 mg/kg, from about 1 mg/kg to about 100 mg/kg, or from about 10 mg/kg to about 100 mg/kg, or from about 5 mg/kg to about 50 mg/kg. In some embodiments, the amount of the mixture of a proapolipoprotein and its corresponding mature apolipoprotein present in the composition, pharmaceutical composition or injectable apolipoprotein composition provides a dose of about 0.01 mg/kg to about 90 mg/kg, or from about 0.01 mg/kg to about 70 mg/kg, or from about 0.01 mg/kg to about 50 mg/kg, or from about 0.01 mg/kg to about 25 mg/kg, or from about 0.01 mg/kg to about 20 mg/kg, or from about 0.01 mg/kg to about 10 mg/kg, or from about 0.01 mg/kg to about 5 mg/kg, or from about 0.01 mg/kg to about 1 mg/kg, or from about 0.01 mg/kg to about 0.1 mg/kg when the mixture of a human proapolipoprotein and its corresponding mature apolipoprotein and at least one pharmaceutically acceptable carrier is administered to a subject in need thereof, preferably via parenteral administration. In some embodiments, the therapeutically effective amount of the mixture of a proapolipoprotein and its corresponding mature apolipoprotein in the composition, pharmaceutical composition or injectable apolipoprotein composition may be from about 0.1 mg/kg to about 50 mg/kg. In some embodiments, the therapeutically effective amount of the mixture of a proapolipoprotein and its corresponding mature apolipoprotein in the composition, pharmaceutical composition or injectable apolipoprotein composition may be from about 1 mg/kg to about 50 mg/kg, or from about 5 mg/kg to about 50 mg/kg. In some embodiments, the amount of the mixture of a proapolipoprotein and its corresponding mature apolipoprotein in the composition, pharmaceutical composition or injectable apolipoprotein composition may be about 25 mg to about 5,000 mg, or from 100 mg to 1,500 mg. In various embodiments described above, the composition, pharmaceutical composition or injectable apolipoprotein composition is substantially free of any one or more of phospholipids, lipids, trigycerides, glycerol, cholesterol or liposomes.

In some embodiments, an exemplary daily dose amount of the mixture of a proapolipoprotein and its corresponding mature apolipoprotein is about 25 mg to about 5,000 mg, about 50 mg to about 5,000 mg, from about 100 mg to about 3,000 mg, from about 300 mg to about 1,500 mg, from about 500 mg to about 1,000 mg. In some embodiments, a therapeutically effective amount or a daily dose amount of the mixture of a proapolipoprotein and its corresponding mature apolipoprotein is about 25 mg to about 5,000 mg, from about 50 mg to about 5,000 mg, from about 100 mg to about 5,000 mg, from about 200 mg to about 5,000 mg, from about 250 mg to about 5,000 mg, from about 300 mg to about 5,000 mg, from about 400 mg to about 5,000 mg, from 450 mg to about 5,000 mg, from 500 mg to about 5,000 mg, from about 25 mg to about 3,000, from about 100 mg to about 3,000 mg, from about 200 mg, to about 3,000 mg, from about 250 mg to about 3,000 mg, from about 300 mg to about 3,000 mg, from about 400 mg to about 3,000 mg, from 450 mg to about 3,000 mg, from about 100 mg to about 1,000 mg, from about 200 mg to about 1,000 mg, from about 250 mg to about 1,000 mg, from about 300 mg to about 1,000 mg, from about 400 mg to about 1,000 mg, from 500 mg to about 1,000 mg, from about 600 mg to about 1,000 mg, or from 500 mg to about 1,200 mg.

In some embodiments, a therapeutically effective amount or daily dose amount of the mixture of a proapolipoprotein and its corresponding mature apolipoprotein in a pharmaceutical composition is from about 50 mg to about 1,500 mg, or from about 100 mg to about 1,250 mg.

The above recited exemplary daily doses may be administered as a single daily dose, or may be divided into several doses administered throughout the day, for example, 1 to 5 doses, or two or three doses per day. In some embodiments, the amount of a mixture of a proapolipoprotein and its corresponding mature apolipoprotein in a pharmaceutical composition ranges from about 25 mg to about 5,000 mg. In some embodiments, the amount of a mixture of a proapolipoprotein and its corresponding mature apolipoprotein in a pharmaceutical composition ranges from about 100 mg to about 3,000 mg. In some embodiments, the amount of a mixture of a proapolipoprotein and its corresponding mature apolipoprotein in a pharmaceutical composition ranges from about 200 mg to about 2,000 mg. In some embodiments, the amount of a mixture of a proapolipoprotein and its corresponding mature apolipoprotein in a pharmaceutical composition ranges from about 500 mg to about 1,500 mg. In some embodiments, the combined amount of a proapolipoprotein and its corresponding mature apolipoprotein in a pharmaceutical composition administered to a subject is at least 25 mg. In some embodiments, the combined amount of a proapolipoprotein and its corresponding mature apolipoprotein in a pharmaceutical composition administered to a subject is at least 100 mg. In some embodiments, the combined amount of a proapolipoprotein and its corresponding mature apolipoprotein in a pharmaceutical composition administered to a subject is at least 150 mg. In some embodiments, the combined amount of a proapolipoprotein and its corresponding mature apolipoprotein in a pharmaceutical composition administered to a subject is at least 200 mg. In some embodiments, the combined amount of a proapolipoprotein and its corresponding mature apolipoprotein in a pharmaceutical composition administered to a subject is at least 250 mg. In some embodiments, the combined amount of a proapolipoprotein and its corresponding mature apolipoprotein in a pharmaceutical composition administered to a subject is at least 300 mg. In some embodiments, the combined amount of a proapolipoprotein and its corresponding mature apolipoprotein in a pharmaceutical composition administered to a subject is at least 400 mg. In some embodiments, the combined amount of a proapolipoprotein and its corresponding mature apolipoprotein in the pharmaceutical composition administered to a subject is at least 500 mg. In some embodiments, the combined amount of a proapolipoprotein and its corresponding mature apolipoprotein in a pharmaceutical composition administered to a subject is at least 750 mg. In some embodiments, the combined amount of a proapolipoprotein and its corresponding mature apolipoprotein in a pharmaceutical composition administered to a subject is at least 1,000 mg. In some embodiments, the combined amount of a proapolipoprotein and its corresponding mature apolipoprotein in a pharmaceutical composition administered to a subject is at least 1,500 mg. In some embodiments, the combined amount of a proapolipoprotein and its corresponding mature apolipoprotein in a pharmaceutical composition administered to a subject is at least 3,000 mg.

In some embodiments, the amount of a mixture of a proapolipoprotein and its corresponding mature apolipoprotein may be from about 0.01 mg/kg/day to about 100 mg/kg/day, from about 0.05 mg/kg/day to about 100 mg/kg/day, from about 0.1 mg/kg/day to about 100 mg/kg/day, from about 0.5 mg/kg/day to about 100 mg/kg/day, from about 1 mg/kg/day to about 100 mg/kg/day, or from about 10 mg/kg/day to about 100 mg/kg/day. In some embodiments, the amount of a mixture of a proapolipoprotein and its corresponding mature apolipoprotein may be from about 0.01 mg/kg/day to about 90 mg/kg/day, or from about 0.01 mg/kg/day to about 70 mg/kg/day, or from about 0.01 mg/kg/day to about 50 mg/kg/day, or from about 0.01 mg/kg/day to about 25 mg/kg/day, or from about 0.01 mg/kg/day to about 20 mg/kg/day, or from about 0.01 mg/kg/day to about 10 mg/kg/day, or from about 0.01 mg/kg/day to about 5 mg/kg/day, or from about 0.01 mg/kg/day to about 1 mg/kg/day, or from about 0.01 mg/kg/day to about 0.1 mg/kg/day.

In some embodiments, a therapeutically effective amount or a daily and/or weekly amount of a mixture of a proapolipoprotein and its corresponding mature apolipoprotein in a pharmaceutical composition may be from about 0.1 mg/kg to about 50 mg/kg. In some embodiments, the amount of the mixture of a proapolipoprotein and its corresponding mature apolipoprotein in a pharmaceutical composition may be from about 1 mg/kg to about 25 mg/kg. In some embodiments, a therapeutically effective amount or a daily dose and/or weekly dose amount of a mixture of a proapolipoprotein and its corresponding mature apolipoprotein in a pharmaceutical composition may be from about 25 mg to 5,000 mg, or from about 500 mg to about 1000 mg, administered per day, or per week, to a subject in need thereof.

In some embodiments, the therapeutically effective amount or daily dose amount of the mixture of a proapolipoprotein and its corresponding mature apolipoprotein is about 25 mg to about 5,000 mg, 100 mg to about 5,000 mg, or from about 200 mg to about 5,000 mg, or from about 300 mg to about 5,000 mg, or from about 400 mg to about 5,000 mg, or from about 500 mg to about 5,000 mg, or from about 600 mg to about 5,000 mg, or from about 700 mg to about 5,000 mg, or from about 800 mg to about 5,000 mg, or from about 900 mg to about 5,000 mg, or from about 1,000 mg to about 5,000 mg, or from about 1,250 mg to about 5,000 mg, or from about 1,500 mg to about 5,000 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg. In some embodiments, therapeutically effective amount or daily dose amount of the mixture of a proapolipoprotein and its corresponding mature apolipoprotein in a pharmaceutical composition is from about 100 mg to about 2,000 mg, or from about 500 mg to about 1,500 mg. This dose may be administered as a single daily dose, or may be divided into several doses administered throughout the day, for example, 1 to 5 doses, or two or three doses per day. In some embodiments, the mixture of a proapolipoprotein and its corresponding mature apolipoprotein in the pharmaceutical composition is from about 25 mg to about 5,000 mg. In some embodiments, the mixture of a proapolipoprotein and its corresponding mature apolipoprotein in the pharmaceutical composition is from about 100 mg to about 3,000 mg. In some embodiments, the mixture of a proapolipoprotein and its corresponding mature apolipoprotein in the pharmaceutical composition is from about 200 mg to about 1,500 mg. In some embodiments, the mixture of a proapolipoprotein and its corresponding mature apolipoprotein in the pharmaceutical composition administered to the subject from about 300 mg to about 1,000 mg.

In some embodiments, the combined amount of a proapolipoprotein and its corresponding mature apolipoprotein in the pharmaceutical composition administered to the subject is at least 25 mg, or at least 50 mg, or at least 75 mg, or at least 100 mg, or at least 125 mg, or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,750 mg, or at least 3,000 mg, or at least 3,250 mg, or at least 3,500 mg, or at least 3,750 mg, or at least 8,350 mg.

In some embodiments, the therapeutically effective amount of the mixture of a proapolipoprotein and its corresponding mature apolipoprotein in the pharmaceutical composition may be from about 0.01 mg/kg/week to about 100 mg/kg/week, from about 0.05 mg/kg/week to about 100 mg/kg/week, from about 0.1 mg/kg/week to about 100 mg/kg/week, from about 0.5 mg/kg/week to about 100 mg/kg/week, from about 1 mg/kg/week to about 100 mg/kg/week, or from about 10 mg/kg/week to about 100 mg/kg/week. In some embodiments, the amount of the mixture of a proapolipoprotein and its corresponding mature apolipoprotein may be from about 0.01 mg/kg/week to about 90 mg/kg/week, or from about 0.01 mg/kg/week to about 70 mg/kg/week, or from about 0.01 mg/kg/week to about 50 mg/kg/week, or from about 0.01 mg/kg/week to about 25 mg/kg/week, or from about 0.01 mg/kg/week to about 20 mg/kg/week, or from about 0.01 mg/kg/week to about 10 mg/kg/week, or from about 0.01 mg/kg/week to about 5 mg/kg/week, or from about 0.01 mg/kg/week to about 1 mg/kg/week, or from about 0.01 mg/kg/week to about 0.1 mg/kg/week. In some embodiments, the amount of the mixture of a proapolipoprotein and its corresponding mature apolipoprotein in the pharmaceutical composition may be from about 0.1 mg/kg/week to about 50 mg/kg/week. In some embodiments, the amount of the mixture of a proapolipoprotein and its corresponding mature apolipoprotein in the pharmaceutical composition may be from about 1 mg/kg/week to about 25 mg/kg/week.

In some embodiments, the dosage may be 25 mg/week to 5,000 mg/week, or 100 mg/week to 3,000 mg/week. The therapeutically effective amount or weekly dose amount of the mixture of a proapolipoprotein and its corresponding mature apolipoprotein in the pharmaceutical composition can range from about 25 mg to about 5,000 mg, 100 mg to about 5,000 mg, or from about 200 mg to about 5,000 mg, or from about 300 mg to about 5,000 mg, or from about 400 mg to about 5,000 mg, or from about 500 mg to about 5,000 mg, or from about 600 mg to about 5,000 mg, or from about 700 mg to about 5,000 mg, or from about 800 mg to about 5,000 mg, or from about 900 mg to about 5,000 mg, or from about 1,000 mg to about 5,000 mg, or from about 1,250 mg to about 5,000 mg, or from about 1,500 mg to about 5,000 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg. In some embodiments, the dosage may be 25 mg/week to about 8,350 mg/week.

In some embodiments, the therapeutically effective amount or weekly dose amount of the mixture of a proapolipoprotein and its corresponding mature apolipoprotein in the pharmaceutical composition is from about 25 mg to about 5,000 mg, or from about 100 mg to about 1,500 mg, or 25 mg to about 8,350 mg. This weekly dose may be administered as a single weekly dose, or may be divided into several subdoses administered throughout the week, for example, 1 to 5 doses per week, or one, two or three doses per week.

In some embodiments, the mixture of a proapolipoprotein and its corresponding mature apolipoprotein in a pharmaceutical composition is administered to the subject in an amount from about 25 mg to about 5,000 mg per dose. In some embodiments, the mixture of a proapolipoprotein and its corresponding mature apolipoprotein in the pharmaceutical composition administered to the subject from about 100 mg to about 3,000 mg per dose. In some embodiments, the mixture of a proapolipoprotein and its corresponding mature apolipoprotein in the pharmaceutical composition administered to the subject from about 200 mg to about 1,500 mg per dose. In some embodiments, the mixture of a proapolipoprotein and its corresponding mature apolipoprotein in the pharmaceutical composition administered to the subject is from about 300 mg to about 1,250 mg per dose. In some embodiments, the combined amount of a proapolipoprotein and its corresponding mature apolipoprotein in the pharmaceutical composition administered to the subject is at least 100 mg. In some embodiments, the combined amount of a proapolipoprotein and its corresponding mature apolipoprotein in the pharmaceutical composition administered to the subject is at least 150 mg. In some embodiments, the combined amount of a proapolipoprotein and its corresponding mature apolipoprotein in the pharmaceutical composition administered to the subject is at least 200 mg. In some embodiments, the combined amount of a proapolipoprotein and its corresponding mature apolipoprotein in the pharmaceutical composition administered to the subject is at least 250 mg. In some embodiments, the combined amount of a proapolipoprotein and its corresponding mature apolipoprotein in the pharmaceutical composition administered to the subject is at least 300 mg. In some embodiments, the combined amount of a proapolipoprotein and its corresponding mature apolipoprotein in the pharmaceutical composition administered to the subject is at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,750 mg, or at least 3,000 mg, or at least 3,250 mg, or at least 3,500 mg, or at least 3,750 mg.

In some embodiments, the pharmaceutical composition or composition or formulation, e.g. injectable apolipoprotein composition comprises a mixture of a proapolipoprotein and its corresponding mature apolipoprotein, wherein the combined amount of proapolipoprotein and its corresponding mature apolipoprotein is from about 25 mg to about 5,000 mg.

In some embodiments, the pharmaceutical composition or composition or formulation, e.g. injectable apolipoprotein composition comprises a mixture of a proapolipoprotein and its corresponding mature apolipoprotein, wherein the combined amount of proapolipoprotein and its corresponding mature apolipoprotein is from about 100 mg to about 5,000 mg.

In some embodiments, the pharmaceutical composition or composition or formulation, e.g. injectable apolipoprotein composition comprises a mixture of a proapolipoprotein and its corresponding mature apolipoprotein, wherein the combined amount of proapolipoprotein and its corresponding mature apolipoprotein is from about 200 mg to about 5,000 mg.

In some embodiments, the pharmaceutical composition or composition or formulation, e.g. injectable apolipoprotein composition comprises a mixture of a proapolipoprotein and its corresponding mature apolipoprotein, wherein the combined amount of proapolipoprotein and its corresponding mature apolipoprotein is from about 300 mg to about 5,000 mg.

In some embodiments, the pharmaceutical composition or composition or formulation, e.g. injectable apolipoprotein composition comprises a mixture of a proapolipoprotein and its corresponding mature apolipoprotein, wherein the combined amount of proapolipoprotein and its corresponding mature apolipoprotein is from about 25 mg to about 8,350 mg.

In some embodiments, the pharmaceutical composition or composition or formulation, e.g. injectable apolipoprotein composition comprises a mixture of a proapolipoprotein and its corresponding mature apolipoprotein, wherein the combined amount of proapolipoprotein and its corresponding mature apolipoprotein is from about 500 mg to about 5,000 mg.

In some embodiments, the pharmaceutical composition or composition or formulation, e.g. injectable apolipoprotein composition comprises a mixture of a proapolipoprotein and its corresponding mature apolipoprotein, wherein the combined amount of proapolipoprotein and its corresponding mature apolipoprotein is from about 600 mg to about 5,000 mg.

In some embodiments, the pharmaceutical composition or composition or formulation, e.g. an injectable apolipoprotein composition comprises a mixture of a proapolipoprotein and its corresponding mature apolipoprotein, wherein the combined amount of proapolipoprotein and its corresponding mature apolipoprotein is from about 700 mg to about 5,000 mg.

In some embodiments, the pharmaceutical composition or composition or formulation, e.g. an injectable apolipoprotein composition comprises a mixture of a proapolipoprotein and its corresponding mature apolipoprotein, wherein the combined amount of proapolipoprotein and its corresponding mature apolipoprotein is from about 800 mg to about 5,000 mg.

In some embodiments, the pharmaceutical composition or composition or formulation, e.g. an injectable apolipoprotein composition comprises a mixture of a proapolipoprotein and its corresponding mature apolipoprotein, wherein the combined amount of proapolipoprotein and its corresponding mature apolipoprotein is from about 900 mg to about 5,000 mg.

In some embodiments, the pharmaceutical composition or composition or formulation, e.g. an injectable apolipoprotein composition comprises a mixture of a proapolipoprotein and its corresponding mature apolipoprotein, wherein the combined amount of proapolipoprotein and its corresponding mature apolipoprotein is from about 1,000 mg to about 5,000 mg.

In some embodiments, the pharmaceutical composition or composition or formulation, e.g. an injectable apolipoprotein composition comprises a mixture of a proapolipoprotein and its corresponding mature apolipoprotein, wherein the combined amount of proapolipoprotein and its corresponding mature apolipoprotein is from about 1,250 mg to about 5,000 mg.

In some embodiments, the pharmaceutical composition or composition or formulation, e.g. an injectable apolipoprotein composition comprises a mixture of a proapolipoprotein and its corresponding mature apolipoprotein, wherein the combined amount of proapolipoprotein and its corresponding mature apolipoprotein is from about 1,500 mg to about 5,000 mg.

In some embodiments, the pharmaceutical composition or composition or formulation, e.g. an injectable apolipoprotein composition comprises a mixture of a proapolipoprotein and its corresponding mature apolipoprotein, wherein the combined amount of proapolipoprotein and its corresponding mature apolipoprotein is from about 25 mg to about 8,350 mg.

In some embodiments, the composition comprises a pharmaceutically acceptable excipient, for example a liquid excipient, for example a solubulizer, a suspending agent, an isotonic agent, a buffering agent or a pH adjusting agent. In some embodiments, the composition is suitable for parenteral administration, for example, in admixture with a liquid excipient useful in parenteral administration, e.g. intravenous, intradermal, intraperitoneal, intramuscular, subcutaneous or combinations thereof. In some embodiments, the composition is a solid form of protein, for example a powder, for example a lyophilized protein sample. In some embodiments, illustrative liquid excipients can include one or more solutions or suspensions used for intravenous, intradermal, intramuscular, intraperitoneal, or subcutaneous application, which can include one or more of the following components: a sterile diluent such as sterile grade water for injection, physiological saline solution (e.g., phosphate buffered saline (PBS)); antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid (EDTA); buffers such as acetates, citrates or phosphates and agents for the adjustment of pH, or tonicity such as sodium chloride or dextrose. In many cases, it will be preferable to include isotonic agents, for example, sugars, polyalcohols such as mannitol or sorbitol, and sodium chloride in the composition. Prolonged administration of the injectable apolipoprotein formulations can be brought about by including an agent that delays absorption. Such agents include, for example, aluminum monostearate and gelatin. The parenteral preparation can be enclosed in ampoules, disposable syringes or multiple dose vials or containers made of glass or plastic.

The liquid excipient, diluent, vehicle or carrier can also contain other pharmaceutically-acceptable excipients for modifying or maintaining the pH, osmolarity, viscosity, clarity, color, sterility, stability, rate of dissolution, or odor of the formulation. Similarly, the liquid excipient may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct injection.

In some embodiments, the composition, or pharmaceutical composition is formulated for parenteral administration. In some embodiments, various pharmaceutical compositions and compositions provided above, provide a mixture of a proapolipoprotein and its corresponding mature apolipoprotein and a liquid excipient in a volume of about 0.5 to about 50 mL, or from about 0.5 mL to about 45 mL, or from about 0.5 mL to about 40 mL, or from about 0.5 mL to about 35 mL, or from about 0.5 mL to about 30 mL, or from about 0.5 mL to about 25 mL, or from about 0.5 mL to about 20 mL, or from about 0.5 mL to about 15 mL, or from about 0.5 mL to about 10 mL, each of these pharmaceutical compositions and compositions being suitable for parenteral administration into the patient in need thereof. In some embodiments, the pharmaceutical compositions and compositions provided above, the mixture of proapolipoprotein and its corresponding mature apolipoprotein is solubulized in a liquid excipient wherein the final composition, or pharmaceutical composition or formulation has a volume of about 0.5 to about 2.5 mL. In some embodiments, the mixture of proapolipoprotein and its corresponding mature apolipoprotein is in admixture with a pharmaceutically acceptable liquid excipient, wherein the composition, pharmaceutical composition or formulation has a volume of about 0.5 mL to about 2.5 mL, or about 0.5 mL to about 2.0 mL, or about 0.5 mL to about 1.5 mL, or about 0.5 mL to about 1.0 mL. In some embodiments, the mixture of proapolipoprotein and its corresponding mature apolipoprotein is in admixture with a pharmaceutically acceptable liquid excipient, wherein the composition, pharmaceutical composition or formulation has a volume of about 0.5 mL to about 40 mL, or about 1 mL to about 30 mL,
or about 0.5 mL to about 25 mL, or about 0.5 mL to about 20 mL, or about 0.5 mL to about 10 mL.

In some embodiments, the present invention provides an injectable apolipoprotein composition comprising: a) mixture of proapolipoprotein and a corresponding mature apolipoprotein, and b) at least one pharmaceutically acceptable excipient. As used herein, an injectable apolipoprotein composition can include a liquid excipient in admixture with a mixture of a proapolipoprotein and its corresponding mature apolipoprotein. In some embodiments, the injectable apolipoprotein formulation is intended to be administered to a patient in need thereof, for example, an injectable form, either intravenously, intramuscularly, intraperitoneally, or subcutaneously. In some embodiments, the injectable apolipoprotein composition is sterile, for example, prior to the addition of a liquid excipient, or sterile after the addition of a liquid excipient, or both. In some embodiments, the injectable apolipoprotein composition is chemically stable upon prolonged storage, i.e. the injectable apolipoprotein composition has less than 20% loss in reverse cholesterol activity as measured using the exemplified reverse cholesterol activity assays herein, for example, less than 10% or less than 5%, or less than 1% or less than 0.1% reverse cholesterol activity when stored for a period ranging from about 6 hours, or 12 hours, or 24 hours, or 36 hours, or 48 hours, or 72 hours, or 1 week, or 2 weeks, or 3 weeks, or 4 weeks or about 2 months, or about 3 months, or about 6 months, or about 12 months, when stored at about −70° C., or about −20° C., or about −4° C., or about 4° C., or about 21° C., or about 37° C.

In some embodiments, the injectable apolipoprotein formulation comprises an amount of the mixture of proapolipoprotein to corresponding mature apolipoprotein from about 25 mg to about 5,000 mg, wherein the ratio of proapolipoprotein to corresponding mature apolipoprotein in the mixture ranges from about 5:95 to about 95:5 (wt %), or from about 20:80 to about 80:20 (wt %), or from about 35:65 to about 65:35 (wt %), or from about 40:60 to about 60:40 (wt %), or from about 45:55 to about 55:45 (wt %). In some embodiments, the ratio of proapolipoprotein to corresponding mature apolipoprotein in the mixture is about 50:50 (wt %).

In some embodiments, the injectable apolipoprotein formulation comprises is at least 25 mg, or at least 50 mg, or at least 75 mg, or at least 100 mg, or at least 125 mg, or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,740 mg, or at least 3,000 mg, or at least 3,250 mg, or at least 3,500 mg, or at least 3,750 mg or at least 2,750 mg, or at least 3,000 mg, or at least 3,250 mg or at least 3,000 mg, or at least 3,250 mg, or at least 3,500 mg, or at least 4,000 mg, or at least 4,500 mg, or at least 5,000 mg, or at least 6,000 mg, or at least 8,350 mg of the mature apolipoprotein in the mixture of proapoliporotein and corresponding mature apolipoprotein. In some embodiments, the injectable apolipoprotein composition comprises at least about 50 mg, or at least about 100 mg, or at least about 150 mg, or at least about 200 mg, or at least about 250 mg, or at least about 300 mg, or at least about 400 mg of a mixture of proapolipoprotein and its corresponding mature apolipoprotein.

In some embodiments, the injectable apolipoprotein composition comprises a mixture of proapolipoprotein and its corresponding mature apolipoprotein in an amount ranging from about 25 mg to about 5,000 mg, 100 mg to about 5,000 mg, or from about 200 mg to about 5,000 mg, or from about 300 mg to about 5,000 mg, or from about 400 mg to about 5,000 mg, or from about 500 mg to about 5,000 mg, or from about 600 mg to about 5,000 mg, or from about 700 mg to about 5,000 mg, or from about 800 mg to about 5,000 mg, or from about 900 mg to about 5,000 mg, or from about 1,000 mg to about 5,000 mg, or from about 1,250 mg to about 5,000 mg, or from about 1,500 mg to about 5,000 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg.

In some embodiments, the injectable apolipoprotein composition comprises a mixture of a proapolipoprotein and its corresponding mature apolipoprotein, wherein the amount of the mature apolipoprotein in the mixture is at least 25 mg, or at least 50 mg, or at least 75 mg, or at least 100 mg, or at least 125 mg, or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,740 mg, or at least 3,000 mg, or at least 3,250 mg, or at least 3,500 mg, or at least 3,750 mg.

In some embodiments, the injectable apolipoprotein composition includes from about 25 mg to about 5,000 mg of the mixture of proapolipoprotein and corresponding mature apoliporetin, and from about 0.5 mL to about 30 mL of a suspending agent, wherein the ratio of proapoliporetin to corresponding mature apoliporetin in the composition ranges from about 30:70 to 70:30 (wt %). In one embodiment, the present invention provides an injectable apolipoprotein composition comprising, from about 200 mg to about 3,500 mg of the mixture of proapolipoprotein and corresponding mature apoliporetin, and from about 0.5 mL to about 30 mL of a suspending agent, wherein the ratio of proapolipoprotein to corresponding mature apoliporetin in the composition ranges from about 30:70 to 70:30 (wt %). In one embodiment, the present invention provides an injectable apolipoprotein composition comprising, from about 500 mg to about 2,000 mg of the mixture of proapolipoprotein and corresponding mature apoliporetin, and from about 0.5 mL to about 15 mL of a suspending agent, wherein the ratio of proapolipoprotein to corresponding mature apoliporetin in the composition ranges from about 30:70 to 70:30 (wt %).

In some of the aforementioned injectable apolipoprotein compositions, the composition may optionally include from about 0.1 to about 90 mg of NaCl.

In some of the aforementioned injectable apolipoprotein compositions, the compositions are substantially free from any one of a phospholipid, a triglyceride, a lipid, cholesterol, glycerol, a liposome, or combinations thereof.

In some of the aforementioned injectable apolipoprotein compositions, the mixture comprises human wild-type proapolipoprotein AI (SEQ ID NO: 1), and human wild-type mature apolipoprotein AI (SEQ ID NO: 2). In other embodiments, the mixture comprises human proapolipoprotein AI-4WF (SEQ ID NO: 3), and human mature apolipoprotein AI-4WF (SEQ ID NO: 4). In some embodiments, the injectable apolipoprotein compositions of the present invention can be: liquid, or freeze-dried or lyophilized preparations of mixtures of proapolipoprotein and its corresponding mature apolipoprotein, which can be can be reconstituted, dialyzed, rehydrated with phosphate buffered saline, a physiological saline solution or some other appropriate pharmaceutically acceptable diluent, solubulizer, suspending agent, isotonic agent, buffering agent, or pH adjusting agent prior to storage or administration or injection to the patient.

In one embodiment, the invention provides a method for preparing a stable apolipoprotein injectable composition. The method includes combining a) a mixture of proapolipoprotein and a corresponding mature apolipoprotein, the mixture having a ratio of proapolipoprotein to corresponding apolipoprotein ranging from about 5:95 to about 95:5 (w$_r$%), and b) at least one pharmaceutically acceptable excipient selected from the group consisting of a solubilizer, a suspending agent, an isotonic agent, a buffering agent, and a pH adjusting agent.

D. Methods of Making Concentrated Apolipoproteins

One of the major draw backs to the treatment of apolipoprotein insufficiency, (such as cardiovascular disorders, in particular, atherosclerosis and inflammatory diseases such as diabetes and metabolic syndrome) with an apolipoprotein, is the chemical and biological fragility of the apolipoprotein. Previous trials involving administration of an apolipoprotein or mimetic thereof have all required administration of the apolipoprotein complexed with a phospholipid or liposome. The inherent problems associated with such administration, include the necessity, that stability is achieved by diluting the concentration of apolipoprotein with lipid complexes such as 1-Palmitoyl-2-oleoyl-sn-glycero-3-phosphocholine (POPC). Such dilution required excessively large volumes of the pharmaceutical composition as to require lengthy infusions and large volume doses, impacting patient compliance and administration success. In fact, it has been common practice in the art of apolipoprotein synthesis, whether eukaryotic or recombinant production, that the concentration of apolipoprotein has not exceeded 0.1-10 mg/mL, and even then, the stability of the apolipoprotein is ensured only after the addition of a phospholipid or lipidic or liposome agent. With these problems to be solved, the inventors of the present invention have spent considerable effort in identifying methods to increase the concentration of a mature apolipoprotein in solution, for example, the apolipoproteins having the amino acid of SEQ ID NO: 2 and SEQ ID NO: 4 without degradation and loss of biological activity. The inventors have unexpectedly and surprisingly found that if the mature apolipoprotein is concentrated with its corresponding proapolipoprotein, the mature apolipoprotein can be concentrated 10-40 times above the concentration at which the mature apolipoprotein becomes denatured, unfolded, and crashes out of solution when compared to the concentration of a pure mature apolipoprotein composition.

In some embodiments, the present invention provides a method for concentrating a mature apolipoprotein in solution, the method comprising: (a) providing a first solution comprising a mixture of a proapolipoprotein and a corresponding mature apolipoprotein, (b) concentrating the first solution to a first concentrated volume; and (c) adding a second solution comprising the mature apolipoprotein to the first concentrated volume to form a second concentrated volume. In some embodiments, steps (b) and (c) can be repeated until a desired concentration of the mature apolipoprotein is achieved in a final concentrated volume. In some embodiments the present method provides a desired concentration of a mixture comprising a proapolipoprotein and its corresponding mature apolipoprotein in the final concentrated volume ranging from about 50 mg/mL to about 400 mg/mL. In some embodiments, the first solution and the second solution are the same. The present method for concentrating a mature apolipoprotein can be used to concentrate many apolipoproteins, for example, the proapolipoprotein and its corresponding mature apolipoprotein to be concentrated can include apolipoprotein AI, apolipoprotein AII, apolipoprotein AIV, apolipoprotein AV, apolipoprotein B, apolipoprotein E, apolipoprotein AI-Milano, apolipoprotein AI-Paris, apolipoprotein AI-Marburg, apolipoprotein 4WF, or combinations thereof. In some embodiments, the mixture of pro and mature apolipoproteins to be concentrated can include, mammalian apolipoproteins, for example, human apolipoproteins, for example, human wild-type apolipoprotein-AI and apolipoprotein-4WF as provided by SEQ ID NO: 1-2 and 3-4 respectively.

As noted above, the present methods to increase the solubility and concentration of mature apolipoproteins and their corresponding proapolipoproteins does not rely on the prior methods for stabilizing the structure of the apolipoproteins with phospholipids. As such the method for increasing the concentration and solubility of mature apolipoproteins do not require admixture of the proapolipoprotein and corresponding mature apolipoprotein with a phospholipid, a triglyceride, a lipid, cholesterol, glycerol, a liposome, or combinations thereof.

In various embodiments, the methods disclosed herein for the concentration and increase in solubulization of mature apolipoproteins recited herein can increase the concentration of the apolipoproteins by a factor of 10-50 times as compared to concentrating the mature apolipoprotein alone. Concentration of mixtures of proapolipoproteins and their corresponding mature apolipoproteins to levels of about 20 mg/mL to about 50 mg/mL to about 400 mg/mL can be achieved in relatively small volumes, for example, in less than 50 mL, or in 40 mL or less, or in 30 mL or less, in 25 mL or less, in 20 mL or less, in 15 mL or less, in 10 mL or less, or in 5 mL or less, or in 2.5 mL or less, or 2.0 mL or less, or 1.5 mL or less or 1.0 mL or less. In some embodiments, the concentrated mixtures can be attained in volumes ranging from about 0.5 mL to about 30 mL or from about 0.5 mL to about 20 mL using the methods disclosed herein. These small volumes, 0.5-40 mL of highly concentrated mixtures of mature apolipoprotein and their corresponding proapolipoproteins (at ratios of 5:95 to 95:5, or from about 20:80 to about 80:20, or from about 35:65 to about 65:35, or from about 40:60 to about 60:40, or from about 45:55 to about 55:45 or about 50:50 (wt %)) permit injection of concentrated apolipoprotein compositions substantially free of any one of a phospholipid, a triglyceride, a lipid, cholesterol, glycerol, a liposome, or combinations thereof, at therapeutically effective amounts (for example, 25 mg to 5,000 mg) via intravenous, subcutaneous, intramuscular, intraperitoneally and transdermal routes previously unattainable. Such dosing opportunities enable facile administration by medical practitioners and even the patient themselves, thereby obviating lengthy infusion protocols, infrequent dosing, difficulty in patient compliance, added expense in medical supervision, and the need for possible allergy inducing lipid complexing reagents.

When a "combination therapy" is employed, an effective amount can be achieved using a first amount of a mixture of a proapolipoprotein and its corresponding mature apolipoprotein as described herein or a pharmaceutically acceptable salt, solvate (e.g., hydrate), thereof and a second amount of an additional suitable therapeutic agent (e.g., an agent to treat an associated comorbidity, e.g. hypertension, arrhythmia, allergy, infection, ischemia, pain, or inflammation of the tissue, organ or blood vessel leading to the diseases and disorders described herein). In other embodiments, when a "combination therapy" is employed, an effective amount can be achieved using a first amount of a mixture of a proapolipoprotein and its corresponding mature apolipoprotein described herein or a pharmaceutically acceptable salt, solvate (e.g., hydrate), thereof and a second amount of an additional suitable therapeutic agent (e.g., an agent to treat an associated comorbidity, e.g. hypertension, arrhythmia, allergy, infection, ischemia, pain, or inflammation of the tissue, organ or blood vessel leading to the diseases and disorders described herein).

In some embodiments of the present invention, the mixture of a proapolipoprotein and its corresponding mature apolipoprotein and, in some embodiments, one or more additional therapeutic agents are each administered in an effective amount (i.e., each in an amount which would be therapeutically effective if administered alone). In some embodiments of the present invention, the mixture of a proapolipoprotein and its corresponding mature apolipoprotein, and, in some embodiments, one or more additional therapeutic agents are each administered in an effective amount (i.e., each in an amount which would be therapeutically effective if administered alone). in other embodiments, the mixture of a proapolipoprotein and its corresponding mature apolipoprotein and optionally, the one or more additional therapeutic agents, are each administered in an amount which alone does not provide a therapeutic effect (a sub-therapeutic dose). In other embodiments, the mixture of a proapolipoprotein and its corresponding mature apolipoprotein and optionally, the one or more additional therapeutic agents, are each administered in an amount which alone does not provide a therapeutic effect (a sub-therapeutic dose). In yet other embodiments, the mixture of a proapolipoprotein and its corresponding mature apolipoprotein can be administered in a therapeutically effective amount, while the one or more additional therapeutic agents are administered in a sub-therapeutic dose. In other embodiments, the mixture of a proapolipoprotein and its corresponding mature apolipoprotein can be administered in a therapeutically effective amount, while the one or more additional therapeutic agents are administered in a sub-therapeutic dose. In still other embodiments, the mixture of a proapolipoprotein and its corresponding mature apolipoprotein can be administered in a sub-therapeutic dose, while the one or more additional therapeutic agents, for example, a suitable dyslipidemia or cardiovascular therapeutic agent (e.g. a statin, an anti-hypertensive and the like) is administered in a therapeutically effective amount. In still further embodiments, the mixture of a proapolipoprotein and its corresponding mature apolipoprotein can be administered in a sub-therapeutic dose, while the one or more additional therapeutic agents, for example, a suitable dyslipidemia or cardiovascular therapeutic agent is administered in a therapeutically effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the active agents (i.e. a mixture of a proapolipoprotein and its corresponding mature apolipoprotein, and an additional active agent) in an essentially simultaneous manner, such as in a single pharmaceutical composition, for example, an injectable solution having a fixed ratio of first and second amounts, or in multiple, separate capsules solutions for injections for each. In some embodiments, co-administration encompasses administration of the first and second amounts of the active agents (i.e. a mixture of a proapolipoprotein and its corresponding mature apolipoprotein and an additional active agent) in an essentially simultaneous manner, such as in a single pharmaceutical composition, for example, a capsule, tablet and/or an injectable solution having a fixed ratio of first and second amounts, or in multiple, separate capsules solutions for injections or tablets for one of the active agents. In addition, such co-administration also encompasses use of a mixture of a proapolipoprotein and its corresponding mature apolipoprotein and a second active agent in a sequential manner in either order. When co-administration involves the separate administration of the first amount of a mixture of a proapolipoprotein and its corresponding mature apolipoprotein and a second amount of an additional therapeutic agent, the active agents are administered sufficiently close in time to have the desired therapeutic effect. In some embodiments, when co-administration involves the separate administration of the mixture of a proapolipoprotein and its corresponding mature apolipoprotein and a second amount of an additional therapeutic agent, the active agents are administered sufficiently close in time to have the desired therapeutic effect. For example, the period of time between each administration that can result in the desired therapeutic effect, can range from minutes to hours to days and can be determined taking into account the properties of each active agent such as potency, solubility, bioavailability, plasma half-life and kinetic profile. For example, a mixture of a proapolipoprotein and its corresponding mature apolipoprotein described herein and a second therapeutic agent can be administered in any order within about 24 hours of each other, within about 16 hours of each other, within about 8 hours of each other, within about 4 hours of each other, within about 1 hour of each other or within about 30 minutes of each other. In other embodiments, a mixture of a proapolipoprotein and its corresponding mature apolipoprotein described herein and a second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a therapy comprising a mixture of a proapolipoprotein and its corresponding mature apolipoprotein can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second active agent) to a subject. In still other embodiments, a first therapy (e.g., a prophylactic or therapeutic agent such as a therapy comprising a mixture of a proapolipoprotein and its corresponding mature apolipoprotein can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second active agent) to a subject.

E. Methods of Treatment or Prevention

In view of the multiple benefits associated with injectable apolipoprotein compositions, the present compositions, pharmaceutical compositions and formulations, whether injectable or otherwise (e.g. other parenteral administration) can be administered to a patient in need of preventative, therapeutic and curative treatment against apolipoprotein associated diseases and disorders.

In some embodiments, the present compositions, pharmaceutical compositions, injectable apolipoprotein compositions and formulations can be used to increase the plasma concentration of HDL in a subject in need thereof. In some embodiments, the present compositions, pharmaceutical compositions, injectable apolipoprotein compositions and formulations can be used to prevent, treat or cure a cardiovascular disease or disorder in a subject in need thereof. The method comprises administering a therapeutically effective amount of a pharmaceutical composition comprising a mixture of a proapolipoprotein and a corresponding mature apolipoprotein and a pharmaceutically acceptable excipient to the subject.

In certain embodiments, a "subject in need thereof" refers to a subject diagnosed with or predisposed to a cardiovascular disorder or disease or exhibiting one or more conditions or symptoms associated with a cardiovascular disorder or disease, a subject who has been diagnosed with or has exhibited one or more conditions associated with a cardiovascular disorder or disease in the past, or a subject who has been deemed at risk of developing a cardiovascular disorder or disease or one or more conditions associated with a cardiovascular disorder or disease in the future due to hereditary or environmental factors. "Cardiovascular disease" or "CVD" as used herein, includes, for example, atherosclerosis, including coronary artery atherosclerosis and carotid artery atherosclerosis, coronary artery disease (CAD), coronary heart disease (CHD), conditions associated with CAD and CHD, cerebrovascular disease and conditions associated with cerebrovascular disease, peripheral vascular disease and conditions associated with peripheral vascular disease, aneurysm, vasculitis, venous thrombosis, diabetes mellitus, and metabolic syndrome. Over time, hypercholesterolemia and hypertriglyceridemia can lead to the development of atheromatous plaques on the inner arterial linings via the process of atherogenesis, which in turn results in atherosclerosis. Atherosclerosis leads to significantly reduced blood flow through the arteries, which in turn leads to the development of CAD, CHD, and conditions associated with CAD and CHD.

"Conditions associated with CAD and CHD" as used herein include, for example, angina and myocardial infarction (MI; heart attack). "Conditions associated with cerebrovascular disease" as used herein include, for example, transient ischemic attack (TIA) and stroke. In some embodiments, the compositions, pharmaceutical compositions, injectable apolipoprotein compositions and formulations of the present invention can be used for promoting healing of vascular tissue and controlling vascular muscle cell proliferation (hyperplasia) to prevent restenosis of blood vessels after angioplasty, vascular bypass, organ transplantation, or vascular disease, with minimal risk of rapid reocclusion. "Conditions associated with peripheral vascular disease" as used herein include, for example, claudication. In some embodiments, conditions associated with a cardiovascular disorder or disease can include, for example, dyslipidemia, such as for example hyperlipidemia (elevated lipid levels), hypercholesterolemia (elevated cholesterol levels), and hypertriglyceridemia (elevated TG levels), elevated glucose levels, low HDL/LDL ratio, and hypertension. Therefore, in certain embodiments, a subject in need thereof may be a subject exhibiting dyslipidemia or a subject that has exhibited dyslipidemia in the past or has been deemed at risk for developing dyslipidemia in the future. In certain of these embodiments, the subject may exhibit elevated cholesterol levels, or may have exhibited elevated cholesterol levels in the past or been deemed at risk for developing elevated cholesterol levels in the future. Likewise, in certain of these embodiments, the subject may exhibit elevated triglyceride levels, or may have exhibited elevated triglyceride levels in the past or been deemed at risk for developing elevated triglyceride levels in the future.

In some embodiments, methods for the treatment or prevention of a cardiovascular disease or disorder in a subject in need thereof, the method comprises administering to the subject a therapeutically effective amount of a mixture of a proapolipoprotein and a corresponding mature apolipoprotein. In some embodiments, methods for the treatment or prevention of a cardiovascular disease or disorder in a subject in need thereof are provided. In some embodiments, the method comprises administering a therapeutically effective amount of a composition, pharmaceutical composition, injectable apolipoprotein composition or formulation comprising a mixture of a proapolipoprotein and a corresponding mature apolipoprotein and a pharmaceutically acceptable excipient to the subject. In some embodiments, the therapeutically effective amount to be dosed can be determined through appropriately controlled clinical trials, or through the use of titration of carefully determined therapeutically effective doses as described herein. In some embodiments, the subject in need thereof is dosed daily and/or weekly with a composition, pharmaceutical composition, injectable apolipoprotein composition or formulation comprising a therapeutically effective amount of the mixture ranging from about 0.01 mg/kg to about 100 mg/kg, from about 0.05 mg/kg to about 100 mg/kg, from about 0.1 mg/kg to about 100 mg/kg, from about 0.5 mg/kg to about 100 mg/kg, from about 1 mg/kg to about 100 mg/kg, or from about 10 mg/kg to about 100 mg/kg, or from 20 mg/kg to about 100 mg/kg. In some embodiments, a mixture of a proapolipoprotein and its corresponding mature apolipoprotein suitably formulated in a composition, pharmaceutical composition, injectable apolipoprotein composition or formulation may be administered to a subject in need thereof in therapeutically effective amounts ranging from about 0.01 mg/kg to about 90 mg/kg, or from about 0.01 mg/kg to about 70 mg/kg, or from about 0.01 mg/kg to about 50 mg/kg, or from about 0.01 mg/kg to about 25 mg/kg, or from about 0.01 mg/kg to about 20 mg/kg, or from about 0.01 mg/kg to about 10 mg/kg, or from about 0.01 mg/kg to about 5 mg/kg, or from about 0.01 mg/kg to about 1 mg/kg, or from about 0.01 mg/kg to about 0.1 mg/kg. In some embodiments, a therapeutically effective amount of a mixture of a proapolipoprotein and its corresponding mature apolipoprotein in a pharmaceutical composition, may be administered daily and/or weekly to a subject to treat or prevent a cardiovascular disease or disorder in a subject in need thereof, in amounts ranging from about 0.1 mg/kg to about 50 mg/kg. In some embodiments, a therapeutically effective amount of a mixture of a proapolipoprotein and its corresponding mature apolipoprotein in a pharmaceutical composition, may be administered daily and/or weekly to a subject to treat or prevent a cardiovascular disease or disorder in a subject in need thereof, in amounts ranging from about about 1 mg/kg to about 25 mg/kg. In various embodiments, the composition, pharmaceutical composition, injectable apolipoprotein composition or formulation can be administered parenterally.

In some embodiments, the subject in need thereof is dosed daily and/or weekly with a therapeutically effective compositions, pharmaceutical compositions, injectable apolipoprotein compositions or formulations comprising a therapeutically effective amount of a mixture of a proapolipoprotein and a corresponding mature apolipoprotein as described below. In some embodiments, methods for the treatment or prevention of a cardiovascular disease or disorder includes the administration of a therapeutically effective amount of a pharmaceutical composition comprising a mixture of a proapolipoprotein and a corresponding mature apolipoprotein, wherein the therapeutically effective amount of the mixture in the pharmaceutical composition ranges from about 25 mg to about 5,000 mg, or from about 25 mg to about 8,350 mg, or from about 100 to about 5,000, or from about 200 mg to about 5,000 mg, or from about 300 mg to about 5,000 mg, or from about 400 mg to about 5,000 mg, or from about 500 mg to about 5,000 mg, or from about 600 mg to about 5,000 mg, or from about 700 mg to about 5,000 mg, or from about 800 mg to about 5,000 mg, or from about 900 mg to about 5,000 mg, or from about 1,000 mg to about 5,000 mg, or from about 1,250 mg to about 5,000 mg, or from about 1,500 mg to about 5,000 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg.

In some embodiments, the amount of the mixture of a preapolipoprotein and its corresponding apolipoprotein in the composition or pharmaceutical composition is at least 20 mg, or at least 30 mg, or at least 40 mg, or at least 50 mg, or at least 60 mg, or at least 70 mg, or at least 80 mg, or at least 90 mg, or at least 100 mg, or at least 110 mg, or at least 120 mg, or at least 130 mg, or at least 140 mg, or at least 150 mg, or at least 160 mg, or at least 170 mg, or at least 1900 mg, or at least 200 mg, or at least 225 mg, or at least 250 mg, or at least 275 mg, or at least 280 mg, or at least 300 mg, or at least 400 mg. In various embodiments, the aforementioned compositions or pharmaceutical compositions are substantially free of one or more of of phospholipids, lipids, trigycerides, glycerol, cholesterol or liposomes.

In some embodiments, methods for the treatment or prevention of a cardiovascular disease or disorder includes the administration of a therapeutically effective amount of a pharmaceutical composition comprising a mixture of a proapolipoprotein and a corresponding mature apolipoprotein, wherein the amount of the mature apolipoprotein in the mixture can range from about 25 mg to about 4,750 mg, 100 mg to about 4,750 mg, or from about 200 mg to about 4,750 mg, or from about 300 mg to about 4,750 mg, or from about 400 mg to about 4,750 mg, or from about 500 mg to about 4,750 mg, or from about 600 mg to about 4,750 mg, or from about 700 mg to about 4,750 mg, or from about 800 mg to about 4,750 mg, or from about 900 mg to about 4,750 mg, or from about 1,000 mg to about 4,750 mg, or from about 1,250 mg to about 4,750 mg, or from about 1,500 mg to about 4,750 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg.

In some embodiments, methods for the treatment or prevention of a cardiovascular disease or disorder includes the administration of a therapeutically effective amount of a mixture of a proapolipoprotein and a corresponding mature apolipoprotein wherein the amount of the mature apolipoprotein in the mixture is at least 25 mg, or at least 50 mg, or at least 75 mg, or at least 100 mg, or at least 125 mg, or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,740 mg, or at least 3,000 mg, or at least 3,250 mg, or at least 3,500 mg, or at least 2,750 mg, or at least 3,000 mg, or at least 3,250 mg or at least 3,000 mg, or at least 3,250 mg, or at least 3,500 mg, or at least 4,000 mg, or at least 4,500 mg, or at least 5,000 mg, or at least 6,000 mg, or at least 8,350 mg, preferably in a admixture with at least one pharmaceutically acceptable excipient, thereby forming a composition, a pharmaceutical composition, an injectable apolipoprotein composition or a fomulation. In various embodiments, the aforementioned compositions, pharmaceutical compositions, injectable apolipoprotein compositions or fomulations are substantially free of one or more of of phospholipids, lipids, trigycerides, glycerol, cholesterol or liposomes.

In some embodiments, methods for the treatment or prevention of a cardiovascular disease or disorder involves the administration to the subject in need thereof, a composition, a pharmaceutical composition, an injectable apolipoprotein composition or a fomulation that has at least 20 mg, or at least 30 mg, or at least 40 mg, or at least 50 mg, or at least 60 mg, or at least 70 mg, or at least 80 mg, or at least 90 mg, or at least 100 mg, or at least 110 mg, or at least 120 mg, or at least 130 mg, or at least 140 mg, or at least 150 mg, or at least 160 mg, or at least 170 mg, or at least 190 mg, or at least 200 mg, or at least 225 mg, or at least 250 mg, or at least 275 mg, or at least 280 mg, or at least 300 mg, or at least 400 mg of a mixture of a proapolipoprotein and its corresponding mature apolipoprotein. In various embodiments, the aforementioned compositions, pharmaceutical compositions, injectable apolipoprotein compositions or fomulations are substantially free of one or more of of phospholipids, lipids, trigycerides, glycerol, cholesterol or liposomes.

In some embodiments, methods for the treatment or prevention of a cardiovascular disease or disorder involves the administration to the subject in need thereof, an injectable apolipoprotein composition, wherein the therapeutically effective amount of the mixture in the injectable apolipoprotein composition ranges from about 25 mg to about 8,350 mg, or from about 25 mg to about 5,000 mg, or from about 100 to about 5,000, or from about 200 mg to about 5,000 mg, or from about 300 mg to about 5,000 mg, or from about 400 mg to about 5,000 mg, or from about 500 mg to about 5,000 mg, or from about 600 mg to about 5,000 mg, or from about 700 mg to about 5,000 mg, or from about 800 mg to about 5,000 mg, or from about 900 mg to about 5,000 mg, or from about 1,000 mg to about 5,000 mg, or from about 1,250 mg to about 5,000 mg, or from about 1,500 mg to about 5,000 mg, or from about 100 mg to about 3,750 mg, or from about 100 mg to about 3,500 mg, or from about 100 mg to about 3,250 mg, or from about 100 mg to about 3,000 mg, or from about 100 mg to about 2,750 mg, or from about 100 mg to about 2,500 mg, or from about 100 mg to about 2,000 mg, or from about 100 mg to about 1,750 mg, or from about 100 mg to about 1,500 mg, or from about 100 mg to about 1,250 mg, or from about 100 mg to about 1,000 mg, or from about 100 mg to about 750 mg, or from about 100 mg to about 500 mg, or from about 100 mg to about 400 mg, or from about 100 mg to about 300 mg. In some embodiments, the amount of the mixture of a preapolipoprotein and its corresponding apolipoprotein in the injectable apolipoprotein composition is at least 20 mg, or at least 30 mg, or at least 40 mg, or at least 50 mg, or at least 60 mg, or at least 70 mg, or at least 80 mg, or at least 90 mg, or at least 100 mg, or at least 110 mg, or at least 120 mg, or at least 130 mg, or at least 140 mg, or at least 150 mg, or at least 160 mg, or at least 170 mg, or at least 1900 mg, or at least 200 mg, or at least 225 mg, or at least 250 mg, or at least 275 mg, or at least 280 mg, or at least 300 mg, or at least 400 mg. In various embodiments, the aforementioned injectable apolipoprotein compositions are substantially free of one or more of of phospholipids, lipids, trigycerides, glycerol, cholesterol or liposomes.

In some embodiments, the compositions, pharmaceutical compositions, injectable apolipoprotein compositions or fomulations can be administered in a total volume of 40 mL or less, 30 mL or less, or 25 mL or less, or 20 mL or less, or 15 mL or less, or 10 mL or less, or 5 mL or less, or 2.0 mL or less, or 1.5 mL or less, or 1.0 mL or less.

With reference to the above embodiments for the treatment or prevention of a cardiovascular disease or disorder, the compositions, pharmaceutical compositions, injectable apolipoprotein compositions and fomulations comprise a mixture of a proapolipoprotein and its corresponding mature apolipoprotein, wherein the mixture comprises a ratio of proapolipoprotein to corresponding mature apolipoprotein ranging from about 5:95 to about 95:5 (wt %), or from about 20:80 to about 80:20 (wt %), or from about 30:70 to about 70:30 (wt %), or from about 35:65 to about 65:35 (wt %), or from about 40:60 to about 60:40; or from about 45:55 to 55:45 (wt %), or from about 50:50(wt %).

In one embodiment, an exemplary method for treating or preventing a cardiovascular disease or disorder comprises administering to the subject in need thereof, a composition, a pharmaceutical composition, an injectable apolipoprotein composition or a fomulation comprising a mixture of a proapolipoprotein and its corresponding mature apolipoprotein, wherein the mixture comprises a ratio of proapolipoprotein to corresponding mature apolipoprotein ranging from about 35:65 to about 65:35 (wt %), and the amount of mature apolipoprotein in the mixture is at least 25 mg, or at least 50 mg, or at least 75 mg, or at least 100 mg, or at least 125 mg, or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2,250 mg, or at least 2,500 mg, or at least 2,500 mg, or at least 2,750 mg, or at least 3,000 mg, or at least 3,250 mg or at least 3,000 mg, or at least 3,250 mg, or at least 3,500 mg, or at least 4,000 mg, or at least 4,500 mg, or at least 5,000 mg, or at least 6,000 mg, or at least 8,350 mg. In some embodiments, the mixture comprises a ratio of proapolipoprotein to corresponding mature apolipoprotein ranging from about 35:65 to about 65:35 (wt %), and the amount of mature apolipoprotein in the mixture is from about 25 mg to about 3,250 mg.

In one embodiment, an exemplary method for treating or preventing a cardiovascular disease or disorder comprises administering to the subject in need thereof, a composition, a pharmaceutical composition, an injectable apolipoprotein composition or a emulation comprising a mixture of a proapolipoprotein and its corresponding mature apolipoprotein, wherein the mixture comprises a ratio of proapolipoprotein to corresponding mature apolipoprotein ranging from about 45:55 to about 55:45 (wt %), and the amount of mature apolipoprotein in the mixture is at least 25 mg, or at least 50 mg, or at least 75 mg, or at least 100 mg, or at least 125 mg. or at least 150 mg, or at least 200 mg, or at least 225 mg, or at least 250 mg, or at least 275 mg, or at least 280 mg, or at least 300 mg or at least 350 mg, or at least 375 mg, or at least 400 mg, or at least 500 mg, or at least 600 mg, or at least 700 mg, or at least 800 mg, or at least 900 mg, or at least 1,000 mg, or at least 1,250 mg, or at least 1,500 mg, or at least 1,750 mg, or at least 2,000 mg, or at least 2245 mg, or at least 2,250 mg, or at least 2,500 mg, or at least 2,740 mg, or at least 3,000 mg, or at least 3,250 mg, or at least 3,500 mg, or at least 4,000 mg, or at least 4,500 mg, or at least 5,000 mg, or at least 6,000 mg, or at least 8,350 mg. In still other embodiments, an exemplary method for treating or preventing a cardiovascular disease or disorder comprises administering to the subject in need thereof, a a composition, a pharmaceutical composition, an injectable apolipoprotein composition or a fomulation comprising a mixture of a proapolipoprotein and its corresponding mature apolipoprotein, wherein the mixture comprises a ratio of proapolipoprotein to corresponding mature apolipoprotein ranging from about 35:65 to about 65:35 (wt %), and the amount of mature apolipoprotein in the mixture ranges from about 25 mg to about 3,250 mg.

In still other embodiments, an exemplary method for treating or preventing a cardiovascular disease or disorder comprises administering to the subject in need thereof, a a composition, a pharmaceutical composition, an injectable apolipoprotein composition or a fbmulation comprising a mixture of a proapolipoprotein and its corresponding mature apolipoprotein, wherein the mixture comprises a ratio of proapolipoprotein to corresponding mature apolipoprotein ranging from about 45:55 to about 55:45 (wt %), and the amount of mature apolipoprotein in the mixture ranges from about 25 mg to about 2,740 mg.

In various embodiments, the therapeutic doses for the methods for treating or preventing a cardiovascular disease or disorder can be administered intravenously, intraperitoneally, intramuscularly, subcutaneously, or combinations thereof In some embodiments, such administration methods can use therapeutically effective doses of the mixtures of proapolipoprotein and its corresponding apolipoprotein in highly concentrated forms i.e. from about 25 mg to about 5,000 mg per 0.5-40 mL or less liquid volume, for example, 40 mL or less, 30 mL or less, or 25 mL or less, or 20 mL or less, or 15 mL or less, or 10 mL or less, or 5 mL or less, or 2.0 mL or less, or 1.5 mL or less, or 1.0 mL or less, administered at least once per day, for example, at least once per day, or at least twice per day, or every 4 hours, or every 8 hours, or every 12 hours, or every 24 hours, or every 36 hours, or every 48 hours, or one to five times per week, e.g. once per week, or once per two weeks, or once per month, or combinations thereof, for a period of 1-52 weeks, or 1-10 weeks, or at frequencies and/or amounts that improves overall therapy, reduces, avoids or eliminates symptoms, reduces side-effects or causes of a disease or disorder, or enhances the therapeutic efficacy of another therapeutic agent.

In various embodiments of the methods for treating or preventing a cardiovascular disease or disorder, the proapolipoprotein and corresponding mature apolipoprotein comprise apolipoprotein AI, apolipoprotein AII, apolipoprotein B, apolipoprotein E, apolipoprotein AI-Milano, apolipoprotein AI-Paris, apolipoprotein AI-Marburg, apolipoprotein-AI-4WF, and combinations thereof. In some embodiments, the proapolipoprotein and corresponding mature apolipoprotein comprise proapolipoprotein-AI-4WF (SEQ ID NO: 3), and mature apolipoprotein-AI-4WF (SEQ ID NO: 4), or a human wild-type proapolipoprotein-AI(SEQ ID NO:1) and a human wild-type mature apolipoprotein-AI (SEQ ID NO:2).

Exemplary cardiovascular disease and disorders that can be treated or prevented by administering the pharmaceutical compositions or formulations of the present invention to a subject in need thereof, can include: hypercholesterolemia, mixed dyslipidemia, atherosclerosis, a risk of developing atherosclerosis, coronary heart disease, acute coronary syndrome, a history of coronary heart disease, early onset coronary heart disease, metabolic syndrome, type II diabetes, type II diabetes with dyslipidemia, dyslipidemia, hyperlipoproteinemia, hypertriglyceridemia, hyperlipidemia, hyperfattyacidemia, hepatic steatosis, non-alcoholic steatohepatitis, cirrhosis, liver failure, non-alcoholic fatty liver disease, or hypertension.

In certain embodiments, a subject in need thereof may have a condition associated with inflammation, may have been diagnosed with such a condition in the past, or may have been deemed at risk for developing such a condition in the future. In addition to atherosclerosis and certain other forms of a cardiovascular disorder or disease, diseases or conditions associated with inflammation include, for example, multiple sclerosis, Alzheimer's disease, sickle cell, systemic lupus erythematosus, rheumatoid arthritis, and osteoarthritis. In these embodiments, a subject in need thereof may exhibit elevated cardiovascular disease or disorder risk levels, may have exhibited elevated cardiovascular disease symptoms in the past, or may have been deemed at risk for developing cardiovascular disease due to systemic or local inflammation, and/or inflammation of the endothelial cells lining blood vessels associated with hyperlipidemia (elevated lipid levels), hypercholesterolemia (elevated cholesterol levels), and hypertriglyceridemia (elevated TG levels), elevated glucose levels, low HDL/LDL ratio, and hypertension. In certain embodiments, a subject in need thereof may have an inflammatory disease and exhibit elevated levels of one or more additional inflammatory disease markers associated with inflammation, including but not limited to C-reactive protein (CRP), interleukin-6 (IL-6), MCP-1, Tumor Necrosis Factor-alpha (TNF-α), IL-8, ICAM-1, VCAM-1, and MIP-1-α.

In some embodiments, methods for the treatment or prevention of an inflammatory disease or disorder in a subject in need thereof, the method comprises administering to the subject a therapeutically effective amount of a pharmaceutical composition comprising a mixture of a proapolipoprotein and a corresponding mature apolipoprotein. In some embodiments, methods for the treatment or prevention of an inflammatory disease or disorder in a subject in need thereof are provided. In some embodiments, the method comprises administering a therapeutically effective amount of a pharmaceutical composition comprising a mixture of a proapolipoprotein and a corresponding mature apolipoprotein and a pharmaceutically acceptable excipient to the subject. In some embodiments, the therapeutically effective amount to be dosed can be determined through appropriately controlled clinical trials, or through the use of titration of carefully determined therapeutically effective doses as described herein. In some embodiments, the subject in need thereof is dosed daily and/or weekly with a composition, pharmaceutical composition, injectable apolipoprotein composition or formulation comprising therapeutically effective amounts of a mixture of a proapolipoprotein and its corresponding mature apolipoprotein, in amounts ranging from about 0.01 mg/kg to about 100 mg/kg, from about 0.05 mg/kg to about 100 mg/kg, from about 0.1 mg/kg to about 100 mg/kg, from about 0.5 mg/kg to about 100 mg/kg, from about 1 mg/kg to about 100 mg/kg, or from about 10 mg/kg to about 100 mg/kg. In some embodiments, the amount of the mixture of a proapolipoprotein and its corresponding mature apolipoprotein may be administered in amounts ranging from about 0.01 mg/kg to about 90 mg/kg, or from about 0.01 mg/kg to about 70 mg/kg, or from about 0.01 mg/kg to about 50 mg/kg, or from about 0.01 mg/kg to about 25 mg/kg, or from about 0.01 mg/kg to about 20 mg/kg, or from about 0.01 mg/kg to about 10 mg/kg, or from about 0.01 mg/kg to about 5 mg/kg, or from about 0.01 mg/kg to about 1 mg/kg, or from about 0.01 mg/kg to about 0.1 mg/kg. In some embodiments, a therapeutically effective amount of a mixture of a proapolipoprotein and its corresponding mature apolipoprotein in a pharmaceutical composition, may be administered daily and/or weekly to a subject to treat or prevent an inflammatory disease or disorder in a subject in need thereof, in amounts ranging from about 0.1 mg/kg to about 50 mg/kg. In some embodiments, a therapeutically effective amount of a mixture of a proapolipoprotein and its corresponding mature apolipoprotein in a pharmaceutical composition, may be administered daily and/or weekly to a subject to treat or prevent an inflammatory disease or disorder in a subject in need thereof, in amounts ranging from about about 1 mg/kg to about 25 mg/kg. In various embodiments, the composition, pharmaceutical composition, injectable apolipoprotein composition or formulation can be administered parenterally.

In some embodiments, the compositions, pharmaceutical compositions, injectable apolipoprotein compositions and formulations can be used to prevent, treat or cure a cardiovascular disease associated disorder such as metabolic syndrome. Metabolic syndrome is a disorder characterized by a group of metabolic risk factors. These factors include, for example, dyslipidemia, abdominal obesity, elevated blood pressure (hypertension), insulin resistance or glucose intolerance, prothrombotic state, and proinflammatory state. Subjects are generally classified as having metabolic syndrome if they meet three of the five following criteria: I) abdominal obesity (waist circumference >35 inches in women, >40 inches in men); 2) low HDL levels (<50 mg/dL in women, <40 mg/dL in men); 3) high blood pressure (≥130/85 mm Hg) or current treatment with antihypertensive medication; 4) hypertriglyceridemia (TG levels ≥150 mg/dL); and 5) impaired fasting glucose (blood glucose levels of ≥110 mg/dL). Metabolic syndrome is associated with elevated levels of various inflammatory markers, such as CRP or IL-6. Subjects with metabolic syndrome are at increased risk of developing CAD, CHD, conditions associated with CAD and CHD, and type 2-diabetes. In various embodiments, methods for preventing, or treating metabolic syndrome and its related co-morbidities comprises administering a therapeutically effective amount of a pharmaceutical composition comprising a mixture of a proapolipoprotein and a corresponding mature apolipoprotein and a pharmaceutically acceptable excipient to the subject predisposed to or diagnosed with metabolic syndrome.

In some embodiments, the compositions, pharmaceutical compositions, injectable apolipoprotein compositions and formulations of the present invention can be administered to patients in advance or during a surgical procedure for prophylactic effects or to minimize the risk of complications, or to reduce the side effects of a surgical procedure. In some embodiments, a patient can be treated from a few minutes, a few hours, a few days to several weeks before a medical treatment or procedure (e.g., preventive treatment), or during or after a medical act. Administration can be concomitant to or contemporaneous with another invasive therapy, such as, angioplasty, carotid ablation, rotoblader or organ transplant (e.g., heart, kidney, liver, etc.). In one embodiment, intravascular delivery of the compositions, pharmaceutical compositions, injectable apolipoprotein compositions and formulations of the present invention can be administered to areas of suspected or known atherosclerosis, or areas prone to an inflammatory response. Intravascular administration can occur in a number of ways depending on the procedures being performed on the cardiovascularly challenged patient. In one embodiment, a drug eluting stent can be coated, prefilled or connected to depositories containing a therapeutically effective amount of the present pharmaceutical compositions for administration in situ during or immediately after a catheterization to open a blocked cardiac vessel, for example a coronary artery. The term "stent" is used to refer to small tube used to mechanically open an artery. The stent is collapsed to a small diameter, put over a balloon catheter, inserted through a main artery in the groin (femoral artery) or arm (brachial artery) and threaded up to the narrowed/blocked section of the coronary artery. When it reaches the right location, the balloon is inflated slightly to push any plaque out of the way and to expand the artery (balloon angioplasty). When the balloon is inflated, the stent expands, locks in place and forms a scaffold to hold the artery open. The stent stays in the artery permanently. In certain subjects, a stent reduces the renarrowing that occurs after balloon angioplasty or other procedures that use catheters. A stent also may help restore normal blood flow and keep an artery open if it has been torn or injured by the balloon catheter. Reclosure (restenosis) is a problem with the stent procedure.

Drug-eluting stents include stents coated with drugs that are slowly released, but can also include stents which release a therapeutically effective amount of the mixture comprising a proapolipoprotein and its corresponding mature apolipoprotein and/or additional active agents of the present invention stored as part of the stent or the stent is operatively connected to a reservoir containing a mixture of a proapolipoprotein and its corresponding mature apolipoprotein of the present invention. In other embodiments, drug-eluting stents include stents coated with drugs that are slowly released, but can also include stents which release a mixture of a proapolipoprotein and its corresponding mature apolipoprotein and/or additional active agents of the present invention stored as part of the stent or the stent is operatively connected to a reservoir containing the mixture of a proapolipoprotein and its corresponding mature apolipoprotein of the present invention. Pharmaceutical compositions of the present invention can be used to help keep a blood vessel from reforming an atherosclerotic plaque, stabilize a preexisting plaque or prevent an existing plaque from rupturing, causing a potential embolism, cerebral or myocardial infarct, or vascular blockage.

In some embodiments, methods for increasing the plasma concentration of HDL in a subject in need thereof are provided. In some embodiments, the method comprises administering a therapeutically effective amount of a composition or a pharmaceutical composition comprising a mixture of a proapolipoprotein and a corresponding mature apolipoprotein and a pharmaceutically acceptable excipient to the subject. In some embodiments, the therapeutically effective amount to be dosed can be determined through appropriately controlled clinical trials, or through the use of titration of carefully determined therapeutically effective doses as described herein. In some embodiments, the subject in need thereof is dosed daily and/or weekly with a composition, pharmaceutical composition, injectable apolipoprotein composition or formulation comprising therapeutically effective doses ranging from about 0.01 mg/kg to about 100 mg/kg, from about 0.05 mg/kg to about 100 mg/kg, from about 0.1 mg/kg to about 100 mg/kg, from about 0.5 mg/kg to about 100 mg/kg, from about 1 mg/kg to about 100 mg/kg, or from about 10 mg/kg to about 100 mg/kg. In some embodiments, the amount of the mixture of a proapolipoprotein and its corresponding mature apolipoprotein may be administered in amounts ranging from about 0.01 mg/kg to about 90 mg/kg, or from about 0.01 mg/kg to about 70 mg/kg, or from about 0.01 mg/kg to about 50 mg/kg, or from about 0.01 mg/kg to about 25 mg/kg, or from about 0.01 mg/kg to about 20 mg/kg, or from about 0.01 mg/kg to about 10 mg/kg, or from about 0.01 mg/kg to about 5 mg/kg, or from about 0.01 mg/kg to about 1 mg/kg, or from about 0.01 mg/kg to about 0.1 mg/kg. In some embodiments, a therapeutically effective amount of a mixture of a proapolipoprotein and its corresponding mature apolipoprotein in a pharmaceutical composition, may be administered daily and/or weekly to a subject to increase the subject's plasma concentration of HDL, in amounts ranging from about 0.1 mg/kg to about 50 mg/kg. In some embodiments, a therapeutically effective amount of a mixture of a proapolipoprotein and its corresponding mature apolipoprotein in a pharmaceutical composition, may be administered daily and/or weekly to a subject to increase the subject's plasma concentration of HDL, in amounts ranging from about 25 mg to about 8,350 mg. In some embodiments, a therapeutically effective amount of a mixture of a proapolipoprotein and its corresponding mature apolipoprotein in a pharmaceutical composition, may be administered daily and/or weekly to a subject to increase the plasma concentration of HDL, in amounts ranging from about about 1 mg/kg to about 25 mg/kg. In various embodiments, the composition, pharmaceutical composition, injectable apolipoprotein composition or formulation can be administered parenterally.

In various embodiments related to the above described methods of treatment, the ratio of proapolipoprotein to corresponding apolipoprotein in the mixture ranges from about 5:95 to about 95:5 (wt %), or from about 20:80 to about 80:20 (wt %), or from about 35:65 to about 65:35 (wt %), or from about 40:60 to about 60:40 (wt %), or from about 45:55 to about 55:45 (wt %). In some embodiments, ratio of proapolipoprotein to corresponding apolipoprotein in the mixture is about 50:50 (wt %). In some embodiments, the method for increasing the plasma concentration of HDL in a subject in need thereof comprises administering to the subject a mixture comprising a ratio of proapolipoprotein to corresponding mature apolipoprotein ranging from about 45:55 to about 55:45 (wt %), and the amount of mature apolipoprotein in the mixture ranges from about 25 mg to about 5,000 mg. In some embodiments, the method for increasing the plasma concentration of HDL in a subject in need thereof comprises administering to the subject a mixture comprising a ratio of proapolipoprotein to corresponding mature apolipoprotein ranging from about 35:65 to about 65:35 (wt %), and the amount of mature apolipoprotein in the mixture ranges from about 25 mg to about 5,000 mg.

In some embodiments, pharmaceutical compositions of the present invention are also useful in promoting the mobilization and efflux of stored cholesterol located in atherosclerotic plaques and/or sites of inflammation. In a preferred embodiment, the pharmaceutical compositions are used to promote the mobilization and efflux of stored cholesterol from macrophages and other tissues located in atherosclerotic plaques or sites of inflammation in vivo. More preferably, the pharmaceutical compositions are used to promoting the mobilization and efflux of stored cholesterol from macrophages and other tissues located in atherosclerotic plaques or sites of inflammation in mammals and in particular humans.

In still further embodiments, the present invention provides a method of treating a metabolic disease or disorder in a subject, the method comprising administering to the subject, a therapeutically effective amount of a pharmaceutical composition comprising a mixture of a proapolipoprotein and a corresponding mature apolipoprotein. Doses and routes of administration are provided herein and are exemplified for the methods used for the treatment of cardiovascular diseases. In some embodiments, the amount to be dosed and the route of administration fused for optimal treatment can be determined using clinical trials and can be determined using the sound experience of medical practitioners. Metabolic disease includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary artery disease, cardiovascular disease, polycystic ovary syndrome (PCOS). "Metabolic Syndrome" or "Metabolic Syndrome X" refers to a condition identified by the presence of three or more of these components: Central obesity as measured by waist circumference: Men: Greater than 40 inches; Women: Greater than 35 inches; Fasting blood triglycerides greater than or equal to 150 mg/dL; Blood HDL cholesterol: Men: Less than 40 mg/dL; Women: Less than 50 mg/dL; Blood pressure greater than or equal to 130/85 mmHg; Fasting blood glucose greater than or equal to 110 mg/dL. As used herein, "Obesity" refers to the condition of being obese. Being obese is defined as a body mass index (BMI) of 30.0 or greater, and extreme obesity is defined at a BMI of 40 or greater. "Overweight" is defined as a BMI of 25.0 to 29.9.

In some embodiments, the doses administered are part of an acute or temporary treatment, wherein one or more treatment cycles lasts 1-7 days, or 1-4 weeks, or 1-3 months, or 3-12 months. In one embodiment, the subject is treated with one or more therapeutically effective doses, wherein the pharmaceutical composition is administered intravenously, intraperitoneally, intramuscularly, subcutaneously, or combinations thereof. In some embodiments, the pharmaceutical composition is administered at least once per day, or at least twice per day, or every 4 hours, or every 8 hours, or every 12 hours, or every 24 hours, or every 36 hours, or every 48 hours, or once per week, or once per two weeks, or once per month, or combinations thereof.

In one embodiment, the subject is treated with one or more therapeutically effective doses per day providing a daily or weekly dose of about 0.01 mg/kg to about 100 mg/kg body weight, or from about 0.1 mg/kg to about 50 mg/kg, or from about 0.5 mg/kg to about 15 mg/kg body weight of the combined mixture of proapolipoprotein and its corresponding mature apolipoprotein, administered every 2-7 days, or at least once per week for a period of 1-52 weeks, or 1-10 weeks, or 1-5 weeks. This cycle can be repeated any number of times, or administration of the therapeutically effective doses may continue indefinitely, or at least until the levels of HDL is raised to control levels (+/− normal HDL level population variation), or until amelioration, prevention, cure or other measure of improvement in one or more symptoms acknowledeged in the medical field for the diseases or disorders exemplified is achieved. In some embodiments, the subject in need of treatment requires chronic administration of one or more daily doses per week, or one or more weekly doses of the pharmaceutical composition provided herein for an indefinite period of time, for example, one or more years until, the level of circulating apolipoprotein, for example, Apo-AI is above a predetermined reference point indicative of healthy levels of HDL or until one or more symptoms associated with a cardiovascular, inflammatory or metabolic disease has been reduced, alleviated, or diminished to medically acceptable levels or completely eliminated, enabling management of the disease. In some embodiments, the pharmaceutical composition of the present invention is administered at therapeutically effective doses, for example, about 25 mg to about 5,000 mg per dose, dosed one or more times daily or weekly, or a daily dose of about 25 mg to about 5,000 mg, or a weekly dose of about 25 mg to about 5,000 mg for 1-52 weeks or as required until one or more symptoms associated with a cardiovascular, inflammatory or metabolic disease has been reduced, alleviated, or diminished to medically acceptable levels or completely eliminated, enabling management of the disease.

In some embodiments, the therapeutic doses can be administered intravenously, intraperitoneally, intramuscularly, subcutaneously, or combinations thereof. In some embodiments, such administration methods can use therapeutically effective doses of the mixtures of proapolipoprotein and its corresponding apolipoprotein in highly concentrated forms i.e. from about 25 mg to about 5,000 mg per 1-30 mL or less, injection volume, administered one or more times during the day, or one to 5 times weekly for a period of 1-52 weeks, or 1-10 weeks.

Methods for measuring the levels of HDL in subjects are common and routine. After dosing with the compositions, pharmaceutical compositions, injectable apolipoprotein compositions and formulations described herein, HDL cholesterol levels can be measured to determine efficacy of the treatment and the need for dosing alterations. For in-vivo determination of cardiovascular regression/progression, after treatment with the compositions, pharmaceutical compositions, injectable apolipoprotein compositions and formulations described herein, several non-invasive screening procedures are available, for example to determine whether symptoms or conditions associated with cardiovascular disease, e.g. atherosclerosis are present. In one embodiment, after one or more cycles of treatment in a subject with, suspected of having or at risk for developing atherosclerosis, measurement of plaque formation can be performed using magnetic resonance imaging (MRI) alone or combined with intravascular ultrasound. In one embodiment, the subject can have one or more arteries, carotid, jugular, aortic or coronary scanned with MRI and/or intravascular ultrasound prior to treatment. Then after one or more cycles of treatment, the same arteries can be rescanned to determine the presence or absence of plaque, and if initially present prior to treatment, the measure of reduction or accumulation of plaque in said artery.

In one embodiment, the intravascular ultrasound evaluation of an artery (for example a carotid artery) can be performed using a mechanical IVUS system (e.g. a Galaxy 2, Boston Scientific, Fremont, Calif.) using standard radiographic and ultrasound techniques. The origin of the right carotid artery from the aortic arch can be used as the anatomical landmark to co-register pre- and post-treatment scans. Atheroma area can be calculated as the external elastic membrane area minus luminal area. Plaque area can be measured on all slices covering the lesion. In one illustrative method, the sum of the areas can be multiplied by the slice thickness value (0.5 mm) to obtain plaque volume. The point of maximal plaque formation is considered to be the cross-section with the maximal plaque area.

In addition to intravascular ultrasound to measure plaque volume, an MRI scan can be performed on the subject pre and post-treatment. In some embodiments the magnetic resonance images from different time points can be co-registered by using an anatomical reference point, for example the spinal cord structure as and analyzed by the radiographer. The MRI plaque area can be determined on both carotid arteries and on all slices covering an identified lesion. The sum of areas is multiplied by the slice thickness value (1.8 mm) to obtain plaque volume. For each carotid artery, plaque volumes can be calculated as the mean value from those obtained with the different contrast images (T2, T1 before contrast agent, T1 after contrast agent).

Statistical analysis using as mean ±SEM can be used to determine group differences for statistical significance by analysis of variance for repeated measurements with 1 grouping factor or I-way analysis of variance, followed by the Tukey post-hoc test; a value of $p<0.05$ was considered statistically significant. In some embodiments, the clinical effect of the compositions, pharmaceutical compositions and formulations of the present invention can be statistically determined using the Pearson correlation coefficient for interobserver and intraobserver variability and for statistical comparison of plaque volumes obtained by intravascular ultrasound, MRI, and histology.

F. Kits

In some embodiments, the present invention provides kits for increasing the plasma level of HDL, for increasing the ratio of HDL:LDL and for the treatment, prevention and cure of a cardiovascular disease or disorder or metabolic syndrome disease. In some embodiments, the kit comprising at least one unit dose of a mixture of proapolipoprotein, and a corresponding mature apolipoprotein, and at least one pharmaceutically-acceptable excipient to administer the dosage form according to a medical treatment or prevention regimen, the kit optionally comprising instructions for use of the kit.

In some embodiments, the at least one unit dose of the mixture of proapolipoprotein, and a corresponding mature apolipoprotein comprises a ratio of proapolipoprotein to corresponding mature apolipoprotein ranging from about 5:95 to about 95:5 (wt %), or from about 35:65 to about 65:35 (wt %), an amount of mature apolipoprotein in the mixture ranges from about 25 mg to about 3,750 mg, and at least one excipient selected from the group consisting of a solubilizer, a suspending agent, an isotonic agent, a buffering agent, and a pH adjusting agent, wherein the excipient is stored in a sterile container or in admixture with the mixture.

In still further embodiments, the proapolipoprotein and corresponding mature apolipoprotein in the kit can comprise human proapolipoprotein-AI-4WF (SEQ ID NO: 3), and human mature apolipoprotein-AI-4WF (SEQ ID NO: 4), or a human wild-type proapolipoprotein-AI (SEQ ID NO: 1) and a human wild-type mature apolipoprotein-AI (SEQ ID NO:2).

The present methods and compositions are further illustrated and exemplified in the examples provided below.

G. Examples

Example 1

Method For Increasing The Solubility of Human Wild-Type Apo-AI and Apo-AI-4WF

Dialysis:

All glassware and appropriate materials coming in contact with the sample were baked at 260° C. overnight and cassette floats soaked in 1 mM NaOH overnight and repeatedly washed in sterile ultra pure water. All steps where the sample is exposed to the open air were performed in a biosafety cabinet. Samples were thawed on ice for approximately one hour. Prior to sample loading, the dialysis cassettes (30 mL Dialysis Cassettes 10 kDa MWCO, Slide-A-Lyzer, Cat. No. 66456, Lot No. ML165714 Thermo Scientific, Pittsburgh, USA) were soaked in sterile saline for 5 minutes. 40 mL (15 mg/mL) of Apo-AI-WT, and 40 mL (12.5 mg/mL) Apo-AI-4WF were loaded into the dialysis cassettes per the manufactures directions. Four 1:100 volume dialysis exchanges were performed in normal saline at 4° C. with gentle stirring. Exchange 1 went overnight, exchanges 2 and 3 were for 3 hours, and the final exchange was overnight (1:100,000,000 total volume dilution). Following the final buffer exchange, the sample was recovered, submitted for protein concentration measurement and stored at 2-8° C.

In one experimental example, the recovery and yield of the dialyzed Apo-AI-WT protein was: 12.99 mg/mL in 45 mL=~97.5% yield; Apo-AI-4WF:7.52 mg/mL in 48 mL=~72.2% yield. In further processing step, Apo-AI-WT was diluted in saline to 7.52 mg/mL Sample Concentration:

Approximately 3 mL of Apo-AI-WT (7.52 mg/mL) of sample preparation was loaded into the Amicon® Ultra-15 Centrifugal Filter Unit (Millipore Catalog No. UFC901024, Lot. No. RIKA04367) with Ultracel-10 membrane (Millipore Cat. No. UFC901024). The sample was spun at 3,000 rpm in a Beckman Allegra 6R Refrigerated Benchtop Centrifuge (Beckman Coulter Item No. 366816, Brea Calif., USA) configured with a GH-3.8 rotor for one hour at 4° C. The sample volume was checked, and subjected to an additional 2 hours of centrifugation at 4° C. In one experimental example, 50 µL of Apo-AI-WT and 63 µL of Apo-AI-4WF were recovered from the Amicon ultrafiltration column and protein concentration determined.

Mixture of preapolipoprotein and mature apolipoprotein Apo-AI-WT: 219.0 mg/mL in 50 µL=~48.5% yield Mixture of preapolipoprotein and mature apolipoprotein Apo-AI-4WF: 167 mg/mL in 63 µL=~46.6% yield.

In one example, the amount of pure mature Apo-AI-4WF concentrated using the methods of the present invention was 2.84 mg/mL. The amount of the mixture of proapolipoprotein-AI-4WF and mature apolipoprotein-AI-4 WF concentrated in identical fashion as the pure sample was 167 mg/mL. The amount of mature apolipoprotein-AI-4WF in the mixture was calculated as 48%×167 mg/mL=80.16 mg/ml., which equates to approximately a 28 fold concentration factor using the methods described and claimed herein.

Protein Concentration Measurement:

Using a UV spectrophotometer set to Absorbance at 280 nm, a saline blank is used to establish a zero setting. The protein solution is diluted to a concentration such that the absorbance reading when a cuvette containing the solution is introduced into the spectrophotometer the measured reading is in the range of 0.1 to 1.0 AUFS. Triplicate absorbance readings of the protein solution are made and the mean of the three measurements is determined. The concentration of Apo-AI-WT is determined by the following equation:

$$\text{Concentration (Apo-AI-WT)} = \text{Mean absorbance reading (280 nm)} \times 0.8658 \times \text{dilution}$$

The concentration of Apo-AI-4WF is determined by the following equation:

$$\text{Concentration (Apo-AI-4WF)} = \text{Mean absorbance reading (280 nm)} \times 2.677 \times \text{dilution}.$$

The constants used in the equations above are derived from the theoretical A280 nm absorbance contributions from the amino acids in the protein, with a strong contribution from tryptophan.

Example 2

Determination of Ratios of Pro and Mature Forms in Apo-AI-WT and Apo-AI-41W

Samples of concentrated and non-concentrated mixtures of a proapolipoprotein and a corresponding mature apolipoprotein were resolved and each of the proapolipoprotein and mature apolipoprotein in each sample was quantified using gradient reverse phase liquid chromatography. In one example, the ratio of pro- Apo-AI-WT and mature-Apo-AI-WT and the ratio of pro- Apo-AI-WT and mature-Apo-At-WT were determined using a reverse phase High Performance Liquid Chromatography (HPLC). A Discovery Bio Wide Pore C5 column (150 mm×4.6 mm ID 5 µm, Cat. No. 568422-U, Sigma Aldrich, St. Louis Mo., USA) was developed after sample loading with a gradient system comprising a first Mobile Phase: Reservoir A containing: 25/75 (v/v) 0.1% TFA in acetonitrile/0.1% TPA in H$_2$O; and a second mobile phase Reservoir B containing: 75/25 (v/v) 0.1% TEA in acetonitrile/ 0.1% TFA in H$_2$O. The gradient program consisted of: 0-100% B in 70 minutes; Flow Rate: 1.0 mL/min; Column Temperature: 50° C.; UV Detection: 280 nm; Injection Volume: 20 µL. In one experiment, the relative concentration ratio of proapolipoprotein-AI-WT:mature apolipoprotein-AI-WT in an apolipoprotein-AI-WT mixture was about 37%:63% ±0.1% (wt %). In another experiment, the relative concentration ratio of proapolipoprotein-AI-4WF: mature apoliprotein-AI-4WF in an apolipoprotein-AI-4WF mixture was about 52%:48% ±0.1% (wt %).

Example 3

In Vitro Activity of Pro/Mature Apo-AI WT/4WF Mixture—ATP-Binding Cassette Transporter AI (ABCA1)-Dependent Cholesterol Efflux RAW 264.7 murine macrophage cells were isolated from the wild type host (C57/BL6 mice, The Jackson Laboratory) and differentiated in vitro for 10 days prior to loading with labeled cholesterol.

Cells are subsequently washed and then incubated for 18-24 hrs. with ±0.3 mmol/L 8Br-cAMP to induce ABCAI activity. The cells are subsequently washed and chased for 4 hours in serum-free medium containing various concentrations of an apolipoprotein-AI preparation ranging from 0.1 to 30 μg/mL. The apolipoprotein-AI preparation included a mixture of human wild-type proapolipoprotein-AI (SEQ ID NO:1) and human wild-type mature apolipoprotein-AI (SEQ ID NO:2) comprising a ratio of 37% human wild-type proapolipoprotein-AI: 63% human wild-type mature apolipoprotein-AI (wt %), or a second mixture comprising proapolipoprotein-AI-4WF (SEQ ID NO:3) and mature apolipoprotein-AI-4WF (SEQ ID NO:4) in a mixture having a ratio of 52% proapolipoprotein-AI-4WF: 48% mature apolipoprotein-AI-4WF (wt %). The radioactivity in the chase media is determined after brief centrifugation to pellet debris. Radioactivity in wells designated "Total" is then determined by aspirating the media and cells which were incubated with the radiolabelled cholesterol prior to the initiation of the chase period followed by extraction of the incorporated radiolabelled cholesterol from the cells in hexane:isopropanol (3:2) with the solvent evaporated in a scintillation vial prior to counting. The percent cholesterol efflux is calculated as 100× (chase medium dpm)/(Total dpm) for condition ±0.3 mmol/L 8Br-cAMP. ABCA-1-dependent cholesterol is calculated by subtracting percent efflux in cells without the addition of 0.3 mmol/L 8Br-cAMP from parallel conditions with 0.3 mmol/L 8Br-cAMP added. As can be seen in FIG. 2, mixtures of proapolipoprotein-AI-4WF and mature apolipoprotein-AI-4WF comprising a ratio of 52% proapolipoprotein-AI-4WF: 48% mature apolipoprotein-AI-4WF were shown to be resistant to the activity of myeloperoxidase when compared to human wild-type Apo-AI.

Example 4

In Vivo Measurement of ApoAI Plasma Residence

Apo-AI−/− mice (B6.129P2-Apo-AI$^{tm1Unc}$/J, (The Jackson Laboratory) are processed and bone marrow macrophages are isolated and labeled with 1% FBS containing 0.3 μCi/mL [3H]-cholesterol (Perkin Elmer) for 18 hrs as described below. As shown in FIG. 1, bone marrow macrophages are extracted from Apo-AI−/− mice. The macrophages are incubated in 1% FBS containing 0.3 μCi/mL [$^3$H]-cholesterol (Perkin Elmer) for 18 hours and subsequently washed. The macrophages are then re-injected into the mice, via intraperitoneal injection. The mice are then injected intravenously or subcutaneously with 0.4 mg an apolipoprotein-AI preparation per gram of body weight. The apolipoprotein-AI preparation included a mixture of human wild-type proapolipoprotein-AI (SEQ ID NO:1) and human wild-type mature apolipoprotein-AI (SEQ ID NO:2) comprising a ratio of 37% human wild-type proapolipoprotein-AI: 63% human wild-type mature apolipoprotein-AI (wt %), or a second mixture comprising proapolipoprotein-AI-4WF (SEQ ID NO:3) and mature apolipoprotein-AI-4WF (SEQ ID NO:4) in a mixture having a ratio of 52% proapolipoprotein-AI-4WF: 48% mature apolipoprotein-AI-4WF (wt %). Total plasma apolipoprotein-AI (human preapolipoprotein-AI WT and mature apolipoprotein-AI WT and pro- and mature apolipoprotein-AI-4WF) was measured at 1, 5, 24, and 48 hours after the intravenous apolipoprotein-AI mixture injection, or at 5, 24, and 48 hours after the subcutaneous injection of same. See the schematic representation of the method in FIG. 1.

Figure 3B:
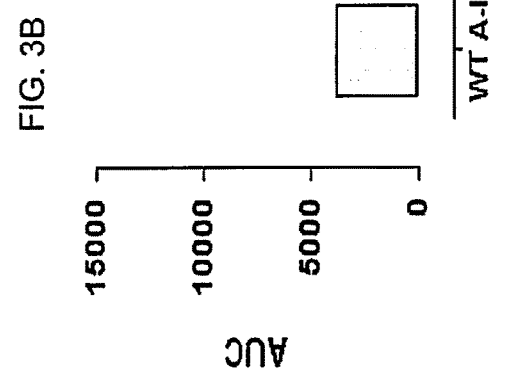
FIG. 3B shows a bar chart representing the area under the curve (AUC) of the experimental results obtained in FIG. 3A.
Figure 3A:
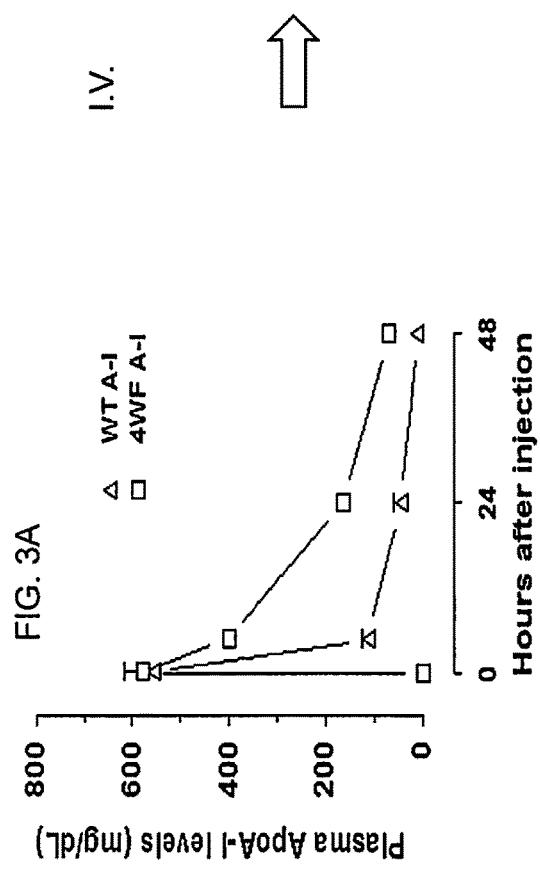
FIG. 3A illustrates a line chart indicating the relative plasma residence time in vivo of mixtures of proapolipoprotein and its corresponding mature apolipoprotein when injected intravenously (I.V.) into mice.
Figure 3D:
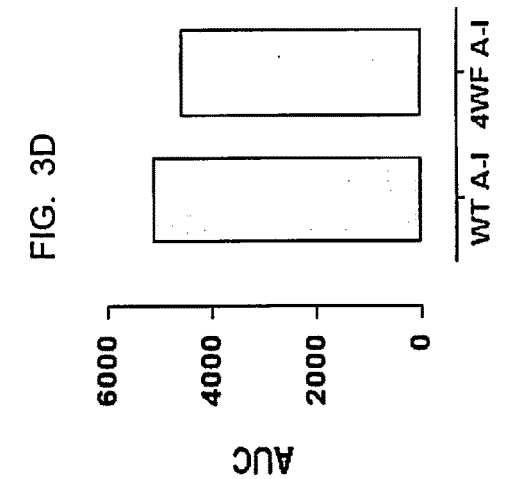
FIG. 3D shows a bar chart representing the area under the curve (AUC) of the experimental results obtained in FIG. 3C.
Figure 3C:
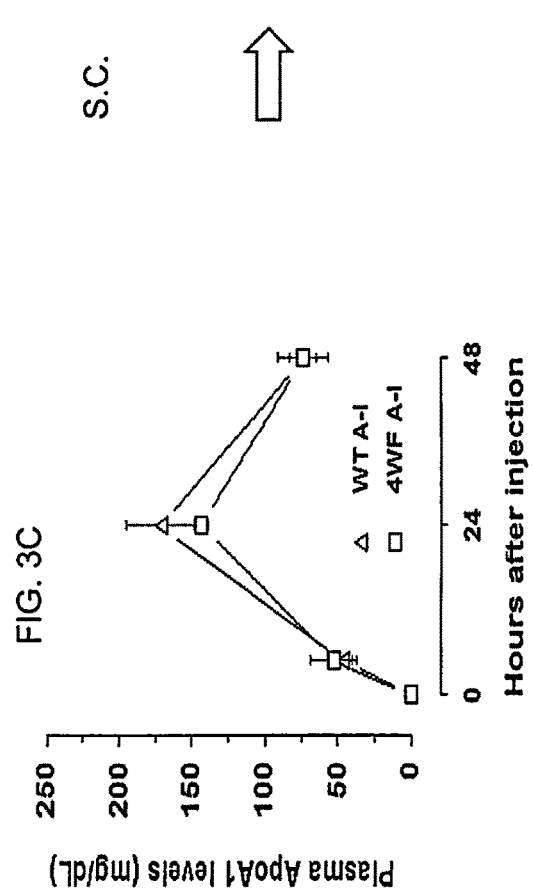
FIG. 3C illustrates a line chart indicating the relative plasma residence time in vivo of mixtures of proapolipoprotein and its corresponding mature apolipoprotein when injected subcutaneously (S.C.) into mice.

As shown in FIGS. 3A and 3C, plasma apolipoprotein-AI concentrations reach a maximum of ~550-600 mg/dL at 1 hour post intravenous injection for both apolipoprotein-AI-WT and apolipoprotein-AI-4WF mixtures. Plasma concentrations of Apo-AI-WT decrease thereafter considerably more rapidly than do plasma concentrations of Apo-AI-4WF. At 5 hours post-injection, the plasma concentration of Apo-AI-WT has decreased to ~20% of its 1 hour maximum, whereas the plasma concentration of Apo-AI-4WF is still at ~70% of its 1 hour maximum. The Apo-AI-4WF concentration remains higher at 24 and 48 hours, although the difference diminishes as both concentrations approach zero. This result is highlighted in the left panel of FIG. 3A. As shown in FIG. 3B, AUC after intravenous injection was 2×greater or more for Apo-AI-4WF than for Apo-AI-WT.

As shown in FIG. 3C, subcutaneous injection resulted in highly similar plasma residence time curves for Apo-AI-4WF and Apo-AI-WT. Upon subcutaneous injection of either Apo-AI-WT or Apo-AI-4WF mixtures, the concentration of the apolipoprotein rose to a maximum of ~150-175 mg/dL at 24 hours, and then decreased to roughly half that value at 48 hours post-injection. As shown in FIG. 3D, subcutaneous injection of either preparation resulted in an AUC of approximately 4500-5000 mg·hr/dL. Notably, this is comparable to the AUC resulting from intravenous injection of Apo-AI-WT (FIG. 3B).

Example 5

In vivo Formation Of HDL Particles

Bone marrow macrophages are extracted from Apo-AI−/− mice (B6.129P2-Apo- AI$^{tm1Unc}$/J, (The Jackson Laboratory)). The macrophages are incubated in 1% FBS containing 0.3 μCi/mL [$^3$H]-cholesterol (Perkin Elmer) for 18 hours and subsequently washed. The macrophages are then re-injected into the mice, via intraperitoneal injection. The mice are then injected intravenously or subcutaneously with 0.4 mg of an Apo-AI preparation per gram of body weight. The apolipoprotein-AI preparation included a mixture of human wild-type proapolipoprotein-AI (SEQ ID NO:1) and human wild-type mature apolipoprotein-AI (SEQ ID NO:2) comprising a ratio of 37% human wild-type proapolipoprotein-AI: 63% human wild-type mature apolipoprotein-AI (wt %), or a second mixture comprising proapolipoprotein-AI-4WF (SEQ ID NO:3) and mature apolipoprotein-AI-4WF (SEQ ID NO:4) in a mixture having a ratio of 52% propolipoprotein-AI-4WF: 48% mature apolipoprotein-AI-4WF (wt %). Plasma levels of cholesterol contained in HDL (HDL-C) are measured at 5, 24, and 48 hours post-injection.

Additionally, a plasma sample is collected 48 hours post-injection and diluted 1:100 with PBS, separated on native polyacrylamide gel under non-denaturing conditions, transferred to a membrane, and probed with a-human-Apo-AI antibody. See the schematic representation of the method in FIG. 1.

As shown in FIG. 4A, the plasma level of HDL-C rises considerably after intravenous injection of either Apo-AI-WT or Apo-AI-4WF mixture preparations, reaching a maximum at 24 hours and then decreasing relatively slowly from 24 to 48 hours post-injection. HDL-C rises to significantly higher levels after intravenous injection of Apo-AI-4WF than after intravenous injection of Apo-AI-WT. The HDL-C level after intravenous injection of Apo-AI-4WF reaches a maximum of ~100 mg/dL at 24 hours post-injection, decreasing slowly thereafter. In contrast, the HDL-C level resulting from intravenous injection of Apo-AI-WT reaches a maximum of ~65 mg/dL at 24 hours, decreasing slowly thereafter. This result is highlighted by a block arrow, on the left side of FIG. 4A. As shown in FIG. 4B, AUC for intravenously injected Apo-AI-4WF mixture is significantly greater than for Apo-AI-WT mixture (approximately 3500 and 2500 mg·hr/dL, respectively). As shown in FIG. 4C, a Western Blot of plasma after intravenous injection of Apo-AI-WT mixture or Apo-AI-4WF mixture indicates electrophoretic migration of apolipoprotein consistent with incorporation of the apolipoprotein into HDL particles.

As shown in FIG. 4D, the plasma HDL-C level rises considerably after subcutaneous injection of either Apo-AI-WT mixture or Apo-AI-4WF mixture. Specifically, the plasma HDL-C level is approximately 30 mg/dL, 75 mg/dL, and 85 mg/dL at 5, 24, and 48 hours, respectively, after subcutaneous injection of Apo-AI-WT or Apo-AI-4WF. As shown in FIG. 4E, subcutaneous injection of Apo-AI-WT mixture or Apo-AI-4WF mixture resulted in an AUC of approximately 3000 mg·hr/dL. Notably, this is equal to or greater than the AUC resulting from intravenous injection of the Apo-AI-WT mixture (FIG. 4E). As shown in FIG. 4F, a Western Blot of plasma after subcutaneous injection of Apo-AI-WT mixture or Apo-AI-4WF mixture indicates electrophoretic migration of apolipoprotein consistent with incorporation of the apolipoprotein into HDL particles.

Example 6

In Vivo Reverse Cholesterol Transportation

Bone marrow macrophages are extracted from Apo-AI−/− mice ((B6.129P2-Apo-AItmlUnc/J, (The Jackson Laboratory)). The macrophages are incubated in 1% FBS containing 0.3 µCi/mL [3H]-cholesterol (Perkin Elmer) for 18 hours and subsequently washed. The macrophages are then re-injected into the mice, via intraperitoneal injection. The mice are then injected intravenously or subcutaneously with 0.4 mg of an Apo-AI preparation per gram of body weight. The apolipoprotein-AI preparation included a mixture of human wild-type proapolipoprotein-AI (SEQ ID NO:1) and human wild-type mature apolipoprotein-AI (SEQ ID NO:2) comprising a ratio of 37% human wild-type proapolipoprotein-AI: 63% human wild-type mature apolipoprotein-AI (wt %), or a second mixture comprising proapolipoprotein-AI-4WF (SEQ ID NO:3) and mature apolipoprotein-AI-4WF (SEQ ID NO:4) in a mixture having a ratio of 52% proapolipoprotein-AI-4WF: 48% mature apolipoprotein-AI-4WF (wt %). See the schematic representation of the method in FIG. 4. At 5, 24, and 48 hours post-injection, plasma samples are removed and Reverse Cholesterol Transport (RCT) is assayed as follows. Total radioactivity is measured by adding a 3:2 hexane:isopropanol solvent to extract radiolabelled cholesterol from macrophages, followed by scintillation counting. Radioactivity of the HDL fraction is measured by removing the cellular fraction via brief centrifugation, adding the extraction solvent, and scintillation counting. Total radioactivity is measured by adding a 3:2 hexane:isopropanol solvent to extract radiolabelled cholesterol from macrophages, followed by scintillation counting. The percent cholesterol efflux was calculated as the radioactivity in the plasma divided by the total radioactivity in macrophages introduced into mouse host.

As shown in FIG. 5A, RCT increases after intravenous injection of Apo-AI-WT mixture or Apo-AI-4WF mixture. RCT appears to be greater after intravenous injection of Apo-AI-4WF mixture than after intravenous injection of Apo-AI-WT mixture. The RCT after intravenous injection of Apo-AI-WT mixture is ~1.4%, 1.6%, and 1.5% at 5, 24, and 48 hours post-injection, respectively. Conversely, the RCT after intravenous injection of Apo-AI-4WF mixture is ~1.5%, 2.7%, and 1.8% at 5, 24, and 48 hours post-injection, respectively. The substantially greater RCT at 24 hours after intravenous injection of Apo-AI-4WF mixture as compared to Apo-AI-WT mixture is shown in FIG. 5B. As shown in FIG. 5B, the greater degree of RCT upon intravenous injection of Apo-AI-4WFmixture results in a higher AUC of ~100%·hr upon intravenous injection of Apo-AI-4WF mixture, as compared to ~70%·hr upon intravenous injection of Apo-AI-WT mixture.

As shown on FIG. 5C, the RCT rises to very similar levels after subcutaneous injection of either Apo-AI-WT or Apo-AI-4WF mixtures. The RCT is approximately 1-1.4%, 2.5%, and 2% at 5, 24, and 48 hours after subcutaneous injection of either Apo-AI-WT or Apo-AI-4WF mixtures. As shown in FIG. 5D, AUC is similar for subcutaneously injected Apo-AI-WT and Apo-AI-4WF mixtures.

Example 7

In Vivo Activity of Pro/Mature Apo-AI WT/4WF Mixture—Carotid Artery Investigation ApoE−/− mice (Taconic) were kept on 60 kcal % high fat diet (Research Diet) for two weeks prior to the surgical procedure. Before surgery, mice were anesthetized using isoflurane inhalation and placed in the supine position on surgical/dissecting block. The cervical area was shaved and prepped with Nolvasan scrub followed by a 70% alcohol rinse. Under a dissecting microscope, a midline cervical incision was made and the left and right carotid arteries were exposed by blunt and sharp dissection. The left or right common carotid artery was ligated proximal to the bifurcation using sterile 4-0 to 6-0 silk suture. In sham-operated animals, the suture was passed under the exposed left common carotid artery but not tightened. The surgical wound was closed using 4-0 nylon suture with a simple interrupted suture pattern. The mice were allowed to recover on a warming blanket and continued on high fat diet for two weeks before study was terminated. Treatment was initiated on a day of surgery where treatment groups (n=10) received either sterile vehicle solution, or a mixture of human wild-type proapolipoprotein-AI (SEQ ID NO:1) and human wild-type mature apolipoprotein-AI (SEQ ID NO:2) comprising a ratio of 37% human wild-type proapolipoprotein-AI: 63% human wild-type mature apolipoprotein-AI (wt %), or a second mixture comprising proapolipoprotein-AI-4WF (SEQ ID NO:3) and mature apolipoprotein-AI-4WF (SEQ ID NO:4) in a mixture having a ratio of 52% proapolipoprotein-AI-4WF: 48% mature apolipoprotein-AI-4WF (wt %). The relative concentration of the mixtures of pro and mature wild type Apo-AI or pro and mature Apo-AI-4WF received per injection was 0.4 mg/g, subcutaneously, providing a total of 8 injections over two weeks period.

Two weeks after surgery, animals were euthanized with $CO_2$, and the vascular tree was perfused with 5ml of sterile PBS. Common carotid arteries were dissected and tissue samples were immersed in 1 to 3 ml of 2:1 chloroform/methanol. After standing overnight, the tissue sample was removed from the extraction solvent. The solvent was utilized for cholesterol analysis, while delipidated vessels were paraffin embedded. Free cholesterol and cholesteryl esters in the extracts obtained after incubation of the intact artery in chloroform-methanol were measured by FPLC. For histology, equally spaced paraffin cross-sections were stained using modified Masson's trichrome procedure (Sigma, St. Louis, Mo.) that included elasin staining. Macrophages were visualized immunohistochemically using MAC-2 antibody (Cedarlane Laboratories, Burlington, Ontario).

Figure 6A:
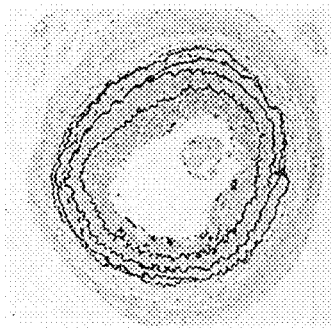
FIG. 6A represents a photograph of a carotid artery tissue section treated with control vehicle and stained with MAC-2 antibody to reveal luminal macrophages.

As illustrated in FIG. 6A, the artery which received only sterile vehicle solution treatment is substantially restricted by a relatively voluminous atherosclerotic plaque. This plaque is highlighted in FIG. 6A with an asterisk. FIG. 6B shows, at greater magnification, areas of MAC-2 staining, indicating the presence of macrophages. As shown in FIG. 6B, macrophages are interspersed regularly, and at fairly high density, throughout the plaque in the artery from an animal which received only sterile vehicle solution treatment.

Figure 6C:
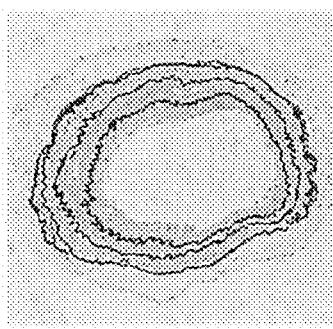
FIG. 6C represents a photograph of a carotid artery tissue section treated with a mixture of pro and mature Apo-AI-4WF and stained with MAC-2 antibody to reveal luminal macrophages.

FIG. 6C shows the arterial section from an animal which received Apo-AI-4WF treatment. As can be seen from FIG. 6C, the Apo-AI-4WF treatment significantly reduced the volume of the atherosclerotic plaque, relatively to the volume of the plaque in the in the vehicle-solution-only artery (FIG. 6A). In addition, as shown in FIG. 6D, there is far less MAC-2 staining, indicating substantial reduction in the number of macrophages in the Apo-AI-4WF treated artery, as compared to the vehicle solution treated artery.

Figure 6E:
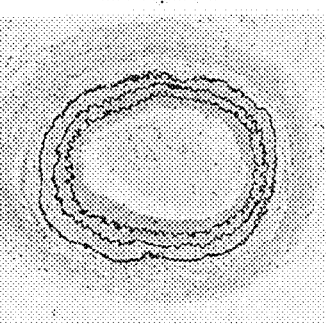
FIG. 6E represents a photograph of a carotid artery tissue section treated with a mixture of pro and mature ApoAI-WT and stained with MAC-2 antibody to reveal luminal macrophages.
Figure 6B:
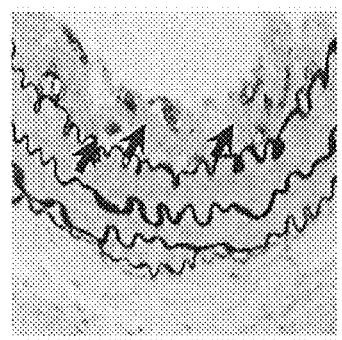
FIG. 6B represents a magnified image of a portion of a section of FIG. 6A.
Figure 6D:
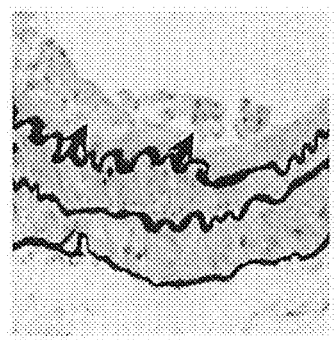
FIG. 6D represents a magnified image of a portion of a section of FIG. 6C.
Figure 6F:
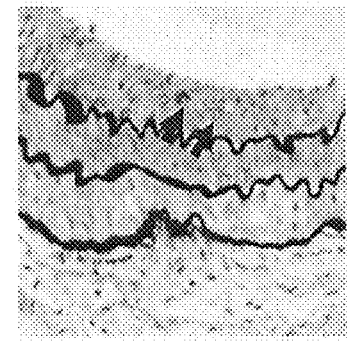
FIG. 6F represents a magnified image of a portion of a section of FIG. 6E.

FIG. 6E shows a section of the artery from an animal treated with an Apo-AI-WT mixture. As was the case for the Apo-AI-4WF mixture, Apo-AI-WT treatment resulted in a significant reduction in plaque volume relative to the artery treated with vehicle solution. In addition, as shown in FIG. 6F, there was also a reduction in macrophage density within the plaque, as indicated by diminished MAC-2 staining.

Overall, the data presented herein indicates that the mixtures of proapolipoproteins 4WF and WT-AI and their respective mature apolipoproteins are effective in reducing the plaque volume in carotid arteries of established mouse models of atherosclerosis. Furthermore, the degree of inflammatory macrophage infiltration is also reduced or diminished when the animals are dosed with mixtures of proapolipoproteins 4WF and WT-AI and their respective mature apolipoproteins, thereby suggesting a role for mixtures of proapolipoproteins 4WF and WT-AI and their respective mature apolipoproteins in the treatment and reversal of atherosclerosis as a treatment for cardiovascular and inflammatory diseases or disorders.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A pharmaceutical composition comprising a mixture of a human proapolipoprotein-4WF (SEQ ID NO: 3), and human mature apolipoprotein-4WF (SEQ ID NO: 4).

2. The pharmaceutical composition of claim 1, wherein the ratio of proapolipoprotein-4WF to corresponding apolipoprotein-4WF in the mixture ranges from about 5:95 to about 95:5 (wt %).

3. The pharmaceutical composition of claim 2, wherein the ratio of proapolipoprotein-4WF to corresponding apolipoprotein-4WF in the mixture ranges from about 20:80 to about 80:20 (wt %).

4. The pharmaceutical composition of claim 3, wherein the ratio of proapolipoprotein-4WF to corresponding apolipoprotein-4WF in the mixture ranges from about 35:65 to about 65:35 (wt %).

5. The pharmaceutical composition of claim 4, wherein the ratio of proapolipoprotein-4WF to corresponding apolipoprotein-4WF in the mixture ranges from about 40:60 to about 60:40 (wt %).

6. The pharmaceutical composition of claim 4, wherein the ratio of proapolipoprotein-4WF to corresponding apolipoprotein-4WF in the mixture ranges from about 45:55 to about 55:45 (wt %).

7. The pharmaceutical composition of claim 6, wherein the ratio of proapolipoprotein-4WF to corresponding apolipoprotein-4WF in the mixture ranges from about 50:50 (wt %).

8. The pharmaceutical composition of claim 1, wherein the amount of mature apolipoprotein-4WF in the mixture is at least about 25 mg.

9. The pharmaceutical composition of claim 1, wherein the amount of mature apolipoprotein-4WF in the mixture is at least about 50 mg.

10. The pharmaceutical composition of claim 1, wherein the amount of mature apolipoprotein-4WF in the mixture is at least about 75 mg.

11. The pharmaceutical composition of claim 1, wherein the amount of mature apolipoprotein-4WF in the mixture is at least about 100 mg.

12. The pharmaceutical composition of claim 1, wherein the amount of mature apolipoprotein-4WF in the mixture is at least about 125 mg.

13. The pharmaceutical composition of claim 1, wherein the amount of mature apolipoprotein-4WF in the mixture is at least about 150 mg.

14. The pharmaceutical composition of claim 1, wherein the amount of mature apolipoprotein-4WF in the mixture is at least about 175 mg.

15. The pharmaceutical composition of claim 1, wherein the amount of mature apolipoprotein-4WF in the mixture is at least about 200 mg.

16. The pharmaceutical composition of claim 1, wherein the combined amount of proapolipoprotein-4WF and the corresponding mature apolipoprotein-4WF is at least about 100 mg.

17. The pharmaceutical composition of claim 1, wherein the combined amount of proapolipoprotein-4WF and the corresponding mature apolipoprotein-4WF is at least about 150 mg.

18. The pharmaceutical composition of claim 17, wherein the combined amount of proapolipoprotein-4WF and the corresponding mature apolipoprotein-4WF is at least about 200 mg.

19. The pharmaceutical composition of claim 17, wherein the combined amount of proapolipoprotein-4WF and the corresponding mature apolipoprotein-4WF is at least about 250 mg.

20. The pharmaceutical composition of claim 17, wherein the combined amount of proapolipoprotein-4WF and the corresponding mature apolipoprotein-4WF is at least about 300 mg.

21. The pharmaceutical composition of claim 17, wherein the combined amount of proapolipoprotein-4WF and the corresponding mature apolipoprotein-4WF is at least about 400 mg.

22. The pharmaceutical composition of claim 1, wherein the combined amount of proapolipoprotein-4WF and the corresponding mature apolipoprotein-4WF in the mixture ranges from about 25 mg to about 8,350 mg.

23. The pharmaceutical composition of claim 22, wherein the combined amount of proapolipoprotein-4WF and the corresponding mature apolipoprotein-4WF in the mixture ranges from about 25 mg to about 5,000 mg.

24. The pharmaceutical composition of 1, wherein the composition comprises a volume of about 0.5 mL to about 40 mL.

25. The pharmaceutical composition of claim 24, wherein the composition comprises a volume of about 1 mL to about 30 mL.

26. The pharmaceutical composition of claim 1, wherein the pharmaceutical composition further comprises a pharmaceutically acceptable excipient.

27. The pharmaceutical composition of claim 1, wherein the mature apolipoprotein-4WF is substantially free from a phospholipid, a triglyceride, a lipid, cholesterol, glycerol, a liposome, or combinations thereof.

28. The pharmaceutical composition of claim 1, wherein the mixture of proapolipoprotein-4WF and corresponding mature apolipoprotein-4WF is formulated with a pharmaceutically acceptable liquid excipient.

29. The pharmaceutical composition of claim 1, wherein the mixture of proapolipoprotein-4WF and corresponding mature apolipoprotein-4WF is soluble in 2.0 mL of liquid or less.

30. The pharmaceutical composition of claim 1, wherein the mixture of proapolipoprotein-4WF and corresponding mature apolipoprotein-4WF is soluble in 1.5 mL of liquid or less.

31. The pharmaceutical composition of claim 1, wherein the mixture of proapolipoprotein-4WF and corresponding mature apolipoprotein-4WF is soluble in 1.0 mL of liquid or less.

32. The pharmaceutical composition of claim 1, wherein the mixture comprises a ratio of proapolipoprotein-4WF to corresponding mature apolipoprotein-4WF ranging from about 45:55 to about 55:45 (wt %), and the amount of mature apolipoprotein-4WF in the mixture ranges from about 25 mg to about 3,750 mg.

33. The pharmaceutical composition of claim 1, wherein the mixture comprises a ratio of proapolipoprotein-4WF to corresponding mature apolipoprotein-4WF ranging from about 35:65 to about 65:35 (wt %), and the amount of mature apolipoprotein-4WF in the mixture ranges from about 25 mg to about 3,750 mg.

34. The pharmaceutical composition of claim 1, wherein the composition further comprises apolipoprotein-AI, apolipoprotein-AII, apolipoprotein-AIV apolipoprotein-AV, apolipoprotein-B, apolipoprotein-E, apolipoprotein AI-Milano, apolipoprotein AI-Paris, apolipoprotein AI-Marburg, or combinations thereof.

35. An injectable apolipoprotein composition comprising: a) mixture of human proapolipoprotein-4WF (SEQ ID NO: 3), and a corresponding human mature apolipoprotein-4WF (SEQ ID NO:4), and b) at least one pharmaceutically acceptable excipient.

36. The injectable apolipoprotein composition of claim 35, wherein the injectable composition is sterile.

37. The injectable apolipoprotein composition of claim 35, wherein the composition is chemically stable upon prolonged storage.

38. The injectable apolipoprotein composition of claim 35, wherein the composition is stable for at least about 72 hours.

39. The injectable apolipoprotein composition of claim 35, wherein the amount of the combined proapolipoprotein-4WF to corresponding mature apolipoprotein-4WF in the mixture is about 25 mg to about 5,000 mg.

40. The injectable apolipoprotein composition of claim 35, wherein the ratio of proapolipoprotein-4WF to corresponding mature apolipoprotein-4WF in the mixture ranges from about 5:95 to about 95:5 (wt %).

41. The injectable apolipoprotein composition of claim 35, wherein the ratio of proapolipoprotein-4WF to corresponding mature apolipoprotein-4WF in the mixture ranges from about 20:80 to about 80:20 (wt %).

42. The injectable apolipoprotein composition of claim 35, wherein the ratio of proapolipoprotein-4WF to corresponding mature apolipoprotein-4WF in the mixture ranges from about 35:65 to about 65:35 (wt %).

43. The injectable apolipoprotein composition of claim 35, wherein the ratio of proapolipoprotein-4WF to corresponding mature apolipoprotein-4WF in the mixture ranges from about 40:60 to about 60:40 (wt %).

44. The injectable apolipoprotein composition of claim 35, wherein the ratio of proapolipoprotein-4WF to corresponding mature apolipoprotein-4WF in the mixture ranges from about 45:55 to about 55:45 (wt %).

45. The injectable apolipoprotein composition of claim 35, wherein the ratio of proapolipoprotein-4WF to corresponding mature apolipoprotein-4WF in the mixture ranges from about 50:50 (wt %).

46. The injectable apolipoprotein composition of claim 35, wherein the amount of mature apolipoprotein-4WF in the mixture is at least 25 mg.

47. The injectable apolipoprotein composition of claim 35, wherein the amount of mature apolipoprotein-4WF in the mixture is at least 50 mg.

48. The injectable apolipoprotein composition of claim 35, wherein the amount of mature apolipoprotein-4WF in the mixture is at least 75 mg.

49. The injectable apolipoprotein composition of claim 35, wherein the amount of mature apolipoprotein-4WF in the mixture is at least 100 mg.

50. The injectable apolipoprotein composition of claim 35, wherein the amount of mature apolipoprotein-4WF in the mixture is at least 125 mg.

51. The injectable apolipoprotein composition of claim 35, wherein the amount of mature apolipoprotein-4WF in the mixture is at least 150 mg.

52. The injectable apolipoprotein composition of claim 35, wherein the amount of mature apolipoprotei-4WF in the mixture is at least 175 mg.

53. The injectable apolipoprotein composition of claim 35, wherein the amount of mature apolipoprotein-4WF in the mixture is at least 200 mg.

54. The injectable apolipoprotein composition of claim 35, wherein the combined amount of proapolipoprotein-4WF and the corresponding mature apolipoprotein-4WF is from about 25 mg to about 5,000 mg.

55. The injectable apolipoprotein composition of claim 35, wherein the combined amount of proapolipoprotein-4WF and the corresponding mature apolipoprotein-4WF is from about 100 mg to about 3,500 mg.

56. The injectable apolipoprotein composition of claim 35, wherein the combined amount of proapolipoprotein-4WF and the corresponding mature apolipoprotein-4WF is from about 100 mg to about 2,750 mg.

57. The injectable apolipoprotein composition of claim 35, wherein the combined amount of pro apolipoprotein-4WF and the corresponding mature apolipoprotein-4WF is from about 100 mg to about 2,000 mg.

58. The injectable apolipoprotein composition of claim 35, wherein the combined amount of proapolipoprotein-4WF and the corresponding mature apolipoprotein-4WF is from about 100 mg to about 1,500 mg.

59. The injectable apolipoprotein composition of claim 35, wherein the combined amount of proapolipoprotein-4WF and the corresponding mature apolipoprotein-4WF is from about 700 mg to about 5,000 mg.

60. The injectable apolipoprotein composition of claim 35, comprising from about 25 mg to about 5,000 mg of the mixture of proapolipoprotein-4WF and corresponding mature apoliporotein-4WF, and from about 0.5 to about 30 mL of a suspending agent, wherein the ratio of proapolipoprotein-4WF to corresponding mature apoliporotein-4WF in the composition ranges from about 5:95 to 95:5 (wt %).

* * * * *

SEQUENCE LISTING

```
<160> NUMBER OF SEQ ID NOS: 4

<210> SEQ ID NO 1
<211> LENGTH: 249
<212> TYPE: PRT
<213> ORGANISM: Homo sapiens

<400> SEQUENCE: 1

Arg His Phe Trp Gln Gln Asp Glu Pro Pro Gln Ser Pro Trp Asp Arg
1               5                   10                  15

Val Lys Asp Leu Ala Thr Val Tyr Val Asp Val Leu Lys Asp Ser Gly
            20                  25                  30

Arg Asp Tyr Val Ser Gln Phe Glu Gly Ser Ala Leu Gly Lys Gln Leu
        35                  40                  45

Asn Leu Lys Leu Leu Asp Asn Trp Asp Ser Val Thr Ser Thr Phe Ser
    50                  55                  60

Lys Leu Arg Glu Gln Leu Gly Pro Val Thr Gln Glu Phe Trp Asp Asn
65                  70                  75                  80

Leu Glu Lys Glu Thr Glu Gly Leu Arg Gln Glu Met Ser Lys Asp Leu
                85                  90                  95

Glu Glu Val Lys Ala Lys Val Gln Pro Tyr Leu Asp Asp Phe Gln Lys
            100                 105                 110

Lys Trp Gln Glu Glu Met Glu Leu Tyr Arg Gln Lys Val Glu Pro Leu
        115                 120                 125

Arg Ala Glu Leu Gln Glu Gly Ala Arg Gln Lys Leu His Glu Leu Gln
```

```
                130                 135                 140
Glu Lys Leu Ser Pro Leu Gly Glu Glu Met Arg Asp Arg Ala Arg Ala
145                 150                 155                 160

His Val Asp Ala Leu Arg Thr His Leu Ala Pro Tyr Ser Asp Glu Leu
                165                 170                 175

Arg Gln Arg Leu Ala Ala Arg Leu Glu Ala Leu Lys Glu Asn Gly Gly
            180                 185                 190

Ala Arg Leu Ala Glu Tyr His Ala Lys Ala Thr Glu His Leu Ser Thr
        195                 200                 205

Leu Ser Glu Lys Ala Lys Pro Ala Leu Glu Asp Leu Arg Gln Gly Leu
    210                 215                 220

Leu Pro Val Leu Glu Ser Phe Lys Val Ser Phe Leu Ser Ala Leu Glu
225                 230                 235                 240

Glu Tyr Thr Lys Lys Leu Asn Thr Gln
                245

<210> SEQ ID NO 2
<211> LENGTH: 243
<212> TYPE: PRT
<213> ORGANISM: Homo sapiens

<400> SEQUENCE: 2

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

-continued

```
<210> SEQ ID NO 3
<211> LENGTH: 249
<212> TYPE: PRT
<213> ORGANISM: Homo sapiens

<400> SEQUENCE: 3

Arg His Phe Trp Gln Gln Asp Glu Pro Pro Gln Ser Pro Phe Asp Arg
1               5                   10                  15

Val Lys Asp Leu Ala Thr Val Tyr Val Asp Val Leu Lys Asp Ser Gly
            20                  25                  30

Arg Asp Tyr Val Ser Gln Phe Glu Gly Ser Ala Leu Gly Lys Gln Leu
        35                  40                  45

Asn Leu Lys Leu Leu Asp Asn Phe Asp Ser Val Thr Ser Thr Phe Ser
    50                  55                  60

Lys Leu Arg Glu Gln Leu Gly Pro Val Thr Gln Glu Phe Phe Asp Asn
65                  70                  75                  80

Leu Glu Lys Glu Thr Glu Gly Leu Arg Gln Glu Met Ser Lys Asp Leu
                85                  90                  95

Glu Glu Val Lys Ala Lys Val Gln Pro Tyr Leu Asp Asp Phe Gln Lys
            100                 105                 110

Lys Phe Gln Glu Glu Met Glu Leu Tyr Arg Gln Lys Val Glu Pro Leu
        115                 120                 125

Arg Ala Glu Leu Gln Glu Gly Ala Arg Gln Lys Leu His Glu Leu Gln
    130                 135                 140

Glu Lys Leu Ser Pro Leu Gly Glu Glu Met Arg Asp Arg Ala Arg Ala
145                 150                 155                 160

His Val Asp Ala Leu Arg Thr His Leu Ala Pro Tyr Ser Asp Glu Leu
                165                 170                 175

Arg Gln Arg Leu Ala Ala Arg Leu Glu Ala Leu Lys Glu Asn Gly Gly
            180                 185                 190

Ala Arg Leu Ala Glu Tyr His Ala Lys Ala Thr Glu His Leu Ser Thr
        195                 200                 205

Leu Ser Glu Lys Ala Lys Pro Ala Leu Glu Asp Leu Arg Gln Gly Leu
    210                 215                 220

Leu Pro Val Leu Glu Ser Phe Lys Val Ser Phe Leu Ser Ala Leu Glu
225                 230                 235                 240

Glu Tyr Thr Lys Lys Leu Asn Thr Gln
                245

<210> SEQ ID NO 4
<211> LENGTH: 243
<212> TYPE: PRT
<213> ORGANISM: Homo sapiens

<400> SEQUENCE: 4

Asp Glu Pro Pro Gln Ser Pro Phe Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Phe Asp Ser Val Thr Ser Thr Phe Ser Lys Leu Arg Glu Gln Leu
    50                  55                  60

Gly Pro Val Thr Gln Glu Phe Phe Asp Asn Leu Glu Lys Glu Thr Glu
65                  70                  75                  80

Gly Leu Arg Gln Glu Met Ser Lys Asp Leu Glu Glu Val Lys Ala Lys
```

```
                          85                      90                      95
Val Gln Pro Tyr Leu Asp Asp Phe Gln Lys Lys Phe Gln Glu Glu Met
                100                     105                 110

Glu Leu Tyr Arg Gln Lys Val Glu Pro Leu Arg Ala Glu Leu Gln Glu
        115                     120                 125

Gly Ala Arg Gln Lys Leu His Glu Leu Gln Glu Lys Leu Ser Pro Leu
    130                     135                 140

Gly Glu Glu Met Arg Asp Arg Ala Arg Ala His Val Asp Ala Leu Arg
145                     150                 155                 160

Thr His Leu Ala Pro Tyr Ser Asp Glu Leu Arg Gln Arg Leu Ala Ala
                165                     170                 175

Arg Leu Glu Ala Leu Lys Glu Asn Gly Gly Ala Arg Leu Ala Glu Tyr
                180                     185                 190

His Ala Lys Ala Thr Glu His Leu Ser Thr Leu Ser Glu Lys Ala Lys
        195                     200                 205

Pro Ala Leu Glu Asp Leu Arg Gln Gly Leu Leu Pro Val Leu Glu Ser
        210                     215                 220

Phe Lys Val Ser Phe Leu Ser Ala Leu Glu Glu Tyr Thr Lys Lys Leu
225                     230                 235                 240

Asn Thr Gln
```